US007595186B2

(12) United States Patent
Gerdes et al.

(10) Patent No.: US 7,595,186 B2
(45) Date of Patent: Sep. 29, 2009

(54) CYTOTOXIN-BASED BIOLOGICAL CONTAINMENT

(75) Inventors: Kenn Gerdes, Odense S (DK); Marie Mikkelsen, Odense C (DK); Hugo Gronlund, Odense V (DK); Kim Pedersen, Odense C (DK); Peter Kristoffersen, Frederiksberg (DK)

(73) Assignee: Université Libre de Bruxelles, Brussels (BE)

( * ) Notice: Subject to any disclaimer, the term of this patent is extended or adjusted under 35 U.S.C. 154(b) by 16 days.

(21) Appl. No.: 11/837,456

(22) Filed: Aug. 10, 2007

(65) Prior Publication Data

US 2008/0206840 A1    Aug. 28, 2008

Related U.S. Application Data

(62) Division of application No. 11/558,856, filed on Nov. 10, 2006, which is a division of application No. 09/700,130, filed as application No. PCT/DK99/00258 on May 7, 1999, now Pat. No. 7,183,097.

(60) Provisional application No. 60/085,067, filed on May 12, 1998.

(30) Foreign Application Priority Data

May 7, 1998  (DK) ..................................... 0627/98

(51) Int. Cl.
  *C12N 1/20* (2006.01)
(52) U.S. Cl. ............................... 435/252.3; 435/252.31
(58) Field of Classification Search ............... 435/252.3
  See application file for complete search history.

(56) References Cited

U.S. PATENT DOCUMENTS

| | | | |
|---|---|---|---|
| 5,300,431 A | 4/1994 | Pierce et al. | |
| 5,631,153 A | 5/1997 | Capecchi et al. | |
| 5,855,732 A | 1/1999 | Yoshida | |
| 5,888,732 A | 3/1999 | Hartley et al. | |
| 5,910,438 A | 6/1999 | Bernard et al. | |
| 6,143,557 A | 11/2000 | Hartley et al. | |
| 6,171,861 B1 | 1/2001 | Hartley et al. | |
| 6,180,407 B1 | 1/2001 | Bernard et al. | |
| 6,270,969 B1 | 8/2001 | Hartley et al. | |
| 6,271,359 B1 | 8/2001 | Norris et al. | |
| 2004/0115811 A1 | 6/2004 | Gabant | |
| 2005/0130308 A1 | 6/2005 | Bernard | |
| 2005/0260585 A1 | 11/2005 | Szpirer | |

FOREIGN PATENT DOCUMENTS

| | | |
|---|---|---|
| DE | 10038573 | 2/2002 |
| WO | WO 94/03616 | 2/1994 |
| WO | WO 9713401 | 4/1997 |
| WO | WO 99/21977 | 5/1999 |
| WO | WO 01/31039 | 5/2001 |
| WO | WO 01/42509 | 6/2001 |
| WO | WO 01/46444 | 6/2001 |
| WO | WO 02/12474 A2 | 2/2002 |
| WO | WO 2004/022745 | 3/2004 |

OTHER PUBLICATIONS (1992) Journal of Cellular Biochemistry, Keystone Symposia on Molecular & Cellular Biology, 104.
Abremski, et al. (1984) Bacteriophage P1 Site-specific Recombination. J. Bio. I. Chem. 259(3):1509-1514.
Aizenman, et al. (1996) an *Escherichia coli* chromosomal "addiction module" regulated by 3', 5'—bispyrophosphate: A modayk for programmed bacterial cell death. Proc. Natl. Acad. Sci. 93:6059-6063.
Backman, K. And H.W. Boyer (1983) "Tetracycline Resistance Determined by pBR322 is Mediated by one Polypeptide." Gene 26. pp. 197-203.
Bahassi, et al. (1995) F plasmid CcdB killer protein: *ccdB* gene mutants coding for non-cytotoxic proteins which retain their regulatory functions. Molecular Microbiology 15(6):1031-1037.
Baubonis, et al. (1993) Genomic Targeting with Purified Cre Recombinase. Nucleic Acids Research 21(9):2025-2029.
Baum, James A. "Tn5401, a New Class II Transposable Element form *Bacillus thuringiensis*" J. of Bacteriology, (May 1994) 176(10):2835-2845.
Bech, et al., "Sequence of the relB transcription unit from *Escherichla coli* and identification of the relB gene", The EMBO J., (1985) 4(4):1059-1066.
Bernard (1996) Positive Selection of Recombinant DNA by CcdB. BioTechniques 21(2)320-323.
Bernard, et al. (1991) The 41 carboxy-terminal residues of the miniF plasmid CcdA protein are sufficient to antagonize the killer activity of the CcdB protein. Mol. Gen Genet 226:297-304.
Bernard, et al. (1992) Cell Killing by the F Plasmid CcdB protein involves poisoning of DNA-topoisomerase II complexes. J. Mol. Biol. 226:735-745.
Bex, et al. (1983) Mini-F encoded proteins: Identification of a new 10.5 kilodalton species. The EMBO Journal, 2(11):1853-1861.
Biswas, et al. (1993) High-Efficiency Gene Inactivation and Replacement System for Gram-Positive Bacteria. J. Bacteriology 175(11):3628-3635.
Bochner, et al. (1980) Positive Selection for Loss of Tetracycline Resistance. J. Bacteriology 143(2):923-933.

(Continued)

*Primary Examiner*—Mark Navarro
(74) *Attorney, Agent, or Firm*—Knobbe Martens Olson & Bear

(57) ABSTRACT

Method of conditionally controlling the survivability of a recombinant cell population and of containing such cells to an environment or containing replicons to a host cell is based on the use of proteic killer systems including *E. coli* relBE locus and similar systems found in Gram-negative and Gram-positive bacteria and Archae. Such systems are generally based on a cytotoxin polypeptide and an antitoxin or antidote polypeptide that in contrast to the cytotoxin is degradable by proteases. The recombinant cells are useful as vaccines, pollutant degrading organisms or as biological pest control organism e.g. expressing *B. thuringiensis* crystalline proteins.

23 Claims, 22 Drawing Sheets

OTHER PUBLICATIONS

Boyd (1993) Turbo Cloning: A Fast, Efficient Method for Cloning PCR Products and Other Blunt-Ended DNA Fragments into Plasmids. Nucleic Acids Research 21(4):817-821.

Bravo, et al. (1988) Killing of *Escherichia coli* cells modulated by components of the stability system ParD of plasmid R1. Mol. Gen. Genet. 215:146-151.

Bubeck, et al. (1993) Rapid Cloning by Homologous Recombination in vivo. Nucleic Acids Research 21(15):3601-3602.

Bult, Carol J., "Complete Genome Sequence of the Methanogenic Archaeon, *Methanococcus jannaschii*", Science, (1998) 273:1058-1073.

Burns, et al. (1984) Positive Selection Vectors: A Small Plasmid Vector Useful for the Direct Selection of Sau2A-generated overlapping DNA Fragments. Gene 27:323-325.

Cole, et al., "Deciphering the biology of *Mycobacterium tuberculosis* from the complete genome sequence", Nature, (Jun. 11, 1998) 393:537-544.

Couturier, et al. (1998) Bacterial death by DNA gyrase poisoning. Trends in Microbiology 6(7):269-275.

Craine (1982) Novel Selection for Tetracycline-or Chloramphenicol-Sensitive *Escherichia coli*. J. Bacteriology 151(1):487-490.

Ebert et al. "A Moloney MLV-Rat Somatotropin Fusion Gene Produces Biologically Active Somatotropin in a transgenic pig." Molecular Endocrinology. 2:277-283, 1988.

Fleischmann, et al., "Whole-Genome Random Sequencing and Assembly of *Haemophilus influenzae* Rd,", Science, (Jul. 28, 1995) 269:496-512.

Gabant et al., 1997 "Bifunctional lacZ a-ccdB Genes for selective Cloning of PCR Products," Biotechniques 23:938-941.

Gabant, P., et al. (1998) Direct Selection Cloning Vectors Adapted to the Genetic Analysis of Gram-Negative Bacteria and their Plasmids. Gene 207., pp. 87-92.

Gabant, P., et al. (2000) "New Positive Selection System Based on the parD (kis/kid)System of the R1 Plasmid." BioTechniques 28:784-788.

Gabant et al. 2001 "Use of Poison/antidote systems for selective Cloning," in Plasmid Biology 2000: International Symposium on Molecular Biology of Bacterial Plasmids, Meeting Abstracts, pp. 135-170, Plasmid 45:160-161.

Gerdes (2000) Toxin-Antitoxin modules may regulate synthesis of macromolecules during nutritional stress. Journal of Bacteriology 182:561-572.

Golfredsen, et al., "The *Escherichla coli* relBE genes belong to a new toxin-antitoxin gene family", Molecular Microbiology, (1998) 29(4):1065-1076.

Gossen, J.A., et al. (1992) Application of Galactose-Sensitive *E.coli* Strains as Selective Hosts for LacZ Plasmids. Nucleic Acids Res. 20,pp. 3254.

Gronenborn (1978) Methylation of single-stranded DNA in vitro introduces new restriction endonuclease cleavage sites. Nature, 272:375-377.

Gronlund, et al., "Toxin-Antitoxin Systems Homologous with relBE of *Escherichia coli* Plasmid P307 are Ubiquitous in Prokaryotes", J. of Molecular Biology, (Jan. 29, 1999) 285(4):1401-1415.

Guilfoyle, R.A., and L.M. Smith (1994) "A Direct Selection Strategy for Stotgun Cloning and Sequencing in the Bacteriophage M13." Nucleic Acids Res.22, pp. 100-107.

Guzman, L.M. et al. (1995) "Tight Regulation, Modulation and High-Level Expression by Vectors Containing the Arabinose Pbad Promoter." J. Bact. 177,pp. 4121-4130.

Hammer et al. "Genetic Engineering of Mammalian Embryos." J. Anim. Sci. 63:269-278, 1986.

Hartley et al. 2000 "DNA Cloning Using in Vitro Site-Specific Recombination," Genome Res. 10:1788-1795.

Hebsgaard, S.M., et al. (1996) "Splice Site Prediction in *Arabidopsis thaliana* Pre-mRNA by Combining Local and Global Sequence information." Nucleic Acids Research, 24(17) 3439-3452.

Henrich, et al. (1986) Use of the lysis gene of bateriophage ΦX174 for the construction of a positive selection of a positive selection vector. Gene 42:345-349.

Herrero, M., et al.(1990) "Transposon Vectors Containing Non-Antibiotic Resistance Selection markers for Cloning and Stable Chromosomal Insertion of Foreign Genes in Gram-Negative Bacteria." J. Bact. 172, pp. 6557-6567.

Holt, et al. (1993) A Novel Phage λ Replacement Cre-lox Vector that has Automatic Subcloning Capabilities. Gene 133:95-97.

Ioannou, et al. (1994) A new bacteriophage P1-derived vector for the propagation of large human DNA fragments. Nature Genetics 6:84-89.

Jensen, et al., "Programmed cell death in bacteria: proteic plasmid stabilization systems" Molecular Microbiology, (1995) 17(2):205-210.

Jensen, et al. 1995 "Comparison of ccd of F, parDE of RP4, and parD of R1 using a novel conditional replication control system of plasmid R1," Mol. Microbiol. 17:211-220.

Kaneko, et al., "Sequence Analysis of the Genome of the Unicellular Cyanobacterium *synechocystis* sp. Strain PCC6803. II. Sequence Determination of the Entire Genome and Assignment of Potential Protein-coding Regions" DNA Research, (1996) 3:109-136.

Karoui, et al. (1983) *Ham22*, a mini-F mutation which is lethal to host cell and promotes recA-dependent induction of lambdoid prophage. The EMBO Journal. 2(11): 1863-1868.

Kuhn, et al (1986) Positive-selection vectors utilizing lethality of the EcoRI endonuclease. Gene,44:253-263.

Landy (1989) Dynamic, Structural, and Regulatory Aspects of λ Site-Specific Recombination. Annu. Rev. Biochem. 58:913-949.

Lehnherr, et al. (1993) Plasmid Addiction Genes of Bacteriophage P1: *doc*, which cause cell death on curing of prophage, and *phd*, which prevents host death when prophage is retained. J. Mol. Biol. 233:414-428.

Liu (1989) DNA Topoisomerase poisons as antitumor drugs. Annu. Rev. Biochem. 58:351-375.

Maki, et al (1992) Modulation of DNA Supercoiling Activity of *Escherichia coli* DNA Gyrase by F Plasmid. The Journal of Biological Chemistry vol. 267(17):12244-12251.

Maloy, et al. (1981) Selection for Loss of Tetracycline Resistance by *Escherichia coli*. J. Bacteriology 145(2):1110-1112.

Manning, P.A., "Nucleotide sequence encoding the mannose-tucose-resistant hemagglutinin of *Vibrio cholerae* 01 and construction of a mutant", EMBL Sequence Database, (Aug. 7, 1993) 1-7.

Maxwell, et al. (1986) Mechanistic aspects of DNA Topoisomerases. Advan. Protein Chem. 38:69-107.

Messing, et al. (1977) Filamentous coliphage M13 as a cloning vehicle: Insertion of a *Hin*dll fragment of the *lac* regulatory region in M13 replicative form in vitro. Proc Natl. Acad. Sci. 74(9):3642-3646.

Miki, et al. (1984) Control of Cell Division by Sex Factor F in *Escherichia coli*. J. Mol. Biol. 174:605-625.

Miki, et al. (1984) Control of Cell Division by Sex Factor F in *Escherichia coli*. J. Mol. Biol. 174:627-646.

Moreadith et al. "Gene Targeting in Embryonic Stem Cells: The new Physiology and metabolism." J. Mol. Med. 75:208-216, 1997.

Mullins et al. "Perspective Series: Molecular Medicine in Genetically Engineered Animals." J. Clin. Invest. 98 (Suppl.): S37-S40, 1996.

Muyrers et al. 2001 "Techniques: rocombinogenic engineering—new options for cloning and manipulating DNA," Trends in Biochem. Sci. 26:325-331.

Murphy, et al. (1991) pλZd39:A New Type of cDNA Expression Vector for Low Background, High Efficiency Directional Cloning. Nucleic Acids Research 19(12):3403-3408.

Nilsson, et al. (1983) An Improved Positive Selection Plasmid Vector Constructed by Oligonucleotide Mediated Mutagenesis. Nucleic Acids Research 11(22):8019-8029.

Norrander, et al. (1983 Construction of improved M13 vectors using oligodeoxynucleotide-directed mutagenesis. Gene, 26:101-106.

Ogura, et al. (1983) Mini-F plasmid genes that couple host cell division to plasmid proliferation. Proc. Natl. Acad. Sci. USA, 80:4784-4788.

pGT-N28 Vector DNA (catalog #N3728) New England Biolabs Online Catalog, Jun. 2, 1999, p. 1, www.neb.com/neb/products/nucleic/307-28.html, the whole document.

pKO Scrambler Series Gene Targeting Vectors for Knockout Mice. Stratagene Online Catalog, Jan. 1998, pp. 1-3; www.stratagene.com/cellbio/toxicology/pko.htm, the whole document.

Peakman, et al. (1992) Highly Efficient Generation of Recombinant Baculoviruses by Enzymatically Mediated Site-Specific in vitro Recombination. Nucleic Acids Research 20(3):495-500.

Pecota et al. "Combining the Hok/Sok, parDE, and pnd Postsegregational killer loci to Enhance Plasmid Stability." Applied and Environmental Microbiology 63:1917-1924, 1997.

Phillppe-Bernard, et al., "Positive-selection vectors using the F plasmid ccdB killer gene", Gene, (1994) 148:71-74.

Pierce, et al. (1992) A positive selection vector for cloning high molecular weight DNA by the bacteriophage P1 system: Improved cloning efficacy. Proc. Natl. Acad. Sci. 89(6):2056-2060.

Roberts, et al. (1992) Definition of a Minimal Plasmid Stabilization System from the Broad-Host-Range Plasmid RK2. Journal of Bacteriology Dec. 1992:8119-8132.

Roberts, et al. (1994) the parDE operon of the broad-host-range plasmid RK2 specifies growth inhibition associated with plasmid loss. J. Mol. Biol. 18; 237 (1): 35-51.

Roca, et al. (1992) A Hit-and-Run System for Targeted Genetic Manipulations in Yeast. Nucleic Acid Research 20(17):4671-4672.

Ruiz-Echevarria, et al. (1991) the kis and kid genes of the parD maintenance system of plasmid R1 form an operon that is autoregulated at the level of transcription by the co-ordinated action of the Kis and Kid proteins. Molecular Microbiology 5(11):2685-2693.

Ruiz-Echevarria, et al. (1991) Structural and functional comparison between the stability systems ParD of plasmid R1 and Ccd of plasmid. F. Mol. Gen. Genet 225:355-362.

Ruiz-Echevarria et al. 1995 "A Mutation that decreases the efficiency of Plasmid R1 Replication Leads to the Activation of parD, a Killer Stability System of the Plasmid," FEMS Microb. Letters 130:129-136.

Sadler, et al. (1980) Plasmids containing many tandem copies of a synthetic lactose operator. Gene 8:279-300.

Salmon, et al., "The antidote and autoregulatory funtions of the F plasmid CcdA protein: a genetic and biochemical survey", Molecular and General Genetics, (1994) 244:530-538.

Sambrook, et al. (1989) Molecular Cloning: A Laboratory Manual. Cold Spring Harbor Laboratory Press, Cold Spring Harbor, NY, pp. xi-xxxviii.

Sambrook, et al. (1989) Molecular Cloning: A Laboratory Manual. Cold Spring Harbor Laboratory Press, Cold Spring Harbor, NY, pp. 4.12,A.9-A.13.

Saul, et al., Nucleotide Sequence and Replication Characteristics of RepFIB, a Basic Replicon of IncF Plasmids, J. of Bacteriology, (May 1989) 171(5):2697-2707.

Schlieper et al. 1998 "A Positive Selection Vector for Cloning of Long Polymerase Chain Reaction Fragments based on a lethal mutant of the crp Gene of Escherichia coli," Anal. Biochem. 257:203-209.

Seamark, R.F. "Progress and Emerging Problems in Livestock Transgenesis: a Summary perspective." Repod. Fert. Dev. 6:653-657, 1994.

Smith, et al. (1985) Modification and Selection of Human Interleukin 2 Produced in Insect Cells by Baculovirus Expression Vector. Natl Acad. Sci. 82:8404-8408.

Smith, et al. (1997) The poison-antidote stability system of the broad-host-range Thiobacilus ferroxidans plasmid pTF-FC2. Molecular Microbiology 26(5):961-970.

Sierra et al. 1998 "Functional Interactions between chpB and parD, two homologous conditional killer systems found in the Escherichia coli chormosome and in plasmid R1," FEMS Microb. Letters 168:51-58.

Simons, R.W., et al. (1987) "Improved Single and Multicopy Lac-Based Cloning Vectors for Protein and Operon Fusions." Gene 53, pp. 85-96.

Trudel, P., et al. (1996) pGATA: A Positive Selection Vector Based on the Toxicity of the Transcription Factor GATA-1 to Bacteria. BioTechniques. 20:684-693.

Tomb, et al., "The complete genome sequence of the gastric pathogen Hellcobacter pylori," Nature, (Aug. 7, 1997) 539-547.

Tsuchimoto, et al. (1988) Two Genes, pelK and pemI, responsible for stable maintenance of resistance plasmid R100. J. of Bateriol., 170(4):1461-1466.

Tsuchinnoto, et al. (1993) Autoregulation by cooperative binding of the PemI and PemK proteins to the promoter region of the pem operon. 237:81-88.

Tsuchimoto, et al (Journal of Bacteriology vol. 174, No. 13, pp. 4205-4211, Jul. 1992).

Van Reeth, T., et al. (1998) "Positive Selection Vectors to Generate Fused Genes for the Expression of His- Tagged Proteins." Biotechniques. 25(5):898-904.

Vemet, T., et al. (1985) "A Direct-Selection Vector Derived from pColE3-CA38 and adapted for Foreign Gene Expression." Gene 34:87-93.

Wang (1985) DNA Topoisomerases. Ann. Rev. Biochem. 54:665-697.

Yanisch-Perron, et al. (1985) Improved M13 phage closing vectors and host strains: Nucleotide sequence of the M13mp18 and pUC19 vectors. Gen, 33:103-119.

Yarmolinsky (1995) Programmed cell death in bacterial populations. Science, 267:836-837.

Yu et al. 2000 "An Efficient recombination system for chromosome engineering in Escherichia coli," PNAS USA 97:5978-5983.

International Preliminary Examination Report from PCT/BE03/00045, dated Feb. 24, 2004.

International Preliminary Examination Report from PCT/BE02/00021, dated Feb. 19, 2003.

International Search Report from PCT/BE02/00021, Dated Jul. 12, 2002.

International Search Report from PCT/BE00/00151, Dated May 22, 2001.

Office Action from U.S. Appl. No. 09/634,039, Dated Dec. 16, 2004.
Office Action from U.S. Appl. No. 09/634,039, Dated Jun. 29, 2005.
Office Action from U.S. Appl. No. 09/634,039, Dated Dec. 20, 2001.
Notice of Allowability from U.S. Appl. No. 08/379,614, Dated Mar. 3, 1998.
Office Action from U.S. Appl. No. 09/225,152, dated Sep. 13, 1999.
Office Action from U.S. Appl. No. 08/379,614, Dated Aug. 27, 1996.
Office Action from U.S. Appl. No. 08/379,614, Dated Aug. 4, 1997.
Office Action from U.S. Appl. No. 09/634,039, Dated Jan. 15, 2003.
Office Action from U.S. Appl. No. 09/634,039, dated Sep. 24, 2003.
U.S. Appl. No. 09/634,039, filed Aug. 8, 2000.

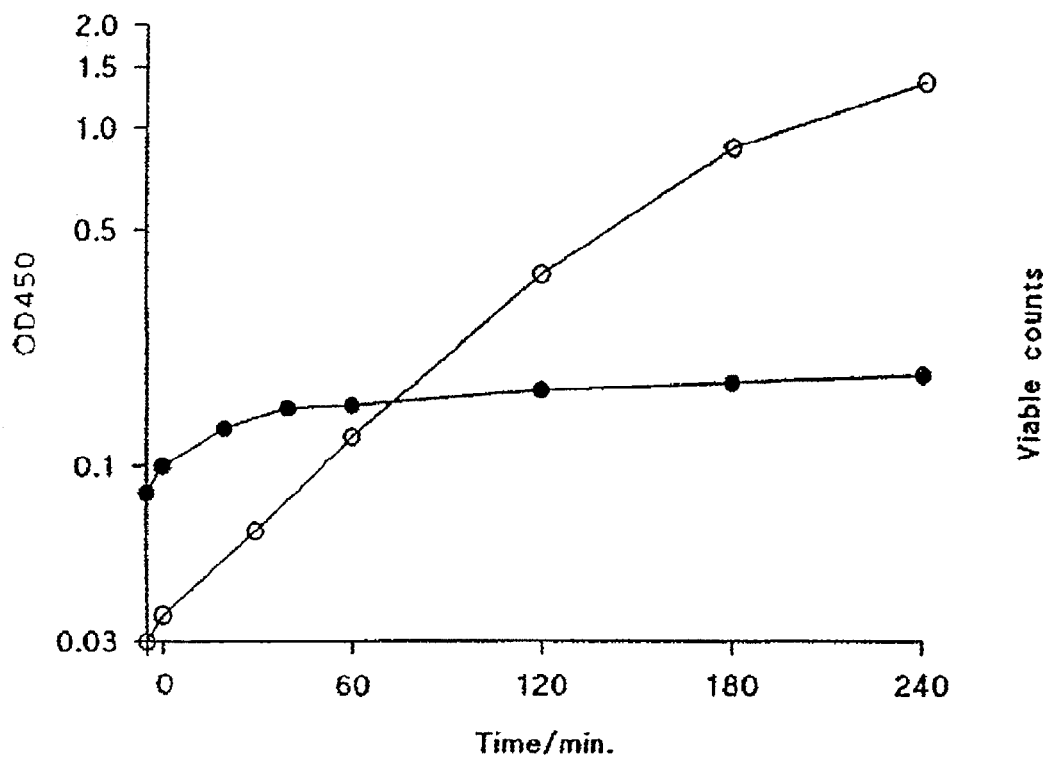
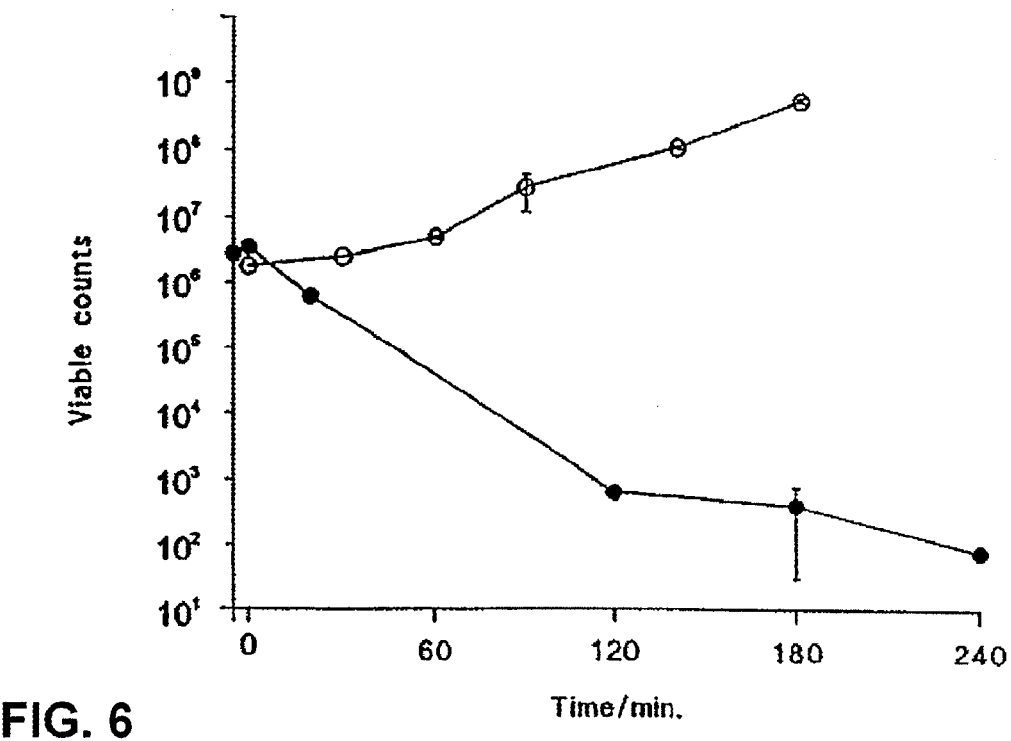
FIG. 6

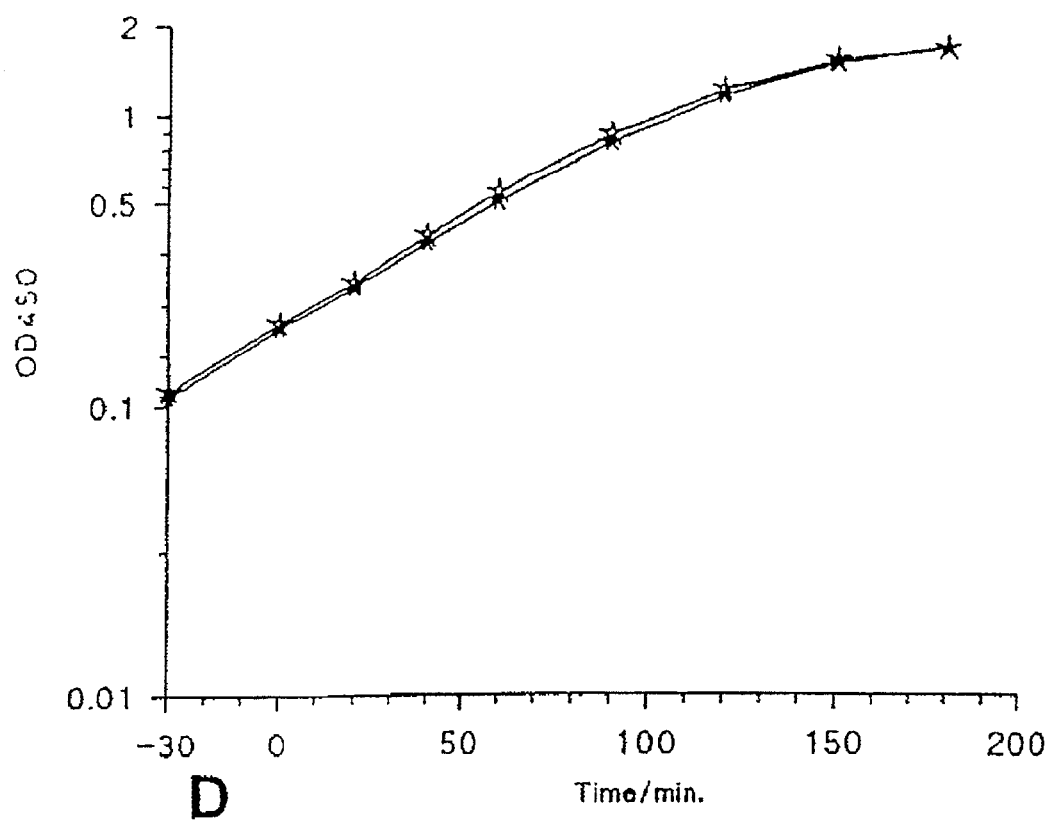
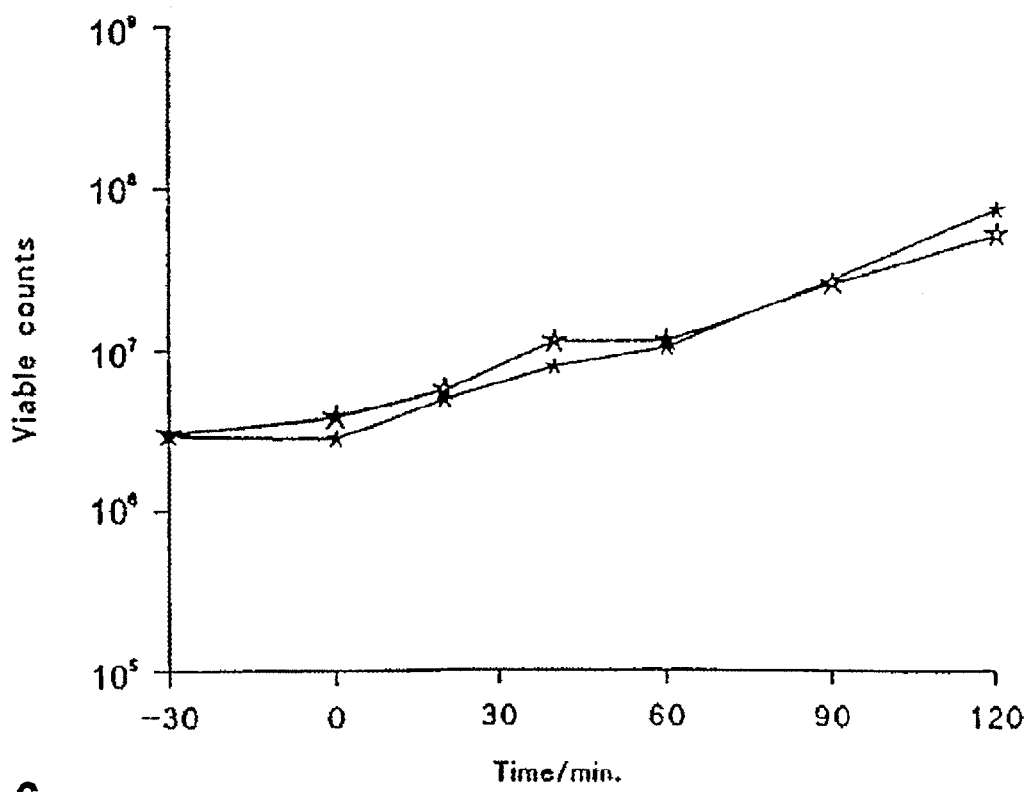
FIG. 6

DNA sequence of the relBE$_{Sp2}$ locus of *S. pneumoniae* (reverse complement of part of contig 80 in the tigr database)

```
   1  ACCCATGAGC ATTCAGATCA TATCCATGGA GTAGGCGTTT TGGCTCGCAA
  51  GTATGGTATG GATCTTTATG CCAATGAAAA GACCTGGCAA GCTATGGAAA
 101  ATAGTAAATA TCTTGGCAAG GTGGATTCTT CGCAAAAGCA TATTTTTGAA
 151  ATGGGTAAAA CCAAAACCTT TGGAGATATC GACATCGAGA GTTTTGGTGT
 201  AAGCCATGAT GCAGTCGCAC CGCAGTTCTA TCGCTTTATG AAGGATGATA
 251  AGAGTTTTGT CCTCTTGACA GATACAGGTT ATGTCAGTGA CCGTATGGCG
 301  GGCATTGTCG AAAATGCGGA TGGTTATCTT ATCGAGGCCA ACCATGATGT
 351  AGAGATTTTG CGATCAGGTT CTTACGCTTG GCGACTCAAA CAACGAATCC
 401  TATCTGACCT TGGTCACCTT TCTAACGAGG ACGGTGCTGA AGCTATGATT
 451  CGGACGCTAG GAAATCGTAC TAAGAAGATT TACCTTGGGC ATTTATCTAA
 501  GGAAACAAT ATCAAGGAAC TGGCTCATAT GACCATGGTC AATCAGCTGG
 551  CTCAAGCTGA TCTGGGAGTC GGAGTAGACT TTAAGGTTTA TGATACCTCA
 601  CCAGATACCG CAACACCATT GACAGAGATA TAGAAAGAAC GCTGAGAAGG
 651  TGTTCTTTTT ATATTGACTG AACACCTAAA AAGTAATACA ATGGTGTTAC
            SD           Start relB$_{Sp2}$
 701  CATTAAAAAA GGGAGCACAA AAGATGACTA CTATTACATT AAAAGTTTCT
 751  GAAGCTGATA AACATTTAT GAAAGCAATG GCTAAGTTTG AAGGAGTTTC
 801  CCTTTCGGAA CTTATTCGCA CCAAAACTCT GAAGCCCTA GAAGATGAAT
 851  ACGATGCTCG TGTGGCAGAT TTAGCCTATC AAGAGTATTT AGAAGACTTG
                                                           SD
 901  GAAAAAGGAG TTGAACCCAT TACTTGGGAA GAAATGATGC ATGATTAGG
       Start relE$_{Sp2}$/End relB$_{Sp2}$
 951  CTTGAAGGAT GAATAATTTG TATAAATTAG TTCCAACAAG ACGTTTTATC
1001  AAGCAATTGA AAAAATTGGA CCGTTATACG CAGAAGCTAA TTACAAACTA
1051  TTTACAAACC AATGTTTTGG AAGACCCAAG ACGACACGGA AAGGCTTTGG
1101  TTGGTAATCG CGTTGGTCAA TGGCGCTATA GAATTGGTAA TTATCGAGTT
1151  ATCGTACAAA TTGTAGATGA TGAATTAGTC GTTGCTACTC TAGAAGTTGG
                                    End relE$_{Sp2}$
1201  TCATCGGAGA GATATTTATT GAATTACTTT TTTCAAGTAA ATTTTCATTC
1251  TTTAAAATAT GATATAATAG GGCTTACAAT ATAAGAGAGG TTGCTGATGA
1301  CAATAGATAT TAGTGAAGAA AGTTTGGCTA AGAATCGGC TGACTTATTA
1351  AAAATTCTTT TAAAAGATCG AACGACAAAG AAATCAATTG TTTGGGCTAC
1401  GCATTCTTAT GAATTGTTAG GAAAGGGATT TGCTCCAAGT GATCGCATCA
1451  ATCCAAGTAA GGTTACTGGA AACTTTGCCA ACTTGATTCA GCCCAGATCT
1501  GAAAAATCCA AATATGAACA AAAGATCGG ACAAAAATAA GGGCAGAAGT
```

Protein sequences:

RelB$_{Sp2}$ (pHi=4.2):
mttitlkvse adktfmkama kfegvslsel irtktleale deydarvadl ayqeyledle kgvepitwee mmhdlglkde RelE$_{Sp2}$ (pHi=11.1):
mnnlyklvpt rrfikqlkkl drytqklitn ylqtnvledp rrhgkalvgn rvgqwryrig nyrvivqivd delvvatlev ghrrdiy

SEQUENCE LISTING

```
<160> NUMBER OF SEQ ID NOS: 59

<210> SEQ ID NO 1
<211> LENGTH: 51
<212> TYPE: DNA
<213> ORGANISM: Artificial Sequence
<220> FEATURE:
<223> OTHER INFORMATION: Primer

<400> SEQUENCE: 1
ccccggatcc ataaggagtt ttataaatgg cgtattttct ggattttgac g        51

<210> SEQ ID NO 2
<211> LENGTH: 38
<212> TYPE: DNA
<213> ORGANISM: Artificial Sequence
<220> FEATURE:
```

```
<223> OTHER INFORMATION: Primer

<400> SEQUENCE: 2
cccccctcga ggtcgactca gagaatgcgt ttgaccgc                          38

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
cccccggatc ccagtcttga aaggtggc                                     28

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
cccccgaatt ctcataggta tttatccag                                    29

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
ccccggatcc agatctggat aaatacc                                      27

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
cccccgaatt cgtaactttc tgtgtttatt gc                                32

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
cccccgagct cagatctgga taaatacc                                     28

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
cccccgcatg cgtaactttc tgtgtttatt gc                                32
```

<210> SEQ ID NO 9
<211> LENGTH: 1461
<212> TYPE: DNA
<213> ORGANISM: E. coli
<220> FEATURE:
<221> NAME/KEY: unsure
<222> LOCATION: 455, 715, 1025, 1237, 1456, 1457
<223> OTHER INFORMATION: n = A,T,C or G

<400> SEQUENCE: 9

```
cttaatttca ggccccatcg gatcacacat ggagagtttt tatgaataac cccgtctgtc      60
ttgatgactg gttgattggc tttaaaagct tgttgacagg ggtaaacgtt cggcaataat     120
tttctgccgc atgcgggtgt tgcataaaac gtgttacgtt cctttatcga caggtcaggt     180
caccgctcac ccgccgacga gaaagcaaca ctgacatgac aaagcaaaaa atagatgaat     240
aagttgagtt gtgcatatgt agcctgaccg tcacaaagta tatggtgtct gtaccagtaa     300
gatgatggcc ggactcttta aaaacgagct gacctgcaca atacaggatg acttagcaa      360
tggctgctcc tggcacaaag cggacagtga tcaccgttct tacgactact ttctgacttc     420
cttcgtgact tgccctaagc atgttgtagt rbmrnarbst artgcgatac ttgtaatgac     480
atttgtaatt acaagaggtg taagacatgg gtargcatta acctgcgtat tgacgatgaa     540
cttaaagcgc gttcttacgc cgcgcttgaa aaaatgggtg taactccttc tgaagcgctt     600
cgtctcatgc tcgagtatat cgctgacaat gaacgcttgc cgttcaaaca gacactcctg     660
agtgatgaag atgctgaact tgtggagata gtgaaagaac ggcttcgtaa tcctndrbst     720
artraagcca gtacgtgtga cgctggatga actctgatgg cgtatttctct ggattttgac     780
gagcgggcac taaggaatg gcgaaagctg ggctcgacgg tacgtgaaca gttgaaaaag     840
aagctggttg aagtacttga gtcaccccgg attgaagcaa acaagctccg tggtatgcct     900
gattgttaca agattaagct ccggtcttca ggctatcgcc ttgtatacca ggttatagac     960
gagaaagttg tcgttttcgt gatttctgtt gggaaaagag aacgctcgga agtatatagc    1020
gaggndrcgg tcaaacgcat tctctgaacc aaagcatgac atctctgttt cgcaccgsta    1080
rthkcraagg tgcacttcct gctttgcgtt gacaggagaa gcaggctatg aagcagcaaa    1140
aggcgatgtt aatcgccctg atcgtcatct gtttaaccgt catagtgacg gcactggtaa    1200
cgaggaaaga cctctgcgag gtacgaatcc gaaccgndhk caccagacgg aggtcgctgt    1260
cttcacagct tacgaacctg aggagtaaga gacccggcgg gggagaaatc cctcgccacc    1320
tctgatgtgg caggcatcct caacgcaccc gcacttaacc cgcttcggcg ggttttttgtt    1380
tttattttca arttcgcgtt tgaagttctg gacggtgccg aatagaatc aaaaatactt     1440
aagtdataba saccsnnumb r                                               1461
```

<210> SEQ ID NO 10
<211> LENGTH: 88
<212> TYPE: PRT
<213> ORGANISM: Methanococcus jannaschii

<400> SEQUENCE: 10

```
Met Lys Val Leu Phe Ala Lys Thr Phe Val Lys Asp Leu Lys His Val
  1               5                  10                  15

Pro Gly His Ile Arg Lys Arg Ile Lys Leu Ile Ile Glu Glu Cys Gln
             20                  25                  30

Asn Ser Asn Ser Leu Asn Asp Leu Lys Leu Asp Ile Lys Lys Ile Lys
         35                  40                  45

Gly Tyr His Asn Tyr Tyr Arg Ile Arg Val Gly Asn Tyr Arg Ile Gly
```

```
                50                  55                  60
Ile Glu Val Asn Gly Asp Thr Ile Ile Phe Arg Arg Val Leu His Arg
 65                  70                  75                  80

Lys Ser Ile Tyr Asp Tyr Phe Pro
                 85
```

<210> SEQ ID NO 11
<211> LENGTH: 91
<212> TYPE: PRT
<213> ORGANISM: Methanococcus jannaschii

<400> SEQUENCE: 11

```
Met Lys Gln Trp Lys Tyr Leu Leu Lys Lys Ser Phe Ile Lys Asp Leu
 1               5                  10                  15

Lys Glu Leu Pro Lys Asn Ile Gln Glu Lys Ile Lys Lys Leu Val Phe
                20                  25                  30

Glu Glu Ile Pro Asn Lys Asn Pro Pro Glu Ile Pro Asn Val Lys
            35                  40                  45

Lys Leu Lys Gly Ala Asp Ser Tyr Tyr Arg Ile Arg Val Gly Asp Tyr
 50                  55                  60

Arg Ile Gly Phe Lys Tyr Glu Asn Gly Lys Ile Val Phe Tyr Arg Val
 65                  70                  75                  80

Leu His Arg Lys Gln Ile Tyr Lys Arg Phe Pro
                85                  90
```

<210> SEQ ID NO 12
<211> LENGTH: 87
<212> TYPE: PRT
<213> ORGANISM: Archaeoglobus fulgidus

<400> SEQUENCE: 12

```
Met Phe Arg Val Val Val His Arg Lys Ala Thr Gln Glu Leu Lys Arg
 1               5                  10                  15

Leu Lys Lys Ala His Leu Lys Lys Phe Gly Val Leu Leu Glu Thr Leu
                20                  25                  30

Lys Thr Asp Pro Ile Pro Trp Lys Arg Phe Asp Val Lys Ile Glu
            35                  40                  45

Gly Glu Glu Asn Thr Tyr Arg Ile Arg Ile Gly Asp Phe Arg Val Ile
 50                  55                  60

Tyr Phe Leu Asp Lys Pro Thr Lys Thr Val His Ile Leu Lys Val Glu
 65                  70                  75                  80

Arg Arg Gly Lys Val Tyr Asp
                85
```

<210> SEQ ID NO 13
<211> LENGTH: 90
<212> TYPE: PRT
<213> ORGANISM: Methanococcus jannaschii

<400> SEQUENCE: 13

```
Met Lys Phe Asn Val Glu Ile His Lys Arg Val Leu Lys Asp Leu Lys
 1               5                  10                  15

Asp Leu Pro Pro Ser Asn Leu Lys Lys Phe Lys Glu Leu Ile Glu Thr
                20                  25                  30

Leu Lys Thr Asn Pro Ile Pro Lys Glu Lys Phe Asp Ile Lys Arg Leu
            35                  40                  45

Lys Gly Ser Asp Glu Val Tyr Arg Val Arg Ile Gly Lys Phe Arg Val
 50                  55                  60
```

-continued

```
Gln Tyr Val Val Leu Trp Asp Asp Arg Ile Ile Ile Ile Arg Lys Ile
65                  70                  75                  80

Ser Arg Arg Glu Gly Ala Tyr Lys Asn Pro
                85                  90

<210> SEQ ID NO 14
<211> LENGTH: 74
<212> TYPE: PRT
<213> ORGANISM: Bacillus theringiensis

<400> SEQUENCE: 14

Met Lys Phe Ile Ala Lys Gln Glu Lys Gly Ile Gln Lys Arg Ile Ala
 1               5                  10                  15

Glu Gly Leu Lys Gly Leu Leu Lys Ile Pro Pro Glu Gly Asp Ile Lys
            20                  25                  30

Ser Met Lys Gly Tyr Thr Glu Leu Tyr Arg Leu Arg Ile Gly Thr Phe
        35                  40                  45

Arg Ile Leu Phe Glu Ile Asn His Asp Glu Lys Val Ile Tyr Ile Gln
    50                  55                  60

Ala Ile Gly Asn Arg Gly Asp Ile Tyr Lys
65                  70

<210> SEQ ID NO 15
<211> LENGTH: 95
<212> TYPE: PRT
<213> ORGANISM: E. coli

<400> SEQUENCE: 15

Met Arg Tyr Gln Val Lys Phe Arg Glu Asp Ala Leu Lys Glu Trp Gln
 1               5                  10                  15

Lys Leu Asp Lys Ala Ile Gln Gln Gln Phe Ala Lys Lys Leu Lys Lys
            20                  25                  30

Cys Cys Asp Asn Pro His Ile Pro Ser Ala Lys Leu Arg Gly Ile Lys
        35                  40                  45

Asp Cys Tyr Lys Ile Lys Leu Arg Ala Ser Gly Phe Arg Leu Val Tyr
    50                  55                  60

Gln Val Ile Asp Glu Gln Leu Ile Ile Ala Val Val Ala Val Gly Lys
65                  70                  75                  80

Arg Glu Arg Ser Asp Val Tyr Asn Leu Ala Ser Glu Arg Met Arg
                85                  90                  95

<210> SEQ ID NO 16
<211> LENGTH: 95
<212> TYPE: PRT
<213> ORGANISM: E. coli

<400> SEQUENCE: 16

Met Ala Tyr Phe Leu Asp Phe Asp Glu Arg Ala Leu Lys Glu Trp Arg
 1               5                  10                  15

Lys Leu Gly Ser Thr Val Arg Glu Gln Leu Lys Lys Lys Leu Val Glu
            20                  25                  30

Val Leu Glu Ser Pro Arg Ile Glu Ala Asn Lys Leu Arg Gly Met Pro
        35                  40                  45

Asp Cys Tyr Lys Ile Lys Leu Arg Ser Ser Gly Tyr Arg Leu Val Tyr
    50                  55                  60

Gln Val Ile Asp Glu Lys Val Val Val Phe Val Ile Ser Val Gly Lys
65                  70                  75                  80
```

```
Arg Glu Arg Ser Glu Val Tyr Ser Glu Ala Val Lys Arg Ile Leu
                 85                  90                  95

<210> SEQ ID NO 17
<211> LENGTH: 96
<212> TYPE: PRT
<213> ORGANISM: Vibrio cholerae

<400> SEQUENCE: 17

Met Thr Tyr Lys Leu Glu Phe Lys Lys Ser Ala Leu Lys Glu Trp Lys
 1               5                  10                  15

Lys Leu Ala Val Pro Leu Gln Gln Phe Lys Lys Leu Ile Glu
                20                  25                  30

Arg Leu Glu Asn Pro His Val Pro Ser Ala Lys Leu Ser Gly Ala Glu
                35                  40                  45

Asn Ile Tyr Lys Ile Lys Leu Arg Gln Ser Gly Tyr Arg Leu Val Tyr
            50                  55                  60

Gln Val Glu Asn Asp Ile Ile Val Val Thr Val Leu Ala Val Gly Lys
 65                  70                  75                  80

Arg Glu Arg Ser Glu Val Tyr Thr Lys Ala Leu Gln Arg Leu Asp Asp
                 85                  90                  95

<210> SEQ ID NO 18
<211> LENGTH: 87
<212> TYPE: PRT
<213> ORGANISM: Mycibacterium tuberculosis

<400> SEQUENCE: 18

Met Pro Tyr Thr Val Arg Phe Thr Thr Thr Ala Arg Arg Asp Leu His
 1               5                  10                  15

Lys Leu Pro Pro Arg Ile Leu Ala Ala Val Val Glu Phe Ala Phe Gly
                20                  25                  30

Asp Leu Ser Arg Glu Pro Leu Arg Val Gly Lys Pro Leu Arg Arg Glu
                35                  40                  45

Leu Ala Gly Thr Phe Ser Ala Arg Arg Gly Thr Tyr Arg Leu Leu Tyr
            50                  55                  60

Arg Ile Asp Asp Glu His Thr Thr Val Val Ile Leu Arg Val Asp His
 65                  70                  75                  80

Arg Ala Asp Ile Tyr Arg Arg
                85

<210> SEQ ID NO 19
<211> LENGTH: 97
<212> TYPE: PRT
<213> ORGANISM: Mycobacterium tuberculosis

<400> SEQUENCE: 19

Met Ser Asp Asp His Pro Tyr His Val Ala Ile Thr Ala Thr Ala Ala
 1               5                  10                  15

Arg Asp Leu Gln Arg Leu Pro Glu Lys Ile Ala Ala Ala Cys Val Glu
                20                  25                  30

Phe Val Phe Gly Pro Leu Leu Asn Asn Pro His Arg Leu Gly Lys Pro
                35                  40                  45

Leu Arg Asn Asp Leu Glu Gly Leu His Ser Ala Arg Arg Gly Asp Tyr
            50                  55                  60

Arg Val Val Tyr Ala Ile Asp Asp Gly His His Arg Val Glu Ile Ile
 65                  70                  75                  80

His Ile Ala Arg Arg Ser Ala Ser Tyr Arg Met Asn Pro Cys Arg Pro
```

```
                85                  90                  95
Arg

<210> SEQ ID NO 20
<211> LENGTH: 102
<212> TYPE: PRT
<213> ORGANISM: Haemophilus influenzae

<400> SEQUENCE: 20

Met Ser Glu Glu Lys Pro Leu Lys Val Ser Tyr Ser Lys Gln Phe Val
1               5                   10                  15

Arg Asp Leu Thr Asp Leu Ala Lys Arg Ser Pro Asn Val Leu Ile Gly
                20                  25                  30

Ser Lys Tyr Ile Thr Ala Ile His Cys Leu Leu Asn Arg Leu Pro Leu
            35                  40                  45

Pro Glu Asn Tyr Gln Asp His Ala Leu Val Gly Glu Trp Lys Gly Tyr
        50                  55                  60

Arg Asp Cys His Ile Gln Gly Asp Leu Val Leu Ile Tyr Gln Tyr Val
65                  70                  75                  80

Ile Gln Asp Glu Phe Asp Glu Leu Lys Phe Ser Arg Leu Asn Ile His
                85                  90                  95

Ser Gln Thr Ala Leu Lys
            100

<210> SEQ ID NO 21
<211> LENGTH: 92
<212> TYPE: PRT
<213> ORGANISM: E. coli

<400> SEQUENCE: 21

Met Ile Gln Arg Asp Ile Glu Tyr Ser Gly Gln Tyr Ser Lys Asp Val
1               5                   10                  15

Lys Leu Ala Gln Lys Arg His Lys Asp Met Asn Lys Leu Lys Tyr Leu
                20                  25                  30

Met Thr Leu Leu Ile Asn Asn Thr Leu Pro Leu Pro Ala Val Tyr Lys
            35                  40                  45

Asp His Pro Leu Gln Gly Ser Trp Lys Gly Tyr Arg Asp Ala His Val
        50                  55                  60

Glu Pro Asp Trp Ile Leu Ile Tyr Lys Leu Thr Asp Lys Leu Leu Arg
65                  70                  75                  80

Phe Glu Arg Thr Gly Thr His Ala Ala Leu Phe Gly
                85                  90

<210> SEQ ID NO 22
<211> LENGTH: 88
<212> TYPE: PRT
<213> ORGANISM: Helicobacter pylori

<400> SEQUENCE: 22

Met Leu Lys Leu Asn Leu Lys Lys Ser Phe Gln Lys Asp Phe Asp Lys
1               5                   10                  15

Leu Leu Leu Asn Gly Phe Asp Asp Ser Val Leu Asn Glu Val Ile Leu
                20                  25                  30

Thr Leu Arg Lys Lys Glu Pro Leu Asp Pro Gln Phe Gln Asp His Ala
            35                  40                  45

Leu Lys Gly Lys Trp Lys Pro Tyr Arg Glu Cys His Ile Lys Pro Asp
        50                  55                  60
```

Val Leu Leu Val Tyr Leu Val Lys Asp Asp Glu Leu Ile Leu Arg
65                  70                  75                  80

Leu Gly Ser His Ser Glu Leu Phe
                85

<210> SEQ ID NO 23
<211> LENGTH: 92
<212> TYPE: PRT
<213> ORGANISM: Archeoglobus fulgidus

<400> SEQUENCE: 23

Met Ala Trp Lys Val Arg Tyr His Lys Lys Ala Ile Lys Phe Leu Glu
1               5                   10                  15

Lys Leu Asp Glu Gly Lys Arg Ser Ile Leu Leu Ser Lys Ile Gln Glu
                20                  25                  30

Leu Val Asn Ser Leu Glu Ser Gly Val Leu Pro Ile Gln Arg Met Asp
            35                  40                  45

Ile Lys Arg Leu Lys Gly Val Trp Asp Gly Phe Leu Arg Leu Arg Val
50                  55                  60

Gly Glu Val Arg Ile Ile Phe Lys Ile Asn Val Glu Asp Glu Thr Ile
65                  70                  75                  80

Phe Ile Tyr Ser Ile His Phe Arg Glu Lys Val Tyr
                85                  90

<210> SEQ ID NO 24
<211> LENGTH: 86
<212> TYPE: PRT
<213> ORGANISM: Archeoglobus fulgidus

<400> SEQUENCE: 24

Met Asn Glu Val Leu Ile His Lys Lys Phe Leu Asp Gly Leu Asp Ser
1               5                   10                  15

Gly Arg Arg Ser Lys Val Leu Asp Ala Ile Arg Met Leu Lys Asp Phe
                20                  25                  30

Pro Ile Ile Arg Ala Asp Ile Lys Lys Ile Gly Pro Lys Thr Tyr Arg
            35                  40                  45

Leu Arg Lys Gly Glu Ile Arg Ile Ile Phe Asp Phe Asp Ile Gly Thr
50                  55                  60

Asn Arg Val Phe Val Lys Phe Ala Ala Ser Glu Gly Val Phe Thr Lys
65                  70                  75                  80

Thr Glu Glu Lys Phe Phe
                85

<210> SEQ ID NO 25
<211> LENGTH: 85
<212> TYPE: PRT
<213> ORGANISM: Archeoglobus fulgidus

<400> SEQUENCE: 25

Met Asn Tyr Lys Ala Gln Phe Ser Glu Glu Phe Leu Lys Ile Ala Lys
1               5                   10                  15

Lys Leu Lys Glu Lys Asp Pro Glu Leu Leu Arg Leu Gln Ser Lys
                20                  25                  30

Val Glu Glu Ile Ile Lys Gln Pro Glu His Tyr Lys Pro Leu Arg Gly
            35                  40                  45

Gln Met Lys Gly Leu Arg Arg Ala His Val Gly Lys Phe Val Ile Ile
50                  55                  60

Phe Lys Val Glu Glu Asp Thr Val Lys Phe Val Thr Phe Lys His His

```
                65                  70                  75                  80
Asn His Ala Tyr Lys
                85

<210> SEQ ID NO 26
<211> LENGTH: 120
<212> TYPE: PRT
<213> ORGANISM: Synechosystis species

<400> SEQUENCE: 26

Met Ser Asn Asn Leu His Leu Val Asn Ile Asp Phe Thr Pro Glu Tyr
1               5                   10                  15

Arg Arg Ser Leu Lys Tyr Leu Ala Lys Lys Tyr Arg Asn Ile Arg Ser
            20                  25                  30

Asp Val Gln Pro Ile Ile Glu Ala Leu Gln Lys Gly Val Ile Ser Gly
        35                  40                  45

Asp Arg Leu Ala Gly Phe Gly Ser Asp Ile Tyr Val Tyr Lys Leu Arg
    50                  55                  60

Ile Lys Asn Ser Asn Ile Gln Lys Gly Lys Ser Ser Gly Tyr Arg Leu
65                  70                  75                  80

Ile Tyr Leu Leu Glu Ser Glu Asn Ser Ile Leu Leu Thr Ile Tyr
                85                  90                  95

Ser Lys Ala Glu Gln Glu Asp Ile Ala Ala Ser Asp Ile Asn Ser Ile
                100                 105                 110

Leu Gly Glu Tyr Ser Ile Glu Asp
        115                 120

<210> SEQ ID NO 27
<211> LENGTH: 86
<212> TYPE: PRT
<213> ORGANISM: E. coli

<400> SEQUENCE: 27

Met Ala Ala Asn Ala Phe Val Arg Ala Arg Ile Asp Glu Asp Leu Lys
1               5                   10                  15

Asn Gln Ala Ala Asp Val Leu Ala Gly Met Gly Leu Thr Ile Ser Asp
            20                  25                  30

Leu Val Arg Ile Thr Leu Thr Lys Val Ala Arg Glu Lys Ala Leu Pro
        35                  40                  45

Phe Asp Leu Arg Glu Pro Asn Gln Leu Thr Ile Gln Ser Ile Lys Asn
    50                  55                  60

Ser Glu Ala Gly Ile Asp Val His Lys Ala Lys Asp Ala Asp Leu
65                  70                  75                  80

Phe Asp Lys Leu Gly Ile
                85

<210> SEQ ID NO 28
<211> LENGTH: 82
<212> TYPE: PRT
<213> ORGANISM: Vibrio cholerae

<400> SEQUENCE: 28

Met Thr Thr Arg Ile Leu Ala Asp Val Ala Ala Ser Ile Thr Glu Phe
1               5                   10                  15

Lys Ala Asn Pro Met Lys Val Ala Thr Ser Ala Phe Gly Ala Pro Val
            20                  25                  30

Ala Val Leu Asn Arg Asn Glu Pro Ala Phe Tyr Cys Val Pro Ala Ser
        35                  40                  45
```

```
Thr Tyr Glu Ile Met Met Asp Lys Leu Glu Asp Leu Glu Leu Leu Ala
 50                  55                  60

Ile Ala Lys Glu Arg Leu Ser Glu Asp Ser Val Ser Val Asn Ile Asp
 65                  70                  75                  80

Asp Leu

<210> SEQ ID NO 29
<211> LENGTH: 83
<212> TYPE: PRT
<213> ORGANISM: Bacillus thurigiensis

<400> SEQUENCE: 29

Met Pro Asn Ile Ile Leu Ser Asp Thr Ser Ala Ser Val Ser Glu Leu
  1               5                  10                  15

Lys Lys Asn Pro Met Ala Thr Val Ser Ala Gly Asp Gly Phe Pro Val
                 20                  25                  30

Ala Ile Leu Asn Arg Asn Gln Pro Ala Phe Tyr Cys Val Pro Ala Glu
             35                  40                  45

Leu Tyr Glu Lys Met Leu Asp Ala Leu Asp Asp Gln Glu Leu Val Lys
 50                  55                  60

Leu Val Ala Glu Arg Ser Asn Gln Pro Leu His Asp Val Asp Leu Asp
 65                  70                  75                  80

Lys Tyr Leu

<210> SEQ ID NO 30
<211> LENGTH: 93
<212> TYPE: PRT
<213> ORGANISM: Mycobacterium tuberculosis

<400> SEQUENCE: 30

Met Arg Ile Leu Pro Ile Ser Thr Ile Lys Gly Lys Leu Asn Glu Phe
  1               5                  10                  15

Val Asp Ala Val Ser Ser Thr Gln Asp Gln Ile Thr Ile Thr Lys Asn
                 20                  25                  30

Gly Ala Pro Ala Ala Val Leu Val Gly Ala Asp Glu Trp Glu Ser Leu
             35                  40                  45

Gln Glu Thr Leu Tyr Trp Leu Ala Gln Pro Gly Ile Arg Glu Ser Ile
 50                  55                  60

Ala Glu Ala Asp Ala Asp Ile Ala Ser Gly Arg Thr Tyr Gly Glu Asp
 65                  70                  75                  80

Glu Ile Arg Ala Glu Phe Gly Val Pro Arg Arg Pro His
                 85                  90

<210> SEQ ID NO 31
<211> LENGTH: 89
<212> TYPE: PRT
<213> ORGANISM: Mycobacterium tuberculosis

<400> SEQUENCE: 31

Met Ala Val Val Pro Leu Gly Glu Val Arg Asn Arg Leu Ser Glu Tyr
  1               5                  10                  15

Val Ala Glu Val Glu Leu Thr His Glu Arg Ile Thr Ile Thr Arg His
                 20                  25                  30

Gly His Pro Ala Ala Val Leu Ile Ser Ala Asp Asp Leu Ala Ser Ile
             35                  40                  45

Glu Glu Thr Leu Glu Val Leu Arg Thr Pro Gly Ala Ser Glu Ala Ile
 50                  55                  60
```

```
Arg Glu Gly Leu Ala Asp Val Ala Ala Gly Arg Phe Val Ser Asn Asp
 65                  70                  75                  80

Glu Ile Arg Asn Arg Tyr Thr Ala Arg
                 85
```

<210> SEQ ID NO 32
<211> LENGTH: 97
<212> TYPE: PRT
<213> ORGANISM: E. coli

<400> SEQUENCE: 32

```
Met His Arg Ile Leu Ala Glu Lys Ser Val Asn Ile Thr Glu Leu Arg
  1               5                  10                  15

Lys Asn Pro Ala Lys Tyr Phe Ile Asp Gln Pro Val Ala Val Leu Ser
                 20                  25                  30

Asn Asn Arg Pro Ala Gly Tyr Leu Leu Ser Ala Ser Ala Phe Glu Ala
             35                  40                  45

Leu Met Asp Met Leu Ala Glu Gln Glu Glu Lys Lys Pro Ile Lys Ala
 50                  55                  60

Arg Phe Arg Pro Ser Ala Ala Arg Leu Glu Ile Thr Arg Arg Ala
 65                  70                  75                  80

Glu Gln Tyr Leu Asn Asp Met Thr Asp Asp Phe Asn Asp Phe Lys
                 85                  90                  95

Glu
```

<210> SEQ ID NO 33
<211> LENGTH: 68
<212> TYPE: PRT
<213> ORGANISM: Salmonella typhimurium

<400> SEQUENCE: 33

```
Met Phe Met Arg Thr Val Asn Tyr Ser Glu Ala Arg Gln Asn Leu Ala
  1               5                  10                  15

Glu Val Leu Glu Ser Ala Val Thr Gly Gly Pro Val Thr Ile Thr Arg
                 20                  25                  30

Arg Gly His Lys Ser Ala Val Ile Ile Ser Ala Glu Glu Phe Glu Arg
             35                  40                  45

Tyr Gln Thr Ala Arg Met Asp Asp Glu Phe Ala Ala Ile Met Ala Val
 50                  55                  60

His Gly Asn Glu
 65
```

<210> SEQ ID NO 34
<211> LENGTH: 79
<212> TYPE: PRT
<213> ORGANISM: E. coli

<400> SEQUENCE: 34

```
Met Gly Ser Ile Asn Leu Arg Ile Asp Asp Glu Leu Lys Ala Arg Ser
  1               5                  10                  15

Tyr Ala Ala Leu Glu Lys Met Gly Val Thr Pro Ser Glu Ala Leu Arg
                 20                  25                  30

Leu Met Leu Glu Tyr Ile Ala Asp Asn Glu Arg Leu Pro Phe Lys Gln
             35                  40                  45

Thr Leu Leu Ser Asp Glu Asp Ala Glu Leu Val Glu Ile Val Lys Glu
 50                  55                  60

Arg Leu Arg Asn Pro Lys Pro Val Arg Val Thr Leu Asp Glu Leu
```

```
                                      65                  70                  75

<210> SEQ ID NO 35
<211> LENGTH: 98
<212> TYPE: PRT
<213> ORGANISM: Haemophilus influenzae

<400> SEQUENCE: 35

Met Ala Leu Thr Asn Ser Ser Ile Ser Phe Arg Thr Val Glu Lys Thr
 1               5                  10                  15

Lys Leu Glu Ala Tyr Gln Val Ile Glu Gln Tyr Gly Leu Thr Pro Ser
            20                  25                  30

Gln Val Phe Asn Met Phe Leu Ala Gln Ile Ala Lys Thr Arg Ser Ile
        35                  40                  45

Pro Val Asp Leu Asn Tyr Leu Arg Pro Asn Lys Glu Thr Leu Ala Ala
    50                  55                  60

Ile Asp Glu Leu Asp Ser Gly Asn Ala Glu Ser Phe Phe Ile Glu Ala
65                  70                  75                  80

Ser Glu Asn Tyr Ser Ala Glu Glu Phe Thr Lys Arg Ile Leu Asn Gly
                85                  90                  95

Gly Gln

<210> SEQ ID NO 36
<211> LENGTH: 82
<212> TYPE: PRT
<213> ORGANISM: Methanococcus jannaschii

<400> SEQUENCE: 36

Met Leu Asn Ile Asn Lys Glu Ile Ala Gln Ile Glu Thr Glu Leu Asn
 1               5                  10                  15

Glu Leu Lys Lys Leu Arg Asp Glu Ile Ser Glu Arg Ile Glu Lys Leu
            20                  25                  30

Glu Ile Lys Leu Leu Lys Leu Lys Ala Leu Ala Ile Pro Glu Glu Glu
        35                  40                  45

Phe Glu Glu Asp Tyr Glu Glu Ile Ile Glu Asp Val Lys Lys Ser Leu
    50                  55                  60

Asp Lys Lys Glu Thr Val Pro Ala Glu Glu Ala Leu Lys Glu Leu Gly
65                  70                  75                  80

Leu Leu

<210> SEQ ID NO 37
<211> LENGTH: 65
<212> TYPE: PRT
<213> ORGANISM: Archaeoglobus fulgidus

<400> SEQUENCE: 37

Met Asn Glu Ala Leu Leu Arg Glu Ile Tyr Ser Glu Val Lys Lys Ile
 1               5                  10                  15

Arg Glu Lys Ile Glu Gln Leu Glu Glu Leu Ile Ile Pro Ala Glu Lys
            20                  25                  30

Val Ser Glu Glu Glu Leu Leu Glu Ile Arg Lys Leu Lys Glu Glu Ser
        35                  40                  45

Leu Lys Gly Glu His Val Asp Trp Asp Glu Leu Lys Arg Glu Leu Gly
    50                  55                  60

Val
65
```

<210> SEQ ID NO 38
<211> LENGTH: 72
<212> TYPE: PRT
<213> ORGANISM: Archaeoglobus fulgidus

<400> SEQUENCE: 38

Met Lys Val Leu Leu Asp Ile Ile Glu Asp Ile Glu Asn Phe Ile Arg
1               5                   10                  15

Gln Leu Glu Lys Arg Arg Gly Glu Leu Glu Leu Lys Asp Glu Ile
            20                  25                  30

Leu Ile Phe Ser Asp Ala Glu Phe Ile Asp Ser Ile Gln Arg Gly Leu
        35                  40                  45

Ser Asp Leu Glu Gln Gly Arg Ser Lys Val Cys Ser Asn Leu Glu Glu
    50                  55                  60

Val Lys Lys Leu Phe Glu Asp Ile
65                  70

<210> SEQ ID NO 39
<211> LENGTH: 62
<212> TYPE: PRT
<213> ORGANISM: Archaeoglobus fulgidus

<400> SEQUENCE: 39

Met Glu Val Ile Gln Ile Ser Lys Asp Glu Leu Glu Glu Ile Ile Glu
1               5                   10                  15

Arg Lys Phe Lys Glu Val Leu Ile Lys Ala Leu Met Glu Ile Thr Pro
            20                  25                  30

Tyr Val Ser Asp Glu Glu Gln Glu Glu Ile Asp Lys Ile Ala Gly Lys
        35                  40                  45

Pro Asp Glu Tyr Glu Gly Glu Phe Glu Glu Trp His Gly Lys
    50                  55                  60

<210> SEQ ID NO 40
<211> LENGTH: 57
<212> TYPE: PRT
<213> ORGANISM: Archeoglobus fulgidus

<400> SEQUENCE: 40

Met Asp Ile Gln Val Ile Lys Gln Ala Val Arg Glu Val Leu Arg Glu
1               5                   10                  15

Glu Leu Pro Ser Ile Leu Lys Glu Val Ile Leu Ser Thr Ile Pro Pro
            20                  25                  30

Asp Glu Pro Glu Ala Asp Glu Lys Gln Phe Val Asp Glu Ile Asn
        35                  40                  45

Glu Asp Asp Tyr Val Lys Phe Asp Glu
    50                  55

<210> SEQ ID NO 41
<211> LENGTH: 95
<212> TYPE: PRT
<213> ORGANISM: Helicobacter pyloris

<400> SEQUENCE: 41

Met Pro Asn Thr Thr Asn Lys Asp Tyr Thr Lys Tyr Ser Gln Arg Gln
1               5                   10                  15

Leu Phe Ser Phe Leu Asn Ser Ile Lys Thr Lys Gln Lys Arg Ala Leu
            20                  25                  30

Glu Lys Leu Lys Glu Ile Gln Ala Gln Lys Gln Arg Ile Lys Lys Ala
        35                  40                  45

-continued

```
Leu Gln Phe Lys Ala Leu Asn Leu Thr Glu Asn Gly Tyr Thr Ile Glu
    50                  55                  60
Glu Glu Arg Glu Ile Leu Ala Arg Ala Lys Asp Thr Lys Asn Arg Leu
65                  70                  75                  80
Cys Phe Lys Ser Ile Glu Asp Phe Lys Lys His Cys Glu Asn Leu
                85                  90                  95

<210> SEQ ID NO 42
<211> LENGTH: 86
<212> TYPE: PRT
<213> ORGANISM: Synechosystis species

<400> SEQUENCE: 42

Met Met Arg Ala Phe Glu Val Met Ala Thr Val Lys Asp Ser Lys Gln
 1               5                  10                  15

Leu Leu Leu Asp Ser Asp Leu His Trp Asn Thr Ser Arg Val Lys Val
            20                  25                  30

Ile Ile Leu Glu Ser Asp Glu Leu Ala Ser Lys Gly Ser Glu Phe Asp
        35                  40                  45

Pro Asp Asp Thr Pro Val Glu Glu Ile Lys Val Ser Leu Arg Lys Ala
    50                  55                  60
Leu Glu Glu Tyr Lys Gln Gly Lys Arg Ile Pro Val Glu Asn Met Trp
65                  70                  75                  80
Glu Gly Ile Asp Val Glu
                85

<210> SEQ ID NO 43
<211> LENGTH: 85
<212> TYPE: PRT
<213> ORGANISM: Bacillus thurigiensis

<400> SEQUENCE: 43

Met Ala Ile Arg Lys Asp Glu Leu Tyr Arg Leu Ile Asp His Leu Asp
 1               5                  10                  15

Gln Gln Asp Glu Lys Ala Ala Phe Asp Phe Leu Glu Phe Leu Val Gln
            20                  25                  30

Arg Ser Arg Arg Lys Pro Lys Glu Trp Glu Lys Ile Asp Met Ala Asp
        35                  40                  45

Pro Asp His Glu Pro Leu Ser Thr Gln Glu Leu Glu Gln Leu Asn Ser
    50                  55                  60

Glu Glu Gly Tyr Val Ser Gly Glu Asp Ala Lys Arg Glu Phe Gly Leu
65                  70                  75                  80

Gln Ile Asp Leu Pro
                85

<210> SEQ ID NO 44
<211> LENGTH: 1280
<212> TYPE: DNA
<213> ORGANISM: E. coli
<220> FEATURE:
<221> NAME/KEY: unsure
<222> LOCATION: 505,818, 1078
<223> OTHER INFORMATION: n = A,T,C or G

<400> SEQUENCE: 44
gagtatcata ttaggatacg ggtgggtgac gcccacctct ggcatagaac ggacattcat      60
tgatgccatg ccagaatgga cgttcaggtt attccgtcca gttctgctgg caacgcgaga     120
tctcccctgg tatagtgatg ccacagcaaa gcgctcaaac agggataata tgatggaaat     180
```

-continued

```
caaggctcaa cagttttgtc acatcaacgg ggcggcaagt ccttactgac aacggacaac      240
aaggtatggg cggcgtggcg ggtatcggtt ccacgactga aaagcatcag gggcgcgtgg      300
cggaagcgat ttttgcgaac tgcgcggaac tggataacga ccagcttaac gagatcatcg      360
agtgggttcg gctctatcag cgctgaatgc cactatcagg ctgcgcaagc ggcctttttt      420
acgccccttg tttaattccc gcactacctg gacgttcagg tgattctgtc catctgtaca      480
aaaaacaata aaagacttgt rbmrnataac aggtcatgta aggagtatct ttgagactgg      540
ttaaacagtc ttgaaasdst artrbggtgg cctatgccta acattattct cagtgataca      600
agcgccagtg tcagcgagct gaagaaaaac ccgatggcga cagtcagcgc cggtgatggt      660
ttcccggtcg ctatcctgaa ccgtaatcag cctgctttct actgtgtacc cgcagagctg      720
tacgaaaaga tgcttgatgc cctagacgat caggagttgg ttaaasdctg gtagccgaac      780
gcagcaacca accgctgcat gatgtagatc tggataandr bstartrata cctatgaggt      840
atcaggtaaa attcagggaa gatgcgctga agagtggca aaaactggac aaggctattc      900
agcaacagtt tgcgaaaaag ctaaaaaagt gctgtgacaa tccgcatatt ccttccgcaa      960
aactgcgtgg gataaaggac tgctacaaaa taaaattacg tgcgtcaggt tttcgcctgg     1020
tctatcaggt gattgacgaa caattaatta tcgctgttgt agctgtgggt aaacgtgndr     1080
agcgcagtga cgtttataat cttgccagcg aaagaatgag ataaaagcaa taaacacaga     1140
aagttactct ggcgttatgg ggtaatgcaa agtatgagtc gtagagggaa ttgcctggat     1200
aattcgccga tggaaagagt cttttcgcagc cttaaaagtg aatggcttcc gaaaggtggt     1260
tatggtgatt ttagccatgc                                                1280
```

<210> SEQ ID NO 45
<211> LENGTH: 1168
<212> TYPE: DNA
<213> ORGANISM: Bacillus thuringiensis
<220> FEATURE:
<221> NAME/KEY: unsure
<222> LOCATION: 407, 769, 1029
<223> OTHER INFORMATION: n = A,T,C or G

<400> SEQUENCE: 45

```
ctcgtttttt ctgttggtac aaacttaatt gattttgaat aatttgtttg taccagtcct       60
ttttgcttag cccagtcaaa ataacgtttg attgaattaa tgcgccggtt aatcgtagaa      120
ggttttagta atcttgtaac ttgcatatgc cctcgatatc gagcaatagt gcgagcggta      180
acttctattg gatgaaaaag agtatcctca gcatgttttc cccacacatt ttcaaaccaa      240
aatacaaaat cttttaaatc actcgtatat tcttttagtg tttttgtatg caaatctcct      300
tcttgagata agctagaaat aaaatcggaa atcaaagatg ttgcttgtat agaaattgtt      360
ttagtggaat gcataaatac ctcctctttt attgacttac rbbtmrnaat tagcggacat      420
gatattttaa tcttatcaat tatgttagcg gacatcaaac atttattttc ccacacttca      480
tgtccactaa tattaattag tggacattrs dstartrbta aaactatctc gaaagtaggt      540
gtaacacatg gctattcgta aagatgaatt gtatcggtta attgatcacc tggatcaaca      600
agatgaaaaa gcagcatttg acttttttaga atttcttgtt caacggtcaa gaagaaaacc      660
taaagaatgg gaaaaaattg atatggcaga tcctgatcat gaaccgctgt ctacacaaga      720
gttagaacag ttaaacagtg aagaaggata tgtatcaggg gaggacgcnd rbstartraa      780
aacgtgaatt cggactacaa attgattac cataagtccg cggtgaaatt tattgcaaag      840
caagaaaaag ggattcaaaa aagaattgca gaaggattga agggacttct taagattcct      900
```

```
cctgaaggag atattaaaag tatgaaaggt tacacagaac tatatcgatt acggattgga      960
acctttcgaa ttttatttga aataaatcat gatgagaaag tcatatacat acaagcaatt     1020
ggaaatcgnd rtggtgacat ctataaataa ggcaaacatg cattttaaa agaaaggtct     1080 tctgaatcga agaaccttcc ttttttgtgt gcgaataatg tccgctaatg cttgttgcgt     1140
gattctgttc cattgctaca catacccc                                       1168
```

```
<210> SEQ ID NO 46
<211> LENGTH: 1024
<212> TYPE: DNA
<213> ORGANISM: Methanococcus jannaschii
<220> FEATURE:
<221> NAME/KEY: unsure
<222> LOCATION: 609, 871
<223> OTHER INFORMATION: n = A,T,C or G

<400> SEQUENCE: 46
```

```
ccgataccgt tgctggagac atagctggag ctttgaaggc ggagaagctt attttaataa       60
cagatgttga tggaataatg gatgatataa ataatccaga gacgttgcat agaaaattaa      120
cagcttcaga actaaaagaa atgatagaag atggaagaat aaagggaggg atgattccaa      180
aggctgaaag tgccttatat gccttagagc atggagttaa gagcgttcat ataataaatg      240
gaaagattcc tcatgctttg ttgttggaga tatttacaga ggagggtatt gggacgatga      300
taacaagaga ttaaagtttt tatattataa actacttaag aattaaaata startrbmag     360
acaaataagg ggataactat gctcaatata acaaagaga tagcacaaat agaaactgaa       420
ttgaatgaat tgaaaaaatt gagagatgaa atctctgaaa ggattgaaaa attagaaata      480
aagttattaa aattgaaagc attagctatt ccagaggagg aatttgaaga ggattatgaa      540
gaaattatag aagatgttaa aaaatctctg ataaaaaag agactgtgcc agcagaagag       600
gctttgaand rbmstartrm agaattggga ttattatgaa gtttaacgtt gagatacata     660
aaagagtctt aaaagattta aaggatttgc ctccctcaaa cttaaagaag tttaaagaac      720
taatagaaac attaaaaacc aatcccattc caaaagaaaa atttgatatt aaaagattaa      780
aaggcagtga tgaggtttat agagttagaa ttggaaaatt tagagttcaa tatgttgttt      840
tatgggatga tagaataata ataattgaaa ndrmagataa gtagaagaga aggagcttat      900
aaaaatccct aagctattaa aaattctaat ggctacattt ttatatctct tttcttaatt      960
caaatagaaa aaacagattc ggctgatacc atgattattc ttttagattt aaatggaaca     1020
atag                                                                 1024
```

```
<210> SEQ ID NO 47
<211> LENGTH: 28
<212> TYPE: DNA
<213> ORGANISM: Artificial Sequence
<220> FEATURE:
<223> OTHER INFORMATION: Primer

<400> SEQUENCE: 47
cccccgaatt cgcatgcgcc attagaat                                         28
```

```
<210> SEQ ID NO 48
<211> LENGTH: 37
<212> TYPE: DNA
<213> ORGANISM: Artificial Sequence
<220> FEATURE:
<223> OTHER INFORMATION: Primer
```

```
<400> SEQUENCE: 48
cccccggatc cgagctcgag gctttgaaag aattggg                               37

<210> SEQ ID NO 49
<211> LENGTH: 38
<212> TYPE: DNA
<213> ORGANISM: Artificial Sequence
<220> FEATURE:
<223> OTHER INFORMATION: Primer

<400> SEQUENCE: 49
ccccggatcc gtcgacgaca ataaggggga taactatg                             38

<210> SEQ ID NO 50
<211> LENGTH: 32
<212> TYPE: DNA
<213> ORGANISM: Artificial Sequence
<220> FEATURE:
<223> OTHER INFORMATION: Primer

<400> SEQUENCE: 50
ccccggatcc gatgcatgat ttaggcttga ag                                   32

<210> SEQ ID NO 51
<211> LENGTH: 34
<212> TYPE: DNA
<213> ORGANISM: Artificial Sequence
<220> FEATURE:
<223> OTHER INFORMATION: Primer

<400> SEQUENCE: 51
ccccgaattc gaatgaaaat ttacttgaaa aaag                                 34

<210> SEQ ID NO 52
<211> LENGTH: 58
<212> TYPE: DNA
<213> ORGANISM: Artificial Sequence
<220> FEATURE:
<223> OTHER INFORMATION: Primer

<400> SEQUENCE: 52
tgtaatacga ctcactatag ataaggagtt ttataaatgg cgtattttct ggattttg       58

<210> SEQ ID NO 53
<211> LENGTH: 19
<212> TYPE: DNA
<213> ORGANISM: Artificial Sequence
<220> FEATURE:
<223> OTHER INFORMATION: Primer

<400> SEQUENCE: 53
caccttcggt gcgaaacag                                                  19

<210> SEQ ID NO 54
<211> LENGTH: 58
<212> TYPE: DNA
<213> ORGANISM: Artificial Sequence
<220> FEATURE:
<223> OTHER INFORMATION: Primer

<400> SEQUENCE: 54
tgtaatacga ctcactatag ataaggagtt ttataaatga ggtatcaggt aaaattca       58

<210> SEQ ID NO 55
<211> LENGTH: 20
```

```
-continued

<212> TYPE: DNA
<213> ORGANISM: Arificial sequence
<220> FEATURE:
<223> OTHER INFORMATION: Primer

<400> SEQUENCE: 55
ctttccatcg gcgaattatc                                              20

<210> SEQ ID NO 56
<211> LENGTH: 58
<212> TYPE: DNA
<213> ORGANISM: Artificial Sequence
<220> FEATURE:
<223> OTHER INFORMATION: Primer

<400> SEQUENCE: 56
tgtaatacga ctcactatag ataaggagtt ttataaatga agtttaacgt tgagatac    58

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
atcatggtat cagccgaatc                                              20

<210> SEQ ID NO 58
<211> LENGTH: 24
<212> TYPE: DNA
<213> ORGANISM: Artificial Sequence
<220> FEATURE:
<223> OTHER INFORMATION: Primer

<400> SEQUENCE: 58
taggtaccat ggcgtatttt ctgg                                         24

<210> SEQ ID NO 59
<211> LENGTH: 23
<212> TYPE: DNA
<213> ORGANISM: Artificial Sequence
<220> FEATURE:
<223> OTHER INFORMATION: Primer

<400> SEQUENCE: 59
gagaccccac actaccatcg gcg                                          23
```

CYTOTOXIN-BASED BIOLOGICAL CONTAINMENT

CROSS-REFERENCE TO RELATED APPLICATIONS

This application is a division of U.S. patent application Ser. No. 11/558,856, entitled CYTOTOXIN-BASED BIOLOGICAL CONTAINMENT, filed Nov. 10, 2006, which is a division of U.S. patent application Ser. No. 09/700,130, entitled CYTOTOXIN-BASED BIOLOGICAL CONTAINMENT, having a §371 date of Dec. 18, 2001, now U.S. Pat. No. 7,183,097, issued Feb. 27, 2007, which is the U.S. National Phase under 35 U.S.C. §371 of International Application No. PCT/DK99/00258, filed May 7, 1999, which claims priority to Danish Application DK 0627/98 filed May 7, 1998 and U.S. Provisional Patent Application No. 60/085,067, filed May 12, 1998. The disclosure of U.S. patent application Ser. Nos. 11/558,856 and 09/700,130 are incorporated herein by reference in their entireties.

SEQUENCE LISTING

The present application is being filed along with a Sequence Listing in electronic format. The Sequence Listing is provided as a file entitled VANM247-001DV1C-SEQ. TXT, created Aug. 9, 2007, which is 35 Kb in size. The information in the electronic format of the Sequence Listing is incorporated herein by reference in its entirety.

FIELD OF THE INVENTION

The present invention relates to the field of biologically containing genetically modified microorganisms in a particular environment and vectors to a particular host cell. Specifically, there is provided recombinant vectors and cells containing a proteic killer system based on the E. coli RelE polypeptide and functional equivalents of this cytotoxin and method of containing replicons and cells, respectively to particular host cells or particular environments, respectively.

TECHNICAL BACKGROUND AND PRIOR ART

The increasing application of recombinant DNA technology to engineer novel microorganism which are industrially useful have caused concerns in the general public over the potential risks involved. These concerns are primarily related to the potential harm to humans and to undesirable and/or uncontrollable ecological consequences upon deliberate or unintentional release of such genetically engineered microorganisms (GEMs) into the environment. These concerns have led to the establishment of official guidelines for the safe handling of GEMs in laboratories and production facilities where such organisms are applied. Up till now, such guidelines have primarily been directed to measures of physically containing GEMs in laboratories and production facilities with the aim of reducing the likelihood that workers in such facilities were contaminated, or that the GEMs were to escape from their primary physical environment, such as a fermentation vessel.

It is presently being recognized that the level of safety in the handling of GEMs can be increased by combining physical containment measures with biological containment measures to reduce the possibility of the survival of the genetically engineered organisms if they were to escape from their primary environment.

Lately, however, concerns have become increasingly focused on potential risks related to deliberate release of GEMs to the outer environment and to the use of GEMs as live vaccines. In this connection there is a strongly felt need to have biological containment systems which subsequent to the environmental release of the GEMs or their administration as vaccines to a human or an animal body, effectively kill the released organisms in a controlled manner or which limit the function of the released GEMs to an extent where such GEMs are placed at a significant competitive disadvantage whereby they will eventually be ousted by the natural microflora of the environment to which they are released.

The first systems of biological containment were based on the use of "safe" cloning vectors and debilitated host bacteria. As examples, it has been suggested to select vectors which lack transfer functions or which naturally have a very narrow host range. Examples of debilitated host bacteria are E. coli mutants having an obligate requirement for exogenous nutrients not present or present in low concentrations outside the primary environment of the GEMs.

Other suggested biological containment systems have been based on mechanisms whereby the vector is restricted to the GEMs e.g. by using a plasmid vector with a nonsense mutation in a gene, the expression of which is indispensable for plasmid replication or a suppressor mutation in the chromosome, said mutation blocking translational read-through of the message of the gene. A further approach is to maintain the rDNA stably in the host by integrating it into the chromosomes of the GEMs.

Recently, an alternative biological containment strategy has been developed in which a recombinant vector is endowed with a gene encoding a cell killing function which gene is under the control of a promoter only being expressed under certain environmental conditions, such as conditions prevailing in an environment outside the primary environment of the GEMs, or when the vector is unintentionally transferred to a secondary host, or the expression of which is stochastically induced. By using incorporation in a GEM of such a cell killing function and selecting appropriate regulatory sequences, vectors can be constructed which are contained in the primary host cell and/or in a primary physical environment. A cell killing function as defined herein may also be referred to as an active biological containment factor.

If a stochastically induced mechanism of expression regulation is selected for such a biological containment system, a population of GEMs containing the system will, upon release to the outer environment or if used as a live vaccine, be subjected to a random cell killing which will lead to an increase of the doubling time of the host cell population or eventually to the disappearance of the organisms.

The above-mentioned genes encoding cell killing functions are also frequently referred to as "suicide" genes, and biological containment systems based upon the use of such genes, the expression of which are regulated as defined above, are commonly described as conditional lethal systems or "suicide" systems. Up till now, several such cell killing functions have been found in bacterial chromosomes and in prokaryotic plasmids. Examples of chromosomal genes having cell killing functions are the gef (Poulsen et al., 1990) and relF (Bech et al., 1985) genes from $E.\ coli_{K-12}$. Examples of plasmid encoded suicide genes are hok and flmA (Gerdes et al., 1986) genes isolated from plasmids R1 and F, respectively, the snrb gene also isolated from plasmid F (Akimoto et al., 1986) and the pnd gene isolated from plasmids R16 and R483 (Sakikawa et al., 1989 and Ono et al., 1987). Common features of these genes are that they are transcribed constitutively, regulated at a post-transcriptional level, and that they all encode small toxic proteins of about 50 amino acids and that their translation is controlled by antisense RNA. The application of the hok gene in a biological containment system has been disclosed in WO 87/05932.

An alternative biological containment system is disclosed in WO 95/10614 which is based on the use of genes, the expression of which in a cell where the gene is inserted, results in the formation of mature forms of exoenzymes which are hydrolytically active in the cytoplasm of the cell and which can not be transported over the cell membrane. When such enzymes are expressed, the normal function of the cell becomes limited to an extent whereby the competitiveness, and hence the survival, of a population of such cells is reduced.

The stable maintenance of low copy-number plasmids in bacteria is secured by a number of plasmid-borne gene systems, one of which is based on killing of plasmid-free cells (also termed post-segregational killing). This regulated killing is based on a toxin-antidote principle, i.e. a two-component system comprising a stable toxin and an unstable antidote for the toxin. One such system, which is referred to as a proteic killer gene system is based on protein toxins and protein antidotes (reviewed by Jensen and Gerdes, 1995). The natural function of such systems is to provide stable maintenance of plasmids and it has not been suggested previously to utilize the systems as the basis for confining GEMs to a particular environment.

The *E. coli* relB operon encodes three genes, relB, relE and relF (Bech et al., 1985). It has now been found that relE encodes a cytotoxin whose overproduction is lethal to host cells and that the relB gene encodes an antitoxin that prevents the lethal action of RelE. When present on a plasmid, the relBE operon was able to stabilize the inheritance of a mini-R1 test plasmid. It was also found that relBE homologous gene systems are found in a wide variety of Gram-negative and Gram-positive bacteria and in Archae.

These results show that the relBE genes constitute a new ubiquitously occurring family of gene systems that belongs to the proteic plasmid stabilization systems.

These findings has opened up for an alternative, highly effective and versatile biological containment system as it is described in the following. Importantly, it has been discovered that such a system involves the significant advantage that the frequency of spontaneously occurring mutants of microorganisms that have become resistant to the lethal effect of these cytotoxins is very low. This implies that this biological containment system is very safe.

SUMMARY OF THE INVENTION

Accordingly, the invention pertains in a first aspect to a method of conditionally controlling the survivability of a recombinant microbial cell population, the method comprising (i) providing in the cells of said population a gene coding for a cytotoxic first kind of polypeptide, the gene is selected from the group consisting of the gene coding for the *E. coli* K-12 RelE polypeptide and a gene coding for a functionally equivalent polypeptide (said genes collectively being designated herein as the relE gene family), said gene is expressible in the cells of the population and, operably linked to the gene, a regulatable regulatory DNA sequence and (ii) cultivating the cell population under conditions where the relE gene or the gene coding for a functionally equivalent polypeptide is expressed, the expression leading to an at least partial killing of the cell population.

In a further aspect there is provided a method of confining an extrachromosomal replicon to a microbial cell population, the method comprising the steps of
(i) isolating a microbial cell naturally containing a gene belonging to the relE gene family coding for a first kind of polypeptide that, when it is expressed in the cell, acts as a toxin for the cell or, if the cell does not naturally contain a gene belonging to the relE gene family, introducing such a gene into the cell,
(ii) introducing into the cell the extrachromosomal replicon to be confined, said replicon containing a gene coding for a second kind of polypeptide that, by binding to the first kind of polypeptide, acts as an antitoxin for said first kind of polypeptide,
(iii) cultivating the cell under conditions where the genes coding for the first and the second kind of polypeptides are expressed, whereby a daughter cell that does not receive a copy of the extrachromosomal replicon is killed by the first kind of polypeptide being expressed in the absence of expression of the second kind of polypeptide.

In a still further aspect, the invention relates to a method of post-segregationally stabilizing a plasmid in a microbial host cell population, the method comprising the steps of
(i) recombinationally inserting into the plasmid (a) a gene coding for a first kind of polypeptide selected from the group consisting of the *E. coli* K-12 RelE polypeptide and a functional equivalent thereof, said first kind of polypeptide having a toxin effect on the host cell and (b) a gene coding for a second kind of polypeptide that (1) is capable of acting as an antitoxin for first kind of polypeptide and (2) is capable of being degraded in the host cell at a higher rate than that at which the first kind of polypeptide is degraded,
(ii) cultivating the cell population under conditions where the genes coding for the first kind and second kind of polypeptides are expressed, whereby a daughter cell that does not receive at least one copy of the plasmid is killed as a result of the faster degradation of the second kind of polypeptide.

In yet other aspects, the invention provides a recombinant microbial cell comprising a gene coding for a first kind of polypeptide selected from the group consisting of the *E. coli* K-12 RelE polypeptide, a gene coding for a functionally equivalent polypeptide hereof or a variant or derivative of any such polypeptide, said first kind of polypeptide having a toxic effect on the cell, subject to the limitation that when the cell is *E. coli*, the gene coding for the first kind of polypeptide is not derived from *E. coli*, and a composition comprising such cells.

The invention also pertains to several methods of containing cells or replicons including
(1) a method of limiting the survival of a cell population in a first or a second environment, which method comprises
(i) transforming the cells of said population with a gene coding for a cytotoxic polypeptide, the gene is selected from the group consisting of the gene coding for the *E. coli* K-12 RelE polypeptide, the gene coding for the plasmid F CcdB polypeptide, the gene coding for the plasmid R1 PemK polypeptide, the gene coding for plasmid RP4 ParE polypeptide, the gene coding for the prophage P1 Doc polypeptide and a gene coding for a functionally equivalent polypeptide for anyone of said polypeptides, said gene is expressible in the cells of the population, and operably linked to the gene, a regulatory DNA sequence being regulatable by an environmental factor and which regulates the expression of said gene, and (ii) cultivating the cell population under environmental conditions where the gene coding for the cytotoxic polypeptide is expressed, the expression leading to an at least partial killing of the cell population, (2) a method of containing an extrachromosomal recombinant replicon to a first kind of cell, where said replicon is naturally transferable to a second kind of cell, which method comprises providing on the recombinant extrachromosomal replicon a gene whose expression results in the formation of a cytotoxic polypeptide selected from the group consisting of the E. coli K-12 RelE polypeptide, the plasmid F CcdB polypeptide, the plasmid R1 PemK polypeptide, the plasmid RP4 ParE polypeptide, the prophage P1 Doc polypeptide and a functionally equivalent polypeptide for anyone of said polypeptides to an extent whereby the function of the cell is being limited, said first kind of cells having or being modified to have a chromosomal replicon comprising a regulatory nucleotide sequence the gene product of which inhibits the expression of said gene or the cell function-limiting effect of the polypeptide and thereby protects said first kind of cells, said regulatory gene being lacking in said second kind of cell, whereby, if a cell of the second kind receives said extrachromosomal recombinant replicon said gene is expressed and has a function-limiting effect on said second kind of cell, and (3) a method of stochastically limiting in an environment the survival of a cell population, the method comprising transforming the cells thereof with a recombinant replicon containing a regulatably expressible gene which, when expressed in a cell, encodes a cytotoxic polypeptide selected from the group consisting of the E. coli K-12 RelE polypeptide, the plasmid F CcdB polypeptide, the plasmid R1 PemK polypeptide, the plasmid RP4 ParE polypeptide, the prophage P1 Doc polypeptide and a functionally equivalent polypeptide for anyone of said polypeptides, the expression of said gene leading to formation of the polypeptide to an extent whereby the function of the cells is being limited, the expression of said gene is stochastically induced as a result of recombinational excision of an excisable negatively functioning regulatory nucleotide sequence which, while present in the cells, inhibits expression of the gene coding for the polypeptide, said negatively functioning regulatory nucleotide sequence being contained in the recombinant replicon or in an other recombinant replicon present in cells of the population containing the replicon.

DETAILED DISCLOSURE OF THE INVENTION

One objective of the present invention is to provide a novel approach to conditionally controlling the survivability of a recombinant microbial cell population. This approach is based on the use of what is generally referred to as proteic killer systems which have been reviewed i.a. by Jensen et al., 1995. These systems consist of two components, a cytotoxin polypeptide (also referred to herein as a first kind of polypeptide) and a corresponding antitoxin or antidote polypeptide (also referred to herein as a second kind of polypeptide) that by binding to the cytotoxic polypeptide inhibits the toxic effect hereof. A general characteristic of such proteic killer systems is that the antitoxin component in contrast to the toxin component is susceptible to protease degradation, resulting in a decay of the antitoxin polypeptide.

As used herein, the expression "microbial cell" includes any prokaryotic and eukaryotic cells as well as cells of Archae species. Thus this expression includes cells of bacterial species, fungal species, animal species including invertebrates, vertebrates, mammals, humans and insects, and plant cells.

Thus, in one aspect of the invention there is provided such a method of conditionally controlling the survivability of a recombinant microbial cell population that comprises as the first step, providing in the cells a gene coding for a cytotoxic first kind of polypeptide, which gene is selected from the gene coding for the E. coli K-12 RelE polypeptide and a gene coding for a structurally and functionally equivalent polypeptide and, operably linked to the gene, a regulatable regulatory DNA sequence.

Genes which are structurally and functionally equivalent to relE are herein collectively referred to as the relE gene family or as relE homologues. This group of genes including the E. coli plasmid P307 derived relE homologue encompasses genes the gene products of which have cytotoxic effects and which, relative to E. coli K-12 RelE, have at least 20% such as at least 30% e.g. at least 40% identical and conserved amino acids. The sequences listed in the below Table 1.5 are putative RelE homologues.

Whereas, in accordance with the invention, presently preferred recombinant microbial cells are prokaryotic cells such as Gram-negative and Gram-positive bacterial cells, it has been found that the survivability of other microbial cells such as Archae, yeast cells, fungal cells, animal cells including human cells and plant cells and replicons of such organisms can be conditionally controlled using the methods of the present invention.

In the present context, the expression "conditionally controlling" refers to a construction of the microbial cell which permits that the gene coding for the cytotoxic polypeptide can be expressed under certain pre-determined environmental conditions whereas under other such conditions, the gene is not expressed. Hence, the survivability of the microbial cells can be made dependent on certain pre-selected conditions.

In accordance with the invention, the survivability of microbial cells is controlled by the expression in the cells of a cytotoxic polypeptide selected from E. coli K-12 RelE polypeptide and a functionally equivalent polypeptide. As used herein, the term "cytotoxic" refers not only to a loss of the ability of microbial cells containing the toxin-encoding gene to remain viable as determined by the capability to propagate in media which, under identical environmental conditions, support unrestricted growth of similar cells not containing the toxin-encoding gene, but also to cells having, as a result of the expression of the polypeptide-encoding gene, a limited cell function, the latter expression denoting that the growth of a cell as manifested i.a. by the synthesis of new cell material and the rate of replication of the cell is decreased.

During the experimentation leading to the invention it was surprisingly found that a range of cytotoxic polypeptides according to the invention have the effect that they inhibit translation of genes. This general effect of RelE polypeptides and functionally equivalent polypeptides appears to represent a hitherto undiscovered mechanism for controlling survivability of cells and thus for containment of such cells or replicons in accordance with the methods of the present invention.

Whereas the recognizable manifestation of such limited cell function may ultimately be cell death, it may also be a reduced cell growth appearing as a reduced rate of replication resulting in a reduced increase of cell numbers within a certain period of time as a result of an increase of the lag phase and/or of the cell doubling time. Other manifestations may be a relatively increased requirement for one or more nutrient components or a relatively higher susceptibility to detrimental environmental factors such as sub-optimal temperatures or cell damages caused by toxic substances.

In the present context, the expression "a functionally equivalent polypeptide" refers to a polypeptide that has substantially the same effect on the survivability of microbial cells as the RelE polypeptide of E. coli K-12. As it is shown herein, a variety of Gram-positive and Gram-negative bacteria and Archae organisms comprise DNA sequences showing homology with the RelE polypeptide. To the extent gene products of structural homologues of the relE gene product show an effect on microbial cell survivability as it is defined above, they are encompassed by the present invention. It will also be appreciated that the term "functional equivalent" includes variants or derivatives of any of the above first kind of polypeptides, the sequences of which have been modified by substitution, deletion or addition of one or more amino acids and the gene product of which has retained at least part of the cytotoxic function of the gene product of the non-modified sequence.

In the above method, a regulatable regulatory DNA sequence is operably linked to the gene coding for the cytotoxic polypeptide. In accordance with the invention, such a regulatory sequence can be one with which the gene coding for the cytotoxic polypeptide is naturally associated or it can be a sequence with which the gene is not naturally associated. In the present context, the term "regulatory DNA sequence" is intended to indicate a DNA sequence which directly or indirectly regulates the expression of the gene coding for the cytotoxic polypeptide at the level of transcription or at the level of translation or at the level of protein function. The regulatory DNA sequence may thus be one, the function of which results in a suppression or inhibition of the activity of the regulatable promoter.

Such regulatory DNA sequences are referred to herein as "negatively functioning regulatory DNA sequences". One interesting example of such a regulatory DNA sequence is a sequence coding for a repressor substance which represses the expression of the gene coding for cytotoxically active polypeptide and which substance may, when a cell containing it is released to a human or an animal body or to the outer environment where the substance is no longer being expressed, undergo a decay whereby the repression of expression of the cytotoxin-encoding gene is gradually reduced and eventually, when the decay of the repressor is completed, the repression is removed.

Another example of such a regulatory DNA sequence is a sequence encoding a polypeptide that acts as an antidote or antitoxin for the cytotoxic polypeptide. Such a sequence include the relB gene derived from the relBE operon of E. coli K-12 which is capable of binding to the RelE polypeptide and thereby inhibiting its effect. As also shown herein, sequences encoding such antitoxins can be found in Gram-negative and Gram-positive bacteria and in Archae. Such homologues of the relB sequence are encompassed by the present invention.

In preferred embodiments of the invention, the regulatory DNA sequence may be present in the cell in one or more recombinant replicons and it may be contained in the same replicon as that containing the cytotoxin-encoding gene or in a different recombinant replicon.

One way whereby the expression of the cell function-limiting cytotoxic polypeptide can be regulated is by providing in the cell a gene coding for the polypeptide, which gene is regulated at the level of transcription. The regulation at the level of transcription may be carried out in various ways including a regulation by means of a promoter, regulated by one or more factors. These factors may either be ones which by their presence ensure expression of the gene coding for polypeptide or may, alternatively, be factors which suppress the expression of the gene so that their absence causes the polypeptide to be expressed.

Factors regulating the activity of the promoter as defined above may be selected from a variety of factors. Thus, the expression of the gene encoding the polypeptide may be determined by the environmental conditions, by the physiological state of the cells, or by a cyclical or stochastic event. In the present context, the term "cyclical event" is understood to mean a cyclically recurrent event causing changes in certain factors known to be potentially useful in affecting the expression of genes such as temperature conditions, changes in light intensity or hormonal changes. The term "physiological state of the cells" denotes factors such as cell density or the growth phase of cells.

In accordance with the invention, advantageous promoter regulating factors are readily regulatable factors including the presence or absence of a certain chemical substance in the environment or the physical conditions in the environment such as the prevailing temperature or other physical factors (e.g. the intensity of the light in the environment). Thus, it is possible to envisage containment systems as presently claimed, in which the gene coding for the cytotoxic polypeptide is expressed when a certain chemical substance present in a first environment such as the fermentation medium in which the cell is propagated, is not present in a second environment to which the cell is released, or when a factor required for the growth or survival of the cell is no longer present, or the factor is one which, when it is depleted or exhausted from an environment of the cell, has the desired effect, viz. that the gene is expressed.

The promoter regulating the transcription of the gene coding for the cytotoxic polypeptide can also become activated in a second environment of the cell by a chemical substance which is not present in a first environment of the cell, but which is present in the second environment in sufficient quantities to activate the promoter. Similarly, the promoter may be a promoter which is activated by a shift in temperature, such as a shift from a higher temperature in a first environment as e.g. a fermentation vessel, to a lower temperature prevailing in an outside second environment, or the intensity of light, in that the promoter may be one which is activated in the presence of light of sufficient intensity, but is inactive in the darkness prevailing in a first environment such as a fermentation vessel.

Where microbial cells as defined herein are cells that are to be released to the outer environment in a controlled manner, e.g. to a restricted area of land or to the intestinal tract of a human or an animal, the regulatable promoter may be one which is regulated chemically, i.e. by the presence or absence of a certain chemical substance in the environment of the cells as it has been explained above.

However, the regulatable promoter is advantageously a promoter which is activated cyclically, e.g. by changes of the temperature, or by a stochastic event. The term "stochastic event" as used herein is intended to denote an event which occurs at random at a certain frequency per cell per generation or frequency per unit time which, in accordance with the invention, may result in a limitation of the function of the cells in which the activation of expression of the cytotoxic polypeptide occurs, optionally to an extent which leads to the death of the cells. The stochastic event may be occasioned by periodic inversions of the region carrying the promoter or by recombinational excision of a recombinationally excisable negatively functioning regulatory DNA sequence as defined above.

It should be noted that in order to ensure a general applicability of the present invention, the promoter used to initiate transcription of the gene coding for the toxic polypeptide is preferably a promoter which is capable of causing expression of said gene in a wide range of cells.

In case of regulatable transcription of the polypeptide, the regulatory DNA sequence may e.g. be a promoter isolated from bacterial operons involved in the biosynthesis of amino acids or from bacterial genes, the transcription of which is activated late in the stationary growth phase or from bacterial genes involved in the synthesis of cell surface structures such as fimbriae. Examples of suitable promoters include the *E. coli* trp promoter which becomes activated in the absence of tryptophan, the bacteriophage λ $P_R$ and $P_L$ promoters controlled by temperature sensitive regulatory DNA sequences, the *Bacillus subtilis* sporulation gene promoters which are activated during sporulation, and the *E. coli* and *Salmonella* fimbriae gene promoters which are activated stochastically.

In case of chemically regulatable promoters, the chemical substance, the presence or absence of which determines the activation of the promoter, is suitably selected from carbon or nitrogen sources, metabolites, amino acids, nucleosides, purine or pyrimidine bases or metal ions. When the chemical substance is one which, when present, suppresses promoter activity, it is preferably a substance which rarely occurs in the natural environment in such concentrations that the promoter would not be activated when the cell is released to the natural environment. One example of such a promoter is the trp promoter which is repressed in the presence of tryptophan in the environment of the cell, but which is derepressed in the absence of sufficient amounts of tryptophan in the environment. A containment system according to the invention using the trp promoter or another promoter being regulated in the same manner, might therefore comprise an amount of tryptophan in a first environment, such as a fermentation vessel, which is sufficient to repress the promoter in such an environment, the promoter, however, being derepressed when the cell is released from the first environment to a second environment, e.g. the outer environment which usually contains very low amounts of tryptophan or no tryptophan at all.

It is also possible to select a promoter that is regulated by the absence or presence of one or more compounds in exudates of plants colonized with a recombinant organism according to invention.

In this context, another useful promoter is an arabinose inducible promoter including that contained in the plasmid pBAD (Guzman et al., 1995). Without arabinose added to the growth medium, the pBAD promoter is completely turned off. However, in the presence of arabinose, strong transcription is induced. This particular promoter is repressible by the addition of glucose to the growth medium. Thus, by the addition of glucose, transcription from pBAD can be rapidly and efficiently turned off. The glucose repression effect is epistatic to the inducer effect by arabinose. Hence, if cells with a pBAD-carrying plasmid are grown in a medium containing both arabinose and glucose, the promoter is not induced. However, if cell growth depletes the medium for glucose, then the promoter will be induced. Therefore, such a plasmid is suitable for the conditional turning on and off the expression of gene, in particular toxin-encoding genes as described herein.

Accordingly, in one embodiment of the invention the method is used to contain microbial cells wherein the promoter is suppressible by a first kind of chemical compound and inducible by a second kind of chemical compound whereby, when the first kind of compound is depleted from the medium, the promoter is induced by the second kind of compound.

Another example of a regulatable promoter, the activation of which is determined by a chemical substance is the lac promoter which is inducible by e.g. isopropyl-β-D-thiogalactopyranoside (IPTG).

As mentioned above, the regulatable promoter may be a promoter, the activity of which is determined by the temperature prevailing in the environment of a cell containing the gene coding for the cell function-limiting cytotoxin and a regulatable promoter regulating the expression of the gene. In such a case, the regulation of the promoter is advantageously obtained by the presence in the cell of a gene coding for a temperature sensitive repressor for the promoter. As one typical example, the λ promoters including those mentioned above may be regulated by a temperature sensitive λ cl repressor.

Promoters which are activated stochastically by periodic inversions of the promoter region (in the present context, such promoters are also termed as "invertible promoters" and "inversional switch promoters") and which are useful for the purposes of the present invention include as examples the hin, cin and gin promoters. One particularly useful invertible promoter is the fimA promoter which is one *E. coli* fimbriae promoter. The activation (inversional switch) of this promoter is regulated by the gene products of the two genes which for the present purposes is termed the "on" and the "off" genes, the on gene product inducing a switch from off (inactive) to on (active), and the off gene product inducing a switch from on to off. In a wild-type *E. coli* cell where the fimA gene and its associated promoter is present in one copy on the chromosome, the inversional switch occurs with a switching frequency of about one cell/1000 cells/generation. It is, however, possible to regulate the frequency of the inversional switch as required by regulating the dosage of expression of the on and off genes. This is e.g. effected by means of suitable promoters transcribing into the on and off genes. The frequency of transcription initiation by these promoters will then determine the relative dosage levels of the on and off gene products being formed.

In accordance with the invention, one particular method of stochastically regulating the expression of the gene coding for the toxic polypeptide is the induction of the gene expression as a result of recombinational excision of an excisable negatively functioning regulatory DNA sequence which, while present in the cell, inhibits expression of the gene. In the present context, the term "recombinational excision" refers to the result of a naturally occurring phenomenon of genetic recombination (cross-over) whereby DNA sequences in replicons, in a controlled process, pair, brake and rejoin to form recombinant replicons by the sequential action of enzymes acting on the DNA. The frequency of recombinational events in a cell depends i.a. on the degree of homology between paired complementary nucleotide sequences and on the length of the complementary sequences. Thus, it has been shown that about 50 base pairs of homology may be required to obtain recombination in a bacterial cell.

When a negatively regulatory DNA sequence is inserted between directly repeated nucleotide sequences of a sufficient length in a recombinationally proficient cell which, in accordance with the invention contains a gene coding for the toxic polypeptide, recombination between the repeats results in the recombinational excision of the negatively regulatory DNA sequence permitting the gene to be expressed.

Accordingly, the phenomenon of recombinational excision implies that a DNA subsequence, i.e. the negatively regulatory DNA sequence, is excised from a longer DNA sequence through a recombination event. In essence, the longer DNA sequence is cleaved on either side of the subsequence and the fresh ends are joined, leaving out the subsequence. Recombination occurs between sufficient homologous flanking nucleotide subsequences. Thus, with DNA of the general structure W-X-Y-X-Z, X being a repeated sequence and Y being a negatively regulatory DNA sequence, this could recombine to form W-X-Z, with the Y subsequence being excised.

As mentioned above, the frequency of the recombination can be determined by varying the lengths of the repeats and/or the distance between the repeats. Furthermore, the frequency may be varied by using repeat sequences of varying homologies. Thus, nucleotide sequence repeats being 100% homologous and having a size which does not impair recombination will result in a high recombination frequency and hence, in a high frequency of recombinational excision of the negatively regulatory sequence, whereas mismatches within complementary sequences will reduce the recombination frequency depending on the degree of mismatch. As an example, it has been found that 10% divergence between nucleotide sequence repeats may reduce the recombination frequency 40-fold.

Accordingly, the microbial cell comprising the gene coding for the cytotoxic polypeptide may, in accordance with the invention, be a cell containing a regulatory DNA sequence which is a recombinationally excisable negatively functioning regulatory DNA sequence being flanked by a first flanking nucleotide sequence and a second flanking nucleotide sequence substantially homologous with the first flanking sequence. As used herein, the term "substantially homologous with" is used to indicate that the degree of homology is sufficient to result in a desired frequency of recombination. In certain embodiments it may, in order to obtain a desirable maximum frequency of recombination, be advantageous to use direct repeats, i.e. sequences being 100% homologous, whereas in other embodiments where a moderate degree of cell function limitation is desirable, it is appropriate to use repeats which are more or less heterologous, but still allowing a desirable lower frequency of recombination to occur. Accordingly, in the present context, the term "sufficiently homologous" is used to indicate a degree of homology between two flanking nucleotide sequence repeats which results in a desired frequency of recombinational events in a cell containing the gene coding for the toxin polypeptide and a negatively regulatory DNA sequence.

As it also has been mentioned above, the frequency of recombination depends on the lengths of the flanking sequences. In useful embodiments of the invention, flanking sequences are used which have a length being in the range of 100-5,000 base pairs. In certain preferred embodiments, it is advantageous to use flanking sequences, the length of which is in the range of 200-3,000 base pairs. As the flanking sequences can be used any nucleotide repeats of sufficient lengths and homology as it has been defined above. As one useful example of flanking sequences may be mentioned the chloramphenicol resistance gene having a size of about 900 base pairs and which occurs in the plasmid pBR325. Another example of a useful nucleotide sequence which, when inserted as repeats, results in recombination, is a subsequence of the rrnB gene isolated from the plasmid pKK3535 (Brosius et al., 1981, Plasmid, 6:112-118) having a size e.g. in the range of 500 to about 3,000 base pairs, such as 598 base pairs.

In one interesting embodiment of the invention, the excisable negatively regulatory DNA sequence operably linked to the gene encoding the cytotoxic polypeptide is a gene encoding an antisense RNA which forms an RNA-RNA duplex with said the messenger RNA of the polypeptide-encoding gene and thereby, when it is expressed, inhibits translation of said gene coding for the polypeptide.

In another useful embodiment of the present invention, the recombinationally excisable negatively regulatory DNA sequence is a gene encoding a polypeptide repressor of transcription of the polypeptide-encoding gene. Such a repressor may, e.g. be a lac repressor including the repressor encoded by the Laclq gene. It will be appreciated that the negatively regulatory DNA sequence can also be a gene coding for RelB antitoxin or functionally equivalents hereof.

In a further useful embodiment of the invention, the excisable negatively regulatory DNA sequence is a transcription termination sequence, preventing the transcription of the cytotoxic polypeptide-encoding gene. In one specific embodiment of the invention, such a suitable terminator sequence is the rpoCt' transcription terminator isolated from the plasmid pHBA102rpoCt (Squires et al., 1981, Nucleic Acid Res., 9:6827-6839).

Negatively regulatory DNA sequences which, in accordance with the invention, are suitable, can be isolated from DNA sequences derived from a virus, or a prokaryotic or eucaryotic cell. Thus, sources of the DNA sequence include bacterial chromosomes, bacterial plasmids, prokaryotic viruses, eucaryotic viruses, eucaryotic plasmids, or eucaryotic chromosomes.

In preferred embodiments of the invention, the excisable negatively regulatory DNA sequence and the first and second flanking sequences, both as defined above, is provided in the form of a "cassette" which term is used herein to describe a readily insertable DNA sequence comprising at least the above-mentioned sequences and optionally the gene coding for the cytotoxically active polypeptide, and optionally further nucleotide sequences including as examples a suitable marker such as a gene coding for antibiotic resistance. In the present context, the term "insertable" denotes that the cassette as defined herein is provided with suitable restriction sites at both ends allowing for insertion in a replicon having the same restriction sites. Accordingly, such preferred restriction sites include sites which occur frequently in replicons where insertion is desirable or alternatively, restriction sites which may be easily provided in such replicons.

It will be understood that, in accordance with the invention, a cassette as defined above and which does not comprise the gene coding for toxin polypeptide and operably linked to the negatively regulatory DNA sequence, may be inserted in a replicon which is different from the replicon containing said gene. Optionally, the cassette as defined above is inserted in a first replicon such as e.g. a transposon and subsequently inserted via the transposon into the chromosome to obtain a cell as defined herein.

As it has been explained above, the activation of certain invertible promoters such as the fimA promoter or functional homologues hereof is regulated by the gene products of an on gene and an off gene. It will be understood that this mechanism of promoter regulation provides the possibility of using the off gene or a functional homologue hereof as a negatively regulatory DNA sequence which may be inserted in the microbial cell as defined herein, as a recombinationally excisable DNA sequence in the manner explained in details above. Accordingly, in one embodiment, the present invention provides a microbial cell wherein the toxin-encoding gene is stochastically expressed as a result of recombinational inversion of an invertible promoter sequence.

In plasmids, inherent mechanisms occur whereby multimer resolution of the plasmid during replication takes place.

As exemplified by the broad host range plasmid RP4, this resolution system may comprise (1) a gene coding for a multimer resolving enzyme, a resolvase and (2) a site for the site-specific resolvase-mediated resolution. In plasmid RP4 the gene coding for the resolvase is parA and the site for the resolution is designated mrs. If two mrs sites are placed in direct orientation, a DNA sequence inserted between those two sites may, if the parA gene is present in the same host cell, be deleted at a relatively high frequency whereby a site-specific recombination system is provided. In useful embodiments the parA gene may be located in trans.

It has been found that such a site-specific recombination system provides a useful mechanism for stochastically regulating the expression of a gene such as the gene coding for the toxic polypeptide as defined herein, since the site-specific recombination may be used to obtain recombinational excision of a negatively regulatory DNA sequence as defined above.

Accordingly, in one interesting embodiment, the present invention provides a microbial cell as defined herein in which the negatively regulatory DNA sequence is a sequence flanked by a first site for a site-specific resolution recombinase and a second site for site-specific resolution, the second site being recognizable by the same or a functionally equivalent multimer resolving enzyme as is the first site, whereby the regulatory sequence is recombinationally excisable in the cell. In a specific embodiment, the gene coding for the multimer resolving enzyme is located in trans relative to the sites for site-specific resolution. In the present context, one useful example of a suitable gene is the parA gene isolated from plasmid RP4.

In accordance with the invention, the method of controlling the survivability of microbial cells can be based on providing in the cells a gene coding for a cytotoxic polypeptide that is structurally and functionally equivalent to the *E. coli* RelE polypeptide (the relE gene family). Such a genie can be derived from the chromosome or another replicon of a Gram-negative bacterium including *Enterobacteriaceae* spp. such as *E. coli, Hemophilus* spp. such as *H. influenzace, Vibrionaceae* spp. such as *V. cholerae, Pseudomonadaceae* spp., *Helicobacter* spp. such as *H. pylori* and *Synechosystis* spp, the latter organisms belonging to the group of cyanobacteria. The gene may also be derived from the chromosome and other replicons of Gram-positive bacteria including lactic acid bacteria such as *Streptococcus* spp including *Streptococcus pneumoniae., Bacillaceae* spp such as *B. thuringiensis*, and *Mycobacterium* spp. and from species belonging to Arhae such as *Methanococcus jannaschii* and *A. fulgidus*. Such genes include those that are defined herein as belonging to the relE gene family. The RelE equivalent polypeptide from *M. jannaschii* was shown to be toxic for *E. coli* when expressed in this organism.

However, genes coding for cytotoxins of other proteic killer systems and which are therefore functional equivalents of the *E. coli* K-12 RelE polypeptide can also be used in accordance with the invention for conditionally controlling the survivability of microbial cells. Such genes include the gene coding for the plasmid F CcdB polypeptide, the gene coding for the plasmid R1 PemK polypeptide, the gene coding for plasmid RP4 ParE polypeptide and the gene coding for the prophage P1 Doe polypeptide, as described by Jensen et al., 1995.

It will be understood that in this context, the term "functional equivalent" includes variants or derivatives of any of the above first kind of polypeptides the sequences of which have been modified by substitution, deletion or addition of one or more amino acids and the gene product of which has retained at least part of the function of the gene product of the non-modified sequence.

In accordance with the invention, the relE family gene or any gene coding for a toxin of a proteic killer system is provided in the microbial cells at a location where it can be expressed effectively. Thus, in useful embodiments the gene is present on the chromosome of the cells whereas in other embodiments it is preferably located on an extrachromosomal element such as a plasmid or a cosmid. In a specific embodiment, the microbial cells according to the invention do not contain a gene coding for a second type of polypeptide that is capable of counteracting the cell toxic effect of the RelE polypeptide or the functional equivalent hereof.

However, in other useful embodiments, the microbial cells comprise a gene coding for a second kind of polypeptide that is capable of binding to the relE polypeptide or the functional equivalent hereof, the binding resulting in that the toxic effect of the RelE polypeptide or the functional equivalent is at least partially counteracted. Such a counteracting second kind of polypeptide is, as it is mentioned above, also referred to herein as an antitoxin or an antidote for the cytotoxic polypeptide.

Although, in certain uses of the present method, it is preferred that the genes coding for both the toxic polypeptide and the antitoxin herefor is under the control of the same regulatory sequences, it may, in other uses, be advantageous that the gene coding for the second kind of polypeptide is operably linked to a different regulatable regulatory DNA sequence as defined above, permitting that the gene coding for the second kind of polypeptide is suppressed under conditions where the gene coding for the RelE polypeptide or the functional equivalent is expressed.

It will be appreciated that the genes coding for the toxin polypeptide and the antitoxin polypeptide, respectively can be present on the same replicon such as a plasmid or on the chromosome, or they can be present on different replicons in the microbial cells.

A useful second kind of polypeptide is the RelB polypeptide derived from *E. coli* K-12 which i.a. binds effectively to the *E. coli*-derived RelE polypeptide. However, the regulation of the toxic effect of the first kind of polypeptide can also be based on providing in the cells a gene coding for a second kind of antitoxically active polypeptide that is functionally equivalent to the *E. coli* RelB polypeptide. Such a gene can be derived from the chromosome or another replicon of a Gram-negative bacterium including *Enterobacteriaceae* spp. such as *E. coli, Hemophilus* spp. such as *H. influenzae, Vibrionaceae* spp. such as *V. cholerae, Pseudomonadaceae* spp., *Helicobacter* spp. such as *H. pylori*, and *Synechosystis* spp belonging to the group of cyanobacteria. Additionally, genes coding for structural and functional equivalents of the *E. coli* RelB polypeptide can be isolated from Gram-positive bacteria including lactic acid bacterial species such as *Streptococcus* spp., *Bacillaceae* spp. such as *B. thuringiensis*, and *Mycobacterium* spp. and from species belonging to Arhae such as *M. jannaschii* and *A. fulgidus*. Sequences for the *E. coli* RelB polypeptide and for equivalents isolated from the above organisms are listed in Table 1.6.

Genes coding for functional equivalents of the *E. coli* K-12 RelB polypeptide which in accordance with the invention can be used for containing microbial cells and replicons include the genes coding for the plasmid F CcdA polypeptide, the plasmid R1 Peml polypeptide, the plasmid RP4 ParD polypeptide and the prophage P1 Phd polypeptide.

It will be understood that in this context the term "functional equivalent" includes variants or derivatives of any of the above second kind of polypeptides, the sequences of which have been modified by substitution, deletion or addition of one or more amino acids and the gene product of which has retained at least part of the function of the gene product of the non-modified sequence.

It is a significant objective of the present invention to provide the means of conditionally controlling the survivability of microbial cells that expresses one or more genes coding for a gene product of interest. In accordance with the invention such an objective is pursued for any type of gene products including enzymes such as proteases, enzymes which are effective in degrading carbohydrates such as starch degrading enzymes, lipid degrading enzymes and nucleases.

However, it is of particular interest to provide containment of microbial cells wherein the gene product of interest is selected from an immunologically active gene product, a gene product that is effective in degradation of an environmental pollutant and a pesticidally active product.

Accordingly, in such specific embodiments the microbial cells are cells which further comprise a DNA sequence that is selected from a sequence coding for an immunologically active gene product, a sequence coding for a pesticidally active gene product and a sequence coding for a pollutant degrading gene product.

In the present context, the term "immunologically active gene product" is used to describe an epitope (antigenic determinant) from a pathogenic organism which, when it is administered to the body of a human or an animal, is capable of stimulating the formation of antibodies therein. A microbial cell as defined herein which contains one or more genes encoding such a gene product can be utilized in the preparation of live vaccines. In the immunization against several pathogens it is considered advantageous to administer live vaccines as compared to killed organisms or antigenic fragments of the pathogen, since the level of immunity conferred by a live vaccine is frequently higher than that conferred by vaccines comprising killed pathogenic organisms or fragments thereof. Most currently used vaccines comprising viable epitope-containing organisms are either based on recombinant non-pathogenic organisms encoding the epitope or they are based on attenuated pathogenic organisms. The cell advantageously contains a multiplicity of genes each of which codes for a specific immunologically active gene product.

However, up till now the use of live vaccines has been limited since it is difficult to obtain the right combination of attenuation, viability and adequate immune response. Furthermore, the deliberate release of genetically engineered microorganisms to the body and to the external environment which is a result of the use of viable recombinant organisms as vaccines, is currently not allowed in any country for reasons of public concern as to the possible long-term environmental impact, in particular the risk of permanent establishment of the GEMs in the environment.

The present invention provides advantageous means of circumventing these problems associated with the use of known GEM-based live vaccines by introducing into a viable epitope-containing cell the regulatably expressible gene coding for a cell toxic polypeptide as defined above. In particularly interesting embodiments, the invention provides, as a useful basis for a viable vaccine, the microbial cells as defined above whose expression is stochastically induced.

In useful embodiments of the invention, the cell which contains the DNA sequence coding for an immunologically active gene product further comprises means for transporting the epitope, when expressed, to the outer surface of the cell, i.e. translocating it across the cell membrane. Preferably such a translocation is obtained by inserting the gene coding for the epitope into a nucleotide sequence coding for an outer cell surface polypeptide structure such as fimbriae which contains the fimbrillin protein, pili, flagellae or certain other surface proteins including as an example the OM protein found in *Streptococcus* species. By providing the cell with such a hybrid nucleotide sequence being expressible in the cell, the gene product hereof will be a fusion or hybrid protein comprising the epitope and the relevant cell surface structure.

A cell in which a fusion protein is expressed which comprises the epitope fused to a surface structure protein by which the cell can adhere to the mucosal cells of a body to which the cell is administered is considered to be particularly useful in that the epitope will become in close contact with the mucosa and thereby effectively stimulate a protective immune response in the form of the excretion of secretory antibodies of the IgA and IgG classes.

Furthermore, the adhesion of the epitope-carrying cell will ensure that the cell is retained in the human or animal body for a period of time which is sufficient to obtain the desired immune response. It is considered that a satisfactory immunization typically may be obtained if the cell is present in sufficient numbers in a particular body environment such as the intestinal tract for a period in the range of 15-30 days, depending on the nature and the activity of the epitope expressed from the cell.

As it will be understood from the above description of the gene coding for the cell function-limiting toxic polypeptide and the DNA sequence regulating its expression, the present invention may provide useful means of providing live vaccines based on recombinant organisms which are immunologically effective and which can be used without the risk of undesired spreading of recombinant genes to the microflora of humans and animals or to the outer environment.

In accordance with the invention, a useful cell for the preparation of a live vaccine is one selected from a bacterial species which inherently contains an outer surface structure as mentioned above. Such species include as examples species of Enterobacteriaceae such as *Salmonella* and *E. coli* species, *Vibrionaceae* and *Pseudomonadaceae*. It will be understood that strains of such species which are particularly useful in the present invention as the basis of a live vaccine as defined above, are non-pathogenic strains or strains having a low pathogenicity.

The epitope expressed by a cell as defined above may be an epitope derived from any pathogenic organism or agent the obtainment of immunity against which is desirably. Such pathogens include viruses, bacteria and eukaryotic organisms such as fungi, yeast or protozoa.

In commercially important embodiments, the microbial cell comprising the gene coding for a cytotoxic polypeptide contains a nucleotide sequence coding for a pesticidally active gene product. In this context, the term "pesticidally active gene product" is used to denote a product which, when expressed in a cell being released to an environment where there is a need to reduce or eliminate the presence of pests that feed on plants, including insect pests, nematodes and vermins such as rodents or birds, is effective in respect of such pest control.

Such pests are currently controlled by the administration of toxic chemical pesticides to the infestated environment, but recently various naturally occurring pesticidally active organisms including viruses, bacteria and fungi have been used as biological pest control products.

Prominent examples of such pesticidally active organisms include biotypes or strains of the species *Bacillus thuringiensis* that produce crystalline proteins being toxic to insects, in particular to caterpillars, and several viruses being pathogenic for insects in the larval stage or in the adult stage. However, the pesticidal effect of such organisms is frequently less satisfactory and there is a strong need in farming, forestry and horticulture to provide improved pesticidally active organisms. One approach to solving this problem is to construct genetically engineered organisms having an increased toxic effect or a better survival rate in the environment. In addition to pesticidally active compounds from *B. thuringiensis*, such compounds are produced by other microbial organisms including *Bacillus sphaericus*, fungal species, algal species and plants. In accordance with the invention, genes coding for such biopesticides can be inserted and expressed in the biologically contained cells of the invention.

To the extent such improved organisms are developed, their use in the environment will, as a consequence of current public concern of the potential risks involved in deliberate release of such toxic or pathogenic GEMs, only be approved by official environmental agencies if it can be demonstrated that the release does not lead to an undesired propagation or to an extended survival of such organisms in the environment to which they are applied.

The present invention clearly provides the means of limiting the survival in the environment of genetically engineered pesticidally active organisms. As it has been explained above, the rate of expression of the cytotoxic polypeptide can be regulated stochastically and thus the survival rate of pesticidally active cells may conveniently be adapted to any specific need. Also, the cell function-limiting effect of the toxic polypeptide may, in accordance with the present invention, be adjusted by selecting a first kind of polypeptide that has an appropriate cell function-limiting effect.

In another useful embodiment, the invention provides a cell in which the gene coding for a desired gene product is a sequence coding for a pollutant-degrading gene product. It is known that several xenobiotic compounds polluting the outer environment including soil and water can be degraded by microorganisms having an inherent capability of degrading these compounds. Obviously, the technology of genetic engineering provides means of providing improved organisms having an increased pollutant-degrading capacity or having the capacity to degrade a broad range of compounds, in particular hydrocarbons.

However, the public concern as mentioned above are also relevant in this context and accordingly, the present invention provides useful means of providing improved pollutant-degrading microbial cells, the survival of which can be controlled by regulating the expression of the first kind of polypeptide as it is defined above. In particularly preferred embodiments, the cell contains a gene coding for a pollutant-degrading gene product, the expression of which is induced by the presence of a pollutant degradable by the cell.

In addition to the above desired gene products, the microbial cells according to the invention can express any desired gene product including pharmaceutically active products such as e.g. hormones, interleukines and antibiotically active peptides.

As mentioned above, the invention provides in a further aspect a method of confining an extrachromosomal replicon to a microbial cell population. Basically, the method comprises the steps of isolating or constructing a microbial cell containing a gene belonging to the relE gene family expressing a first kind of polypeptide that is toxic for the cell and introducing into the cell the extrachromosomal replicon to be confined, which replicon contains a gene coding for a second kind of polypeptide acting as an antitoxin for said first kind of polypeptide, and cultivating the cells under conditions where the genes coding for the first and the second kind of polypeptides are expressed, whereby a daughter cell that does not receive a copy of the extrachromosomal replicon is killed by the first kind of polypeptide being expressed in the absence of expression of the second kind of polypeptide.

In preferred embodiments of such a method the cell population consists of cells that comprise a gene coding for a gene product of interest as defined above.

The above method of confining an extrachromosomal replicon is particularly useful when the replicon is a plasmid that naturally occurs in a host cell in a low copy number. Accordingly, the method is useful for confining a plasmid occurring in the microbial cells at a copy number which is in the range of 1-30 including the range of 1-10 such as the range of 1-5.

Microbial cells to which a replicon can be confined in accordance with the invention include Gram-negative bacterial species such as species belonging to *Enterobacteriaceae, Hemophilus, Vibrionaceae* and *Pseudomonadaceae* and Gram-positive bacterial species, fungal cells including yeast cells, animal cells including human cells and insect cells, and plant cells.

In a still further aspect, the invention provides a method of post-segregationally stabilizing a plasmid in a microbial host cell population as described above. As it is mentioned above, the method comprises the steps of (i) inserting into the plasmid a gene coding for a first kind of polypeptide as defined herein and a gene coding for a second kind of polypeptide as also defined herein that is capable of being degraded in the host cell at a higher rate than that at which the first kind of polypeptide is degraded, (ii) cultivating the cell population under conditions where the genes coding for the first kind and second kind of polypeptides are expressed, whereby a daughter cell that does not receive at least one copy of the plasmid is killed as a result of the faster degradation of the second kind of polypeptide.

The invention also provides a recombinant microbial cell as defined above, comprising a gene coding for a first kind of polypeptide. Such a cell can be a bacterium of a Gram-negative bacterial species including *Enterobacteriaceae* spp., *Hemophilus* spp., *Vibrionaceae* spp. and *Pseudomonadaceae* spp or it can be of a Gram-positive bacterial species such as a *Bacillus* species or lactic acid bacterial species, a fungal cell including a yeast cell, an animal cell including a human cell and an insect cell, and a plant cell.

As also mentioned above, the invention pertains in another aspect to a method of limiting the survival of a cell population in a first or a second environment, which method comprises as the first step that the cells are transformed with a gene coding for a cytotoxic polypeptide, which gene is selected from the group consisting of the gene coding for the *E. coli* K-12 RelE polypeptide, the gene coding for the plasmid F CcdB polypeptide, the gene coding for the plasmid R1 PemK polypeptide, the gene coding for plasmid RP4 ParE polypeptide, the gene coding for the prophage P1 Doc polypeptide and a gene coding for a functionally equivalent polypeptide for anyone of said polypeptides.

In a specific embodiment of such a method, the survival of the cell population is limited in a first environment in which the gene is expressed whereby the cell population is contained in said first environment. In another embodiment, the survival of the cell population is not limited when present in a first environment, which first environment could change to a second environment physically and/or chemically distinct from the first environment, in which first environment the gene whose expression results in the formation of a cytotoxically active polypeptide is not expressed, but the survival of which cell population is limited when transferred to a second environment or when present in a physically and/or chemically changed first environment, where the gene is expressed.

In a still further embodiment of the above method, the survival of a cell population is being limited by providing in the cells a gone coding for a cytotoxic polypeptide which is operably linked to a DNA sequence encoding an antitoxin repressor substance which can undergo a decay when said cells are released to the outer environment to an extent whereby the repressor substance is converted to a non-functional form, whereby as a result of said decay, the function of the cells of the population will be gradually limited.

In yet another aspect of the invention, there is provided a method of containing an extrachromosomal recombinant replicon to a first kind of cell, where said replicon is naturally transferable to a second kind of cell, which method comprises as the first step providing on the recombinant extrachromosomal replicon a gene whose expression results in the formation of a cytotoxic polypeptide selected from the group consisting of the E. coli K-12 RelE polypeptide, the plasmid F CcdB polypeptide, the plasmid R1 PemK polypeptide, the plasmid RP4 ParE polypeptide, the prophage P1 Doc polypeptide and a functionally equivalent polypeptide for anyone of said polypeptides.

In one specific embodiment of such a method the gene product which inhibits the expression of the expression of the gene coding for the polypeptide or the cell function-limiting effect of the polypeptide is selected from the E. coli relB polypeptide, the plasmid F CcdA polypeptide, the plasmid R1 Peml polypeptide, the plasmid RP4 ParD polypeptide, the prophage P1 Phd polypeptide and a functionally equivalent polypeptide of anyone of such polypeptides.

The invention also provides a method as defined above of stochastically limiting in an environment the survival of a cell population. Such a method is particularly useful in the containment of recombinant cells which are to released to the outer environment or the animal or human body.

The invention will now be described in further details in the following examples and the drawings wherein FIG. 1 illustrates $relB_{K-12}$::lacZ and $relE_{K-12}$::lacZ translational fusions. Shown are relevant parts of the lacZ reporter plasmids pKG4001 (carrying a $relB_{K-12}$::lacZ fusion) and pKG4002 (carrying a $relE_{K-12}$::lacZ fusion). Numbers to the right in the Figure indicates lacZ expression levels in Miller units. The low expression level of relE::lacZ in pKG4002 is, in part, due to the presence of an intact relB gene located on the plasmid. The relB gene product represses the relBE promoter c. 130-fold;

FIG. 2 illustrates in vitro translation of $relBE_{P307}$-carrying plasmids. Lane 1: pBR322; lane 2: pHA402 (pBR322-relB$^+$); lane 3: pHA403 (pBR322-relBE+); lane 4: pBR322; lane 5: pHA100 (pBR322-E11 contains the P307 relBE genes in their natural context); lane 6: pKG325; lane 7: pHA110 (pBR325-relB$^+$);

FIG. 3 shows the structure of expression plasmid pNDM220. The plasmid is a mini-R1 vector whose copy number is amplifiable at 42° C. due to the insertion of the temperature inducible λ $P_R$ promoter upstream of the replication control region. The plasmid also carries the $Cl_{857}$ temperature-sensitive allele of the Cl repressor. Genes shown are copB (copy number control), repA (initiation of replication), parM and parR (plasmid stability loci), bla (β-lactamase) and lacI$^q$. The plasmid contains the LaCl regulated pA1/O4/O3 promoter upstream of a multiple cloning site that contains unique BamHI and EcoRI restriction sites. Thus genes inserted downstream of the promoter are inducible with IPTG;

FIG. 4 illustrates cell killing by $relE_{K-12}$ and anti-killing by $relB_{K-12}$. Shown are optical density at 450 nm and viable counts as function of time for strains MC1000/pMG223 (relE$^+$) (A, B), MC1000/pMG223/pMG2201 (relB$^-$ control plasmid) (C, D) and MC1000/pMG223/pMG2202 (relB$^+$ plasmid) (E, F). At time zero, transcription of relE on plasmid pMG223 was induced by the addition of IPTG (1 mM). Filled symbols indicate that IPTG was added. As seen from (E) and (F), the presence of relB on a second plasmid counteracted relE mediated cell killing;

FIG. 5 shows the structure of expression plasmid pBAD33. The plasmid is a medium copy number pACYC-derived vector. The plasmid carries the arabinose inducible pBAD-promoter and the araC gene of E. coli. Thus upon addition of arabinose to pBAD33 containing cells, genes inserted downstream of pBAD are transcriptionally induced. Genes shown in the Figure are: pACYC-ori: origin of replication; CM(R): gene encoding chloramphenicol acetyl transferase; bla': truncated (nonfunctional) gene encoding β-lactamase; mRNA1 encodes AraC activator protein; pBAD: arabinose-inducible promoter;

FIG. 6 A/B illustrates cell killing by $RelE_{P307}$ and anti-killing by $RelB_{P307}$. Shown are optical density at 450 nm (A,C) and viable counts (B, D) as a function of time for strains MC1000/pHA810/pBR322 (A, B) or MC1000/pHA810/pHA110 (carrying $relB_{P307}$). At time zero, transcription of $relE_{P307}$ on plasmid pHA810 was induced by the addition of arabinose (0.02%). Filled symbols indicate that arabinose was added. As seen from (C) and (D), the presence of $relB_{P307}$ on a second plasmid counteracted $relE_{P307}$ mediated cell killing;

FIG. 10 is the DNA sequence of the $relBE_{Sp2}$ locus of S. pneumoniae;

EXAMPLES

Materials and Methods (i) Bacterial Strains

Figure 1:
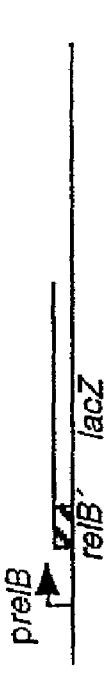

The E. coli K-12 strain MC1000 (Casadaban and Cohen, 1980) which contains a chromosomal copy of the relBE genes was used as the standard cloning strain and when a chromosomal copy of the relB operon was required. The E. coli K-12 strain JS115 (leu, thy, thi, supE, ΔrelB), which contains a deletion covering the entire relB operon was provided by Olle Karlström. The latter strain was used for the regulatory studies of relBE.

(ii) Plasmids Used

Plasmid pOU253 is a mini-R1 based translational fusion vector carrying the lacZ gene of pNM482 (Minton, 1984).

The fusion vector is segregationally stable due to the presence of the parA system of plasmid R1 (Dam and Gerdes, 1994).

Plasmid pNDM220 is a low copy-number mini-R1 expression vector carrying a multiple cloning site (mcs) placed between the LacI regulated pA1/O4/O3 promoter (Lanzer and Bujard, 1988) and two transcriptional terminators.

pNDM220 was deposited on 30 Apr. 1998 under the Budapest Treaty with the DSMZ-Deutsche Sammlung von Mikroorganismen und Zellkulturen GmbH under the accession No. DSM 12157.

Plasmid pBD2430 (+388-+1899) is a pUC18 derivative carrying the complete relBE operon and gene IV located downstream of relF (Olle Karlström, unpublished). The relevant *E. coli* DNA present in pBD2430 is shown in Table 1.1 below.

pBD2430 was deposited on 30 Apr. 1998 under the Budapest Treaty with the DSMZ-Deutsche Sammlung von Mikroorganismen und Zellkulturen GmbH under the accession No. DSM 12161.

(iii) Plasmids Constructed pKG4001: pBD2430 was digested with EcoRI and XhoI and the fragment carrying the relB promoter (Table 1.1) was inserted into pOU253 producing an in-frame translational fusion between $relB_{K-12}$ and lacZ. Thus, pKG4001 carries a $relB_{K-12}$::lacZ translational fusion.

pOU253 was deposited on 30 Apr. 1998 under the Budapest Treaty with the DSMZ-Deutsche Sammlung von Mikroorganismen und Zellkulturen GmbH under the accession No. DSM 12158.

pKG4002: pBD2430 was digested with EcoRI and Bst11071 and the resulting fragment was inserted into pOU253 producing an in frame translational fusion between $relE_{K-12}$ and lacZ. Thus pKG4002 carries an intact $relB_{K-12}$ gene and a $relE_{K-12}$::lacZ translational fusion.

pMG223: $relE_{K-12}$ was amplified by PCR on pBD2430 with primers relE1B (5'-CCCCGGATCCATAAGGAGTTT-TATAAATGGCGTATTTTCTGGATTTTGACG, SEQ ID NO:1) containing the parA Shine & Dalgarno (Gerdes and Molin, 1986) and relE2 (5'-CCCCCCTCGAGGTCGACT-CAGAGAATGCGTTTGACCGC-3', SEQ ID NO:2). The resulting $relE_{K-12}$ carrying fragment was inserted into pNDM220 using the BamHI and SalI restriction sites. Plasmid pMG223 expresses $RelE_{K-12}$ upon addition of IPTG.

pMG2201: this plasmid contains the EcoRI-Eco47III fragment from pBD2430 inserted between the EcoRI and ScaI sites of pBR322. Plasmid pMG2201 carries the $relB_{K-12}$ promoter and the 5' part of the $relB_{K-12}$ gene.

pMG2202: pBD2430 was digested with EcoRI and Bst11071 and the $relB_{K-12}$-carrying fragment was inserted into pBR322 EcoRI-ScaI. The resulting plasmid carries the relB promoter and $relB_{K-12}$.

pHA100: Plasmid pNZ945 is a pBS(+) derivative that carries a 4.3 kb EcoRI fragment from plasmid P307. This fragment encodes the RepFIB replicon and the relBE genes of P307 (Saul et al., 1989). The 4.3 kb EcoRI fragment (designated E11) of pNZ945 was purified and restricted with PstI. The resulting 2.2 kb EcoRI-PstI fragment was inserted into pBR322 restricted also with EcoRI and PstI. The pBR322-derived plasmid carrying the 2.2 kb EcoRI-PstI fragment was designated pHA100. Plasmid pHA100 codes for the entire relBE system from P307.

pNZ945 was deposited on 30 Apr. 1998 under the Budapest Treaty with the DSMZ-Deutsche Sammlung von Mikroorganismen und Zellkulturen GmbH under the accession No. DSM 12160.

pHA110: The 2.2 kb EcoRI-PstI fragment of pHA100 was purified and digested with ApoI (EcoRI isoschizomer). The resulting EcoRI-ApoI DNA fragment (+1 to +1122) was inserted into the EcoRI site of pKG325 which was constructed as follows: Plasmid pBR325 was restricted with PstI, which has a unique recognition site in the plasmid. The resulting vector DNA fragment was made blunt ended with T4 DNA polymerase according to the manufacturer's instructions, and religated. Transformants that were resistant to chloramphenicol and tetracycline, but sensitive to ampicillin were selected. Thus, pKG325 is a TcR, CmIR and ApS derivative of pBR325.

pKG325 was deposited on 30 Apr. 1998 under the Budapest Treaty with the DSMZ-Deutsche Sammlung von Mikroorganismen und Zellkulturen GmbH under the accession No. DSM 12159.

Plasmid pHA110 contains the relB promoter ($prelB_{P307}$) and gene $relB_{P307}$.

pHA205: Plasmid pHA205 is a derivative of the low copy-number mini-R1 expression vector pNDM220 that contains the relB gene from P307. The PCR fragment generated from pNZ945 using primers RelB-P307/1: 5'-CCCCCGGATC-CAGTCTTGAAAGGTGGC-3' (SEQ ID NO: 3) and RelB-P307/2: 5'-CCCCCGAATTCTCATAGGTATTTATCCAG-3' (SEQ ID NO:4) was restricted with BamHI and EcoRI and inserted downstream of the pA1/04/03 promoter of pNDM220. pHA210: Gene $relE_{P307}$ was PCR-amplified from pNZ945 with the primers: relE-p307/3 (5'-CCCCG-GATCCAGATCTGGATAAATACC, SEQ ID NO:5) and relE-P307/2 (5'-CCCCCGAATTCGTAACTTTCTGTGTT-TATTGC, SEQ ID NO:6). The resulting PCR DNA fragment was restricted with BamHI and EcoRI and inserted into pNDM220 also restricted with BamHI and EcoRI. Plasmid pHA210 (+1089 to +1417) is thus a mini-R1 derivative carrying a pA1/O4/O3::$relE_{P307}$ gene fusion which renders $relE_{P307}$ inducible with IPTG.

pHA215: Genes $relBE_{P307}$ were PCR-amplified from pNZ945 with the primers RelB-P307/1 (5'-CCCCCGGATC-CAGTCTTGAAAGGTGGC, SEQ ID NO:3) and relE-P307/2 (5'-CCCCCGAATTCGTAACTTTCTGTGTT-TATTGC, SEQ ID NO:6). The resulting PCR-generated DNA fragment was restricted with BamHI and EcoRI and inserted into pNDM220 also restricted with BamHI and EcoRI. Plasmid pHA215 (+840 to +1417) is thus a mini-R1 derivative carrying a pA1/O4/O3::$relBE_{P307}$ gene fusion rendering the $relBE_{P307}$ genes inducible with IPTG.

pHA402: A PstI-AatII fragment from plasmid pHA205, which carries $lacI^q$ and the pA1/O4/O3::$relB_{P307}$ gene fusion was inserted into pBR322 also restricted with PstI and AatII. Thus, the high copy-number plasmid pHA402 contains a $relB_{P307}$ gene which is inducible with IPTG.

pHA403: A PstI-AatII fragment from plasmid pHA215, which carries $lacI^q$ and the pA1/O4/O3::$relBE_{P307}$ gene fusion was inserted into pBR322 also restricted with PstI and AatII. Thus, the high copy-number plasmid pHA403 contains the $relBE_{P307}$ genes which can be conditionally induced by the addition of IPTG.

pHA810: A DNA fragment encoding $relE_{P307}$ was generated by PCR using primers relE-P307/4 (5'-CCCCCGAGCT-CAGATCTGGATAAATACC, SEQ ID NO:7) and relE-P307/5 (5'-CCCCCGCATGCGTAACTTTCTGTG TTTATTGC, SEQ ID NO:8). The fragment was digested with SaCl+SphI and inserted into the expression plasmid pBAD33 also digested with SaCl+SphI. The resulting plasmid, pHA810 (+1089-+1417), contains the pBAD::$relE_{P307}$ gene fusion that renders $relE_{P307}$ inducible with arabinose.

An overview of the bacterial strains and plasmids used herein is shown in Table 0.1 below.

TABLE 0.1

Bacterial strains and plasmids

| Strains | genotypes | Reference/Source |
|---|---|---|
| MC1000 | Δlac leu ara | Casadaban & Cohen, 1980 |
| JS115 | ΔrelB leu thy thi supE | J. P. Bouche, unpublished |

| Plasmids | Replicon | Resistance[a] | relBE co-ordinates[b] | Reference/Source |
|---|---|---|---|---|
| pOU253 | mini-R1 | $Ap^R$ | none | lab. collection |
| pBAD33 | pACYC | $Cml^R$ | none | Guzman et al., 1995 |
| pNDM220 | mini-R1 | $Ap^R$ | none | Gotfredsen & Gerdes, 1998 |
| pBR322 | ColE1 | $Ap^R$, $Tc^R$ | none | Bolivar et al., 1978 |
| pKG325 | pBR325 | $Tc^R$ | none | lab. collection |
| pBD2430 | pUC | $Ap^R$ | +388-+1899 | Olle Karlström collection |
| pNZ945 | pUC | $Ap^R$ | +1-+4298 | Saul et al., 1989 |
| pKG4001 | mini-R1 | $Ap^R$ | +388-+596 | Gotfredsen & Gerdes, 1998 |
| KG4002 | mini-R1 | $Ap^R$ | +388-+921 | Gotfredsen & Gerdes, 1998 |
| pHA100 | pBR322 | $Tc^R$ | +1-+2198 | Grønlund & Gerdes, 1998 |
| pHA110 | pBR325 | $Tc^R$ | +1-+1122 | Grønlund & Gerdes, 1998 |
| pHA205 | mini-R1 | $Ap^R$ | +840-+1111 | Grønlund & Gerdes, 1998 |
| pHA210 | mini-R1 | $Ap^R$ | +1089-+1417 | Grønlund & Gerdes, 1998 |
| pHA215 | mini-R1 | $Ap^R$ | +840-+1417 | Grønlund & Gerdes, 1998 |
| pHA402 | pBR322 | $Tc^R$ | +840-+1111 | Grønlund & Gerdes, 1998 |
| pHA403 | pBR322 | $Tc^R$ | +840-+1417 | Grønlund & Gerdes, 1998 |
| pHA810 | pACYC | $Cml^R$ | +1089-+1417 | Grønlund & Gerdes, 1998 |
| pMG223 | mini-R1 | $Ap^R$ | +733-+1020 | Gotfredsen & Gerdes, 1998 |
| pMG2201 | pBR322 | $Tc^R$ | +388-+597 | Gotfredsen & Gerdes, 1998 |
| pMG2202 | pBR322 | $Tc^R$ | +388-+921 | Gotfredsen & Gerdes, 1998 |

[a] $Tc^R$, tetracycline resistance; $Ap^R$, ampicillin resistance; $Cml^R$, chloramphenicol resistance.
[b] Co-ordinates refer to Table 1.1 (relBE$_{K-12}$, pMG-plasmids) or Table 1.2 (relBE$_{P307}$, pHA-plasmids)

(iv) Growth Media and Antibiotics

The growth medium was LB medium (Bertani, 1951) or A+B minimal medium (Clark and Maaløe, 1967) supplemented with 0.2% glucose and 1% casamino acids. For growth on solid media, LA-plates were used. LA is LB containing 15 g agar per liter. All media were supplemented with 50 μg/ml thymine for growth of the strain JS11507-05-99ΔrelBEF$_{K-12}$. Antibiotics were added at the following concentrations: ampicillin, 30 μg/ml, and tetracycline, 10 μg/ml. When indicator plates were used X-gal (5-Bromo-4-chloro-3-indolyl-β-D-galactoside) was added to a final concentration of 40 μg/ml.

(v) Conditions of Cell Growth.

Cells were diluted in LB+antibiotics from an overnight culture to an $OD_{450}$ of 0.005. The cultures were then grown at 37° C. until an $OD_{450}$ of 0.4 and then diluted to an $OD_{450}$ of 0.01 in 37° C. LB containing 1 mM IPTG and antibiotics. Samples for $OD_{450}$ measurements and viable counts were taken at the time points indicated. Viable counts were made by plating dilutions of the cultures onto LA plates containing the proper antibiotics.

(vi) Coupled in vitro Transcription and Translation.

The reactions were performed using the E. coli S30 Extract System For Circular DNA as described by the supplier (Promega Corp.). 4 μg of DNA was used in all reactions. The reactions were run on a 16% Tricine-SDS-PAGE gel essentially as described by Schäger and von Jagow (1987).

(vii) β-galactosidase Assays.

β-galactosidase assays were performed essentially as described by Miller (1972).

(viii) Homology Search.

BLAST searches were performed at the GENESTREAM BLAST network server CRBM Montpellier, France. Standard conditions were used except that the blosum 80 matrix was used.

Example 1

The Occurrence of relBE Operons in Bacteria and Archae 1.1. Nucleotide Sequence of the relBE Operon of E. coli K-12

The DNA sequence of the relBE operon from E. coli K-12 is shown in Table 1.1. In this Table the transcriptional start site of the relBE mRNA is indicated with two asterisks (heterogeneity). IR indicates inverted repeats in the promoter and terminator regions. Start codons and stop codons are shown in bold. The transcriptional termination point (ttp) of the relBE mRNA is also indicated with a vertical arrow. The DNA sequence is from Bech et al., 1985.

By visual inspection of the relB$_{K-12}$ and relE$_{K-12}$ genes there was found striking similarity with the so-called "proteic plasmid stabilization systems" as described by Jensen and Gerdes (1995). First, relE$_{K-12}$ codes for a very basic protein (RelE$_{K-12}$; pI=9.7) of 95 amino acids (aa), and relB$_{K-12}$ codes for a very acidic protein (RelB$_{K-12}$; pI=4.8) of 79 aa.

The sequences of proteins RelB$_{K-12}$ and RelE$_{K-12}$ are shown in Tables 1.5 and 1.6, respectively. These Tables show multiple sequence alignments of the RelB and RelE gene families. Conserved amino acids at a given position are shown with shading as follows: two amino acids are considered conserved if they both belong to one of the following groups: group 1: D and N; group 2: E and Q; group 3: S and T; group 4: K and R; group 5: F, Y and W; group 6: L, I, V and M. Light grey shading indicates 60-80% conservation, dark grey indicates 80-99% conservation and black indicates 100% conservation. Note in Table 1.6 the fully conserved glycine at position 69 (G in consensus line) and the fully conserved arginine at position 79 (R in consensus line). The entrez database accession numbers of the protein sequences are given in Tables 1.3 and 1.4.

The relB$_{K-12}$ and relE$_{K-12}$ genes are co-transcribed with a third gene, relF (also denoted orf-3 or hokC), which is homologous to the hok gene from plasmid R1 (Gerdes et al., 1986). The start site (i.e. the 5'-end) of the relBE mRNA was determined to be 31 nucleotides upstream of the relB$_{K-12}$ AUG start-codon (Bech et al., 1985) and was confirmed (M. Gotfredsen and K. Gerdes, 1998). Inverted arrows in the relBE promoter region (Table 1.1) indicate putative binding sites for regulators of transcription (i.e. the RelB$_{K-12}$ and RelE$_{K-12}$ proteins themselves).

The properties described above suggested that RelE could be a cytotoxin and that RelB could be an antitoxin which counteracts the toxicity elicited by RelE.

TABLE 1.1

DNA sequence of the relBE operon from *E. coli* K-12 (SEQ ID NO:9)

```
   1 CTTAATTTCA GGCCCCATCG GATCACACAT GGAGAGTTTT TATGAATAAC

51 CCCGTCTGTC TTGATGACTG GTTGATTGGC TTTAAAAGCT TGTTGACAGG

101 GGTAAACGTT CGGCAATAAT TTTCTGCCGC ATGCGGGTGT TGCATAAAAC

151 GTGTTACGTT CCTTTATCGA CAGGTCAGGT CACCGCTCAC CCGCCGACGA

201 GAAAGCAACA CTGACATGCT AAAGCAAAAA ATAGATGAAT AAGTTGAGTT

251 GTGCATATGT AGCCTGACCG TCACAAAGTA TATGGTGTCT GTACCAGTAA

301 GATGATGGCC GGACTCTTTA AAAACGAGCT GACCTGCACA ATACAGGATG

351 GACTTAGCAA TGGCTGCTCC TGGCACAAAG CGGACAGTGA TCACCGTTCT

401 TACGACTACT TTCTGACTTC CTTCGTGACT TGCCCTAAGC ATGTTGTAGT

**→relBEF mRNA                    relB start
 451 GCGATACTTG TAATGACATT TGTAATTACA AGAGGTGTAA GACATGGGTA
          ---- ---- --→IR←-- ------- --

501 GCATTAACCT GCGTATTGAC GATGAACTTA AGCGCGTTC TTACGCCGCG

551 CTTGAAAAAA TGGGTGTAAC TCCTTCTGAA GCGCTTCGTC TCATGCTCGA

601 GTATATCGCT GACAATGAAC GCTTGCCGTT CAAACAGACA CTCCTGAGTG

651 ATGAAGATGC TGAACTTGTG GAGATAGTGA AGAACGGCT TCGTAATCCT

End relB     Start relE
 701 AAGCCAGTAC GTGTGACGCT GGATGAACTC TGATGGCGTA TTTTCTGGAT

751 TTTGACGAGC GGGCACTAAA GGAATGGCGA AAGCTGGGCT CGACGGTACG

801 TGAACAGTTG AAAAAGAAGC TGGTTGAAGT ACTTGAGTCA CCCCGGATTG

851 AAGCAAACAA GCTCCGTGGT ATGCCTGATT GTTACAAGAT TAAGCTCCGG

901 TCTTCAGGCT ATCGCCTTGT ATACCAGGTT ATAGACGAGA AAGTTGTCGT

951 TTTCGTGATT TCTGTTGGGA AAAGAGAACG CTCGGAAGTA TATAGCGAGG

End relE
1001 CGGTCAAACG CATTCTCTGA ACCAAAGCAT GACATCTCTG TTTCGCACCG

Start hokC (relE)
1051 AAGGTGACAC TTCTGCTTTG CGTTGACAGG AGAAGCAGGC TATGAAGCAG

1101 CAAAAGGCGA TGTTAATCGC CCTGATCGTC ATCTGTTTAA CCGTCATAGT

1151 GACGGCACTG GTAACGAGGA AAGACCTCTG CGAGGTACGA ATCCGAACCG

End hokC
1201 ACCAGACGGA GGTCGCTGTC TTCACAGCTT ACGAACCTGA GGAGTAAGAG

1251 ACCCGGCGGG GGAGAAATCC CTCGCCACCT CTGATGTGGC AGGCATCCTC

1301 AACGCACCCG CACTTAACCC GCTTCGGCGG GTTTTTGTTT TTATTTTCAA
                        ---- -- IR ---- - ttp 1351 CGCGTTTGAA GTTCTGGACG GTGCCGGAAT AGAATCAAAA ATACTTAAGT
           (data base accesion number X02405)
```

TABLE 1.3 relE homologues from Gram-positive and Gram-negative bacteria and Archae

| Bacterial species | entrez accession | gene[a] | Number of aa | MW (kD) | pI |
|---|---|---|---|---|---|
| Gram-negative bacteria: | | | | | |
| E. coli K-12 | 132284 | relE$_{K-12}$ | 95 | 11.2 | 9.7 |
| E. coli K-12 | 984581 | relE$_{SOS}$[b] | 92 | 10.8 | 9.5 |
| E. coli plasmid P307 | 516611 | relE$_{P307}$ | 95 | 11.2 | 9.9 |
| H. influenzae | 1175293 | relE$_{Hi}$ | 102 | 11.9 | 6.7 |
| V. cholera | 396846 | relE$_{Vc}$ | 96 | 11.2 | 9.9 |
| H. pylori | 2314031 | relE$_{Hp}$ | 88 | 10.4 | 7.9 |
| Synechosystis | 1653777 | relE$_{Sy}$ | 120 | 13.7 | 7.9 |
| Gram-positive bacteria: | | | | | |
| B. thuringiensis | 520407 | relE$_{Bt}$ | 74 | 8.6 | 9.7 |
| M. tuberculosis#1 | 2612811 | relE$_{Mt1}$ | 87 | 10.2 | 11.0 |
| M. tuberculosis#2 | 2695832 | relE$_{Mt2}$ | 97 | 11.1 | 9.5 |
| Archae: | | | | | |
| M. jannaschii#1 | 1498833 | relE$_{Mj1}$ | 90 | 11.0 | 10.2 |
| M. jannaschii#2 | 1499953 | relE$_{Mj2}$(*) | 88 | 10.6 | 10.0 |
| M. jannaschii#3 | 1591583 | relE$_{Mj3}$(*) | 91 | 11.1 | 10.1 |
| A. fulgidus#1 | 2648176 | relE$_{Af1}$ | 87 | 10.6 | 10.3 |
| A. fulgidus#2 | 2649499 | relE$_{Af2}$ | 92 | 11.0 | 9.9 |
| A. fulgidus#3 | 2649496 | relE$_{Af3}$ | 85 | 10.0 | 10.0 |
| A. fulgidus#4 | 2649514 | relE$_{Af4}$ | 86 | 10.2 | 9.9 |

[a]relE homologues marked with (*) are not located adjacent to a relB partner
[b]The relBE$_{SOS}$ system of E. coli K-12 contains a LexA binding-site in the promoter region (Lewis et al., 1994)

TABLE 1.4 relB homologues from Gram-positive and Gram-negative bacteria and Archae

| Bacterial species | entrez accession | gene[a] | Number of aa | MW (kD) | pI |
|---|---|---|---|---|---|
| Gram-negative bacteria: | | | | | |
| E. coli K-12 | 132283 | relB$_{K-12}$ | 79 | 9.1 | 4.8 |
| E. coli K-12 | 984582 | relB$_{SOS}$[b] | 86 | 9.4 | 5.2 |
| E. coli K-12 | 984588 | relB$_{K-12,2}$(*) | 97 | 11.2 | 5.5 |
| E. coli plasmid P307 | 516610 | relB$_{P307}$ | 83 | 9.2 | 4.4 |
| S. typhimurium | 731639 | relB$_{St}$(*) | 68 | 7.6 | 5.3 |
| H. influenzae | 1573712 | relB$_{Hi}$ | 98 | 11.0 | 4.7 |
| V. cholera | 396847 | relB$_{Vc}$ | 82 | 8.9 | 4.4 |
| H. pylori | 2314037 | relB$_{Hp}$ | 95 | 11.4 | 9.8 |
| Synechosystis | 1653776 | relB$_{Sy}$ | 86 | 9.9 | 4.7 |
| Gram-positive bacteria: | | | | | |
| B. thuringiensis | 520406 | relB$_{Bt}$ | 85 | 10.1 | 4.5 |
| M. tuberculosis#1 | 2612810 | relB$_{Mt1}$ | 93 | 10.2 | 4.6 |
| M. tuberculosis#2 | 2695833 | relB$_{Mt2}$ | 89 | 9.8 | 5.1 |
| Archae: | | | | | |
| M. jannaschii#1 | 1498832 | relB$_{Mj1}$ | 82 | 9.6 | 4.5 |
| A. fulgidus#1 | 2648190 | relB$_{Af1}$ | 65 | 7.8 | 4.8 |
| A. fulgidus#2 | 2649516 | relB$_{Af2}$ | 62 | 7.4 | 4.3 |
| A. fulgidus#3 | 2649510 | relB$_{Af3}$ | 72 | 8.5 | 4.5 |
| A. fulgidus#4 | 269513 | relB$_{Af4}$ | 57 | 6.7 | 4.1 |

[a]relB homologues marked with (*) are not located adjacent to a relE partner.
[b]The relBE$_{SOS}$ system of E. coli K-12 contains a LexA binding-site in the promoter region (Lewis et al., 1994).

Table 1.5. Alignment of *relE* homologues from Gram-positive and Gram-negative bacteria and *Archae* (SEQ ID NOS:10-26)

Table 1.6. Alignment of *relB* homologues from Gram-positive and Gram-negative bacteria and *Archae* (SEQ ID NOS:27-43)

```
                       *          20         *          40         *          60         *          80         *
relB-SOS    : ------------MAANAFVRARIDLKNQAADVLAGMGLTISDEVRIT-LTKVAREKALPFDL--REPNGLTIQSIKN---------------SE : 66
relB-VC     : ------------MTTRILADWAASTTFKANPMKVATSAFGAPVAVN-------RNEPAFYCVP--ASTYGIMDKLED---------------LE : 61
relB        : ------------MPNIILSDTSASKKNPMATVSAGDGFPVAIN--------RNQPAFYCVP--AELYRKMLDALDD---------------QE : 61
relB-Mt1    : MRILPISTIKGENEFADLSSTQDIITTKNGAPAAVGAD-EWESLQETLYWLAQ--PGIRSIAEADAD---------------IA : 72
relB-Mt2    : MAVVPLGEVRNRLSEYNAELTHERITITRHGHPAAVISAD-DLASIEETLEVLRT--PGASAIREGLAD---------------VA : 72
relB-K12_2  : MHRILAEKSVNHIERKNPAKYFID---QPVAVS-------NNRPAGYLLS--ASAFALMDMLAEQEEKKPIKARFRPSAARLE : 74
relB-St     : MFMRTVNYSEARONLAEVLESAVTGGPVTITR--------RGHKSAVIIS--AEEFRYQTARMD---------------D : 56
relB-coli   : ------------MGSNLREDELKARSYAALEKMGVTPSEALR---------LMLEYIADNE--RLPFKQTLLSDED---------------AE : 57
relB-HI     : ------------MALTNSSFRITVETKLRAYQVIEQYGLTPSQFNMF-LAQIAKTRSIPVDLNYLRPNKETLAAIDELD---------------SGNAES : 75
relB-MJ     : ------------MLNINKEAQIETINELKKLRDEISERIEKLEK-------LLKLKALAIPE--BEFEDYEELIED---------------VK : 61
relB-Af1    : ------------MNEALREIYSKKITREKIEQLEELLIIPAEKVSEEELLEIRKLKEESLKGEHVDWDLKRELGV----------------LE : 65
relB-Af3    : ------------MKVLLDIENFROLEKRRGELEELKDEILFS------DAEFIDSIQRGLSDLEGRSKVCSN---------------LE : 63
relB-Af2    : ------------MEVIQISKDELERKFKEVLIKALMEITPYVSDE------EQEEIDKIAGKPDEYEGEFEEWHGK---------------LE : 62
relB-Af4    : ------------MDIQVEKQAREJLREELPSILKEVILSTIPPD---------EPEADEKQFVDEEINDDYVKFDE---------------LE : 57
relB-Hp     : ------------MPNTTNKDYTKYSRQLFSFLNSIKTKQKRALEKLKEIQAQKQRIKKALQFKALNLTENGVTIEEERE---------------ILARAK : 74
relB-sy nec : ------------MMRAFEVATVKDSKQLLLDSDLHWNTSRVKVIILESD--ELASKGSEFDP-DDTPVEIKVSLRK---------------AL : 65
relB-BT     : ------------MAIRKEYRLDHDQQDEKAAFDFLEFLVQRSRRKP----KEWEKIDMADPDHEPLSTQELEQLNS---------------E : 65

100          *
relB-SOS    : AGIDVHKAKDADDLFDKLGI---- : 86
relB-VC     : LLAIAKERLSEDSVSVNIDDL--- : 82
relB        : LVKLVAERSNQPLHDVDLDKYL-- : 83
relB-Mt1    : SGRTYGEDEIRAEFGVPRRPH--- : 93
relB-Mt2    : AGRFVSNDEIRNRYTAR------- : 89
relB-K12_2  : EITRRAEQYLNDMTDDDFNDFKE- : 97
relB-St     : EFAAIMAVHGNE------------ : 68
relB-coli   : LVEIVKERLRNPKPVRVTLDEL-- : 79
relB-HI     : FFIEASENYSAEEFTKRILNGGQ- : 98
relB-MJ     : KSLDKKETVPAEEALKELGLL--- : 82
relB-Af1    : ------------------------ : -
relB-Af3    : EVKKLFEDI--------------- : 72
relB-Af2    : ------------------------ : -
relB-Af4    : ------------------------ : -
relB-Hp     : DTKNRLCFKSIEDFKKHCENL--- : 95
relB-sy nec : EEYKQGKRIPVENMWEGIDVE--- : 86
relB-BT     : EGYVSGEDAKREFGLQIDLP---- : 85
```

1.2. Nucleotide Sequence of the relBE Operon of Plasmid P307

By database searching it was found that the *E. coli* plasmid P307 codes for a gene system which exhibits both structural and sequence similarity with the *E. coli* relBE genes described above.

The DNA sequence of the relBE$_{P307}$ genes is shown in Table 1.2. The transcriptional start site of the relBE mRNA is indicated with an asterisk, and the −10 and −35 sequence elements of the relBE promoter are underlined. The Shine & Dalgarno sequence of the relB and relE genes are doubly underlined. The DNA sequence is from Saul et al., 1989.

Again, relE$_{P307}$ codes for a very basic protein of 95 aa (pI=9.9), and relB$_{P307}$ codes for a very acidic protein of 83 aa (pI=4.4), see Tables 1.3 and 1.4. The protein sequences of RelE$_{P307}$ and RelB$_{P307}$ are also shown in Tables 1.5 and 1.6, respectively. The start site (i.e. the 5'-end) of the relBE$_{P307}$ mRNA was determined to be located 27 nucleotides upstream of the relB$_{P307}$ AUG start codon. Inverted arrows in the relBE$_{P307}$ promoter region (Table 1.2) indicate putative binding sites for regulators of transcription (i.e. the RelB$_{P307}$ and RelE$_{P307}$ proteins).

TABLE 1.2

DNA sequence of the relBE operon from the
*E. coli* plasmid P307 (SEQ ID NO:44)

```
 301 GAGTATCATA TTAGGATACG GGTGGGTGAC GCCCACCTCT GGCATAGAAC

351 GGACATTCAT TGATGCCATG CCAGAATGGA CGTTCAGGTT ATTCCGTCCA

401 GTTCTGCTGG CAACGCGAGA TCTCCCCTGG TATAGTGATG CCACAGCAAA

451 GCGCTCAAAC AGGGATAATA TGATGGAAAT CAAGGCTCAA CAGTTTTGTC

501 ACATCAACGG GGCGGCAAGT CCTTACTGAC AACGGACAAC AAGGTATGGG

551 CGGCGTGGCG GGTATCGGTT CCACGACTGA AAAGCATCAG GGGCGCGTGG

601 CGGAAGCGAT TTTTGCGAAC TGCGCGGAAC TGGATAACGA CCAGCTTAAC

651 GAGATCATCG AGTGGGTTCG GCTCTATCAG CGCTGAATGC CACTATCAGG

701 CTGCGCAAGC GGCCTTTTTT ACGCCCCTTG TTTAATTCCC GCACTACCTG

-35
 751 GACGTTCAGG TGATTCTGTC CATCTGTACA AAAACAATA  AAAGACTTGT

-10            *→ relBEₚ₃₀₇ mRNA
 801 TAACAGGTCA TGTAAGGAGT ATCTTTGAGA CTGGTTAAAC AGTCTTGAAA SD       start relB
 851 GGTGGCCTAT GCCTAACATT ATTCTCAGTG ATACAAGCGC CAGTGTCAGC

901 GAGCTGAAGA AAAACCCGAT GGCGACAGTC AGCGCCGGTG ATGGTTTCCC

951 GGTCGCTATC CTGAACCGTA ATCAGCCTGC TTTCTACTGT GTACCCGCAG

1001 AGCTGTACGA AAAGATGCTT GATGCCCTAG ACGATCAGGA GTTGGTTAAA

SD
1051 CTGGTAGCCG AACGCAGCAA CCAACCGCTG CATGATGTAG ATCTGGATAA end relB/start relE
1101 ATACCTATGA GGTATCAGGT AAAATTCAGG GAAGATGCGC TGAAAGAGTG

1151 GCAAAAACTG GACAAGGCTA TTCAGCAACA GTTTGCGAAA AAGCTAAAAA

1201 AGTGCTGTGA CAATCCGCAT ATTCCTTCCG CAAAACTGCG TGGGATAAAG

1251 GACTGCTACA AAATAAAATT ACGTGCGTCA GGTTTTCGCC TGGTCTATCA

1301 GGTGATTGAC GAACAATTAA TTATCGCTGT TGTAGCTGTG GGTAAACGTG end relE
1351 AGCGCAGTGA CGTTTATAAT CTTGCCAGCG AAAGAATGAG ATAAAAGCAA

1401 TAAACACAGA AAGTTACTCT GGCGTTATGG GGTAATGCAA AGTATGAGTC

1451 GTAGAGGGAA TTGCCTGGAT AATTCGCCGA TGGAAAGAGT CTTTCGCAGC

1501 CTTAAAAGTG AATGGCTTCC GAAAGGTGGT TATGGTGATT TTAGCCATGC
                     (database accession number D426308)
```

1.3. Nucleotide Sequence and Proteins of a relBE Homologous Operon from *Bacillus thuringiensis*

Using BLAST database searching (Altschul et al., 1990) it was found that transposon Tn5401 from the Gram-positive organism *B. thuringiensis* contains, in one end or asymmetrically located, a two-component system which exhibits both structural and sequence similarity with the above described relBE systems from *E. coli*. This homology is surprising given that it has not previously been described that relBE-like genes are found in organisms other than *E. coli*.

The nucleotide sequence of the relBE operon from Tn5401 is shown in Table 1.7. In this Table the transcriptional start-site of the relBE mRNA is indicated with an asterisk (Baum, 1994). IR indicates inverted repeats in the relBE$_{Bt}$ promoter region. Start codons and stop codons are shown in bold. The Shine & Dalgarno sequence of the relB$_{Bt}$ gene is doubly underlined. The DNA sequence is from Baum et al., 1989.

The relE$_{Bt}$ gene codes for a very basic protein of 74 aa (pI=10.6) and the relB$_{Bt}$ gene codes for an acidic protein of 87 aa (pI=4.4). The protein sequences of RelE$_{Bt}$ and RelB$_{Bt}$ are aligned with the other RelE and RelB homologues in Tables 1.5 and 1.6, respectively. The modular, structural and physico-chemical similarities between the *B. thuringiensis* system and the *E. coli* systems suggested that the genes may exert similar functions in very different bacteria.

TABLE 1.7

DNA sequence of the relBE operon from the
Gram-positive organism *B. thuringiensis* (SEQ ID NO:45)

```
3701  CTCGTTTTTT CTGTTGGTAC AAACTTAATT GATTTTGAAT AATTTGTTTG

3751  TACCAGTCCT TTTTGCTTAG CCCAGTCAAA ATAACGTTTG ATTGAATTAA

3801  TGCGCCGGTT AATCGTAGAA GGTTTTAGTA ATCTTGTAAC TTGCATATGC

3851  CCTCGATATC GAGCAATAGT GCGAGCGGTA ACTTCTATTG GATGAAAAAG

3901  AGTATCCTCA GCATGTTTTC CCCACACATT TTCAAACCAA AATACAAAAT

3951  CTTTTAAATC ACTCGTATAT TCTTTTAGTG TTTTTGTATG CAAATCTCCT

4001  TCTTGAGATA AGCTAGAAAT AAAATCGGAA ATCAAAGATG TTGCTTGTAT

-35
4051  AGAAATTGTT TTAGTGGAAT GCATAAATAC CTCCTCTTTT ATTGACTTAC

-10            *→ relBEBt mRNA
4101  ATTAGCGGAC ATGATATTTT AATCTTATCA ATTATGTTAG CGGACATCAA 4151  ACATTTATTT TCCCACACTT CATGTCCACT AATATTAATT AGTGGACATT
                              --------- ---→ IR ←--- ---------

SD            Start relB
4201  TAAAACTATC TCGAAAGTAG GTGTAACACA TGGCTATTCG TAAAGATGAA

4251  TTGTATCGGT TAATTGATCA CCTGGATCAA CAAGATGAAA AAGCAGCATT

4301  TGACTTTTTA GAATTTCTTG TTCAACGGTC AAGAAGAAAA CCTAAAGAAT

4351  GGGAAAAAAT TGATATGGCA GATCCTGATC ATGAACCGCT GTCTACACAA

4401  GAGTTAGAAC AGTTAAACAG TGAAGAAGGA TATGTATCAG GGGAGGACGC

End relB    Start relE
4511  AAAACGTGAA TTCGGACTAC AAATTGATTT ACCATAAGTC CGCGGTGAAA

4501  TTTATTGCAA AGCAAGAAAA AGGGATTCAA AAAAGAATTG CAGAAGGATT

4551  GAAGGGACTT CTTAAGATTC CTCCTGAAGG AGATATTAAA AGTATGAAAG

4601  GTTACACAGA ACTATATCGA TTACGGATTG GAACCTTTCG AATTTTATTT

4651  GAAATAAATC ATGATGAGAA AGTCATATAC ATACAAGCAA TTGGAAATCG

End relE
4701  TGGTGACATC TATAAATAAG GCAAACATGC ATTTTTAAAA GAAAGGTCTT

4751  CTGAATCGAA GAACCTTCCT TTTTTGTGTG CGAATAATGT CCGCTAATGC

4801  TTGTTGCGTG ATTCTGTTCC ATTGCTACAC ATACCCC
      (database accession number U03554)
```

1.4. The Archaeon *Methanococcus jannaschii* Encodes a relBE Homologous System Again using database searching it was found that the completely sequenced genome of the methanogenic archaeon *Methanococcus jannaschii* codes for three relE homologous genes, one of which are located just downstream of relB homologous genes. This finding was surprising since, in many respects, archaeal organisms are more similar to eukaryotes than to bacteria (e.g. in their macromolecular synthesis apparatuses).

The DNA sequence of the relBE$_{Mj1}$ system is shown in Table 1.8. In this Table start codons and stop codons are shown in bold. The DNA sequence is from Bult et al., 1996.

Gene relE$_{Mj1}$ codes for a very basic polypeptide of 90 aa (pI=11.0) and gene relB$_{Mj1}$ codes for an acidic polypeptide of 82 aa (pI=4.4). The aa sequences of the RelE$_{Mj1}$ and RelB$_{Mj1}$ proteins are aligned with the other RelBE homologues in Tables 1.5 and 1.6, respectively. Thus, these basic similarities suggested that the relBE$_{Mj1}$ system may carry out similar or related functions in bacteria and archae. The properties of the second and third relE homologues of *M. jannaschii* are also given in Table 1.3. These comparisons show that *M. jannaschii* codes for one complete relBE homologous gene system and for two relE homologues without an adjacent relB partner.

1.5. relBE Homologous Genes are Ubiquitous in Prokaryotes

Further relBE homologous two-component systems were discovered. The corresponding RelB and RelE homologous proteins are aligned in Tables 1.5 and 1.6, respectively. It appears that relE homologous genes are present in a wide variety of Gram-negative bacteria (*E. coli, H. influenzae, V. cholera, H. pylori* and *Synechosystis*), in Gram-positive bacteria (*B. thuringiensis* and *M. tuberculosis*) and in Archae (*M. jannaschii* and *A. fulgidus*). Most strikingly, the archaeon *A. fulgidus* contains four complete relBE homologous gene systems.

A number of features become evident from the alignments of the proteins (Tables 1.5 and 1.6) and from the properties listed in Tables 1.3 and 1.4. First, all RelE homologues are basic with pH's around 8-10 whereas the RelB homologues are acidic with pI's about 4-5. Secondly, the RelE proteins are in general slightly larger (90-120 aa) than the RelB homologues (70-80 aa). Thirdly, the start codons of the relE genes are juxtaposed or even overlap with the stop codons of the linked relB partner, thus indicating translational coupling of

TABLE 1.8

DNA sequence of a relBE homologous gene system
from the archaeon *Methanococcus jannaschii*
(SEQ ID NO:46)

```
 751 CCGATACCGT TGCTGGAGAC ATAGCTGGAG CTTTGAAGGC GGAGAAGCTT

801 ATTTTAATAA CAGATGTTGA TGGAATAATG GATGATATAA ATAATCCAGA

851 GACGTTGCAT AGAAAATTAA CAGCTTCAGA ACTAAAAGAA ATGATAGAAG

901 ATGGAAGAAT AAAGGGAGGG ATGATTCCAA AGGCTGAAAG TGCCTTATAT

951 GCCTTAGAGC ATGGAGTTAA GAGCGTTCAT ATAATAAATG GAAAGATTCC

1001 TCATGCTTTG TTGTTGGAGA TATTTACAGA GGAGGGTATT GGGACGATGA

1031 TAACAAGAGA TTAAAGTTTT TATATTATAA ACTACTTAAG AATTAAAATA

Start relB$_{Mj1}$
1101 AGACAAATAA GGGGATAACT ATGCTCAATA TAAACAAAGA GATAGCACAA

1151 ATAGAAACTG AATTGAATGA ATTGAAAAAA TTGAGAGATG AAATCTCTGA

1201 AAGGATTGAA AAATTAGAAA TAAAGTTATT AAAATTGAAA GCATTAGCTA

1251 TTCCAGAGGA GGAATTTGAA GAGGATTATG AAGAAATTAT AGAAGATCTT

1301 AAAAAATCTC TGGATAAAAA AGAGACTGTG CCAGCAGAAG AGGCTTTGAA

End relB$_{Mj1}$/start relE$_{Mj1}$
1351 AGAATTGGGA TTATTATGAA GTTTAACGTT GAGATACATA AAAGAGTCTT

1401 AAAAGATTTA AAGGATTTGC CTCCCTCAAA CTTAAAGAAG TTTAAAGAAC

1451 TAATAGAAAC ATTAAAAACC AATCCCATTC CAAAAGAAAA ATTTGATATT

1501 AAAAGATTAA AAGGCAGTGA TGAGGTTTAT AGAGTTAGAA TTGGAAAATT

1551 TAGAGTTCAA TATGTTGTTT TATGGGATGA TAGAATAATA ATAATTAGAA

End relE$_{Mj1}$
1601 AGATAAGTAG AAGAGAAGGA GCTTATAAAA ATCCCTAAGC TATTAAAAAT

1651 TCTAATGGCT ACATTTTTAT ATCTCTTTTC TTAATTCAAA TAGAAAAAAC

1701 AGATTCGGCT GATACCATGA TTATTCTTTT AGATTTAAAT GGAACAATAG
         (database accession number U67464)
``` relE to relB. These properties suggest that the proteins could exert similar functions in very different organisms.

Example 2

Demonstration of Translation of the $relB_{K-12}$ and $relE_{K-12}$ Genes

Using the low copy-number lacZ fusion vector pOU253 (Table 0.1) in frame gene fusions between $relB_{K-12}$ and $relE_{K-12}$ and the lacZ gene were constructed (see Materials and methods). Thus plasmid pKG4001 (+388 to +596) carries a fusion between $relB_{K-12}$ and lacZ, and pKG4002 (+388 to +921) carries a fusion between $relE_{K-12}$ and lacZ. The structure of the relevant parts of these reporter plasmids are shown in FIG. 1. When present in strain MC1000, both plasmids expressed significant amounts of galactosidase fusion proteins, indicating that genes $relB_{K-12}$ and $relE_{K-12}$ are translated (FIG. 1). The $relE_{K-12}$-lacZ fusion (pKG4002) expressed significantly lower amounts of β-galactosidase than the $relB_{K-12}$-lacZ fusion, mainly because pKG4002 encodes an intact $relB_{K-12}$ gene which produces the $RelB_{K-12}$ autorepressor which inhibits transcription from the relB promoter.

Example 3

Demonstration of Translation of the $relB_{P307}$ and $relE_{P307}$ Genes

Figure 2:
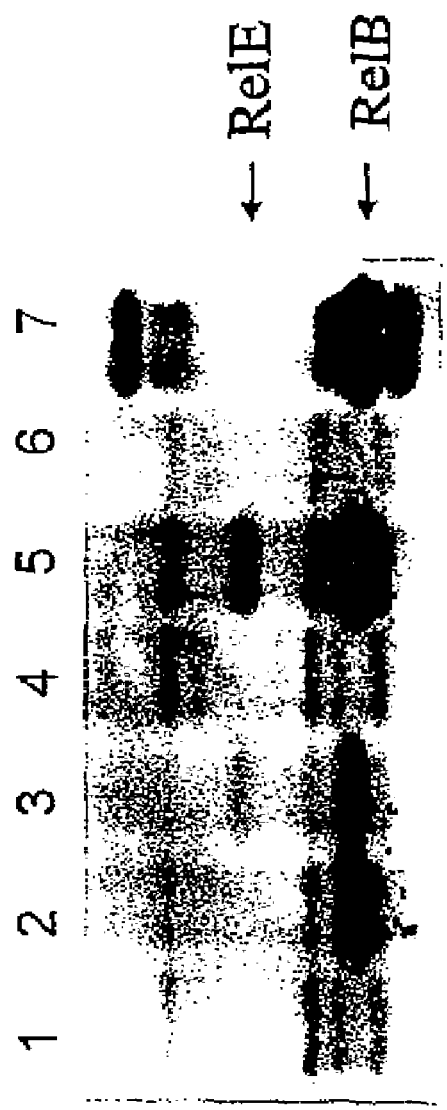

To detect authentic $RelB_{P307}$ and $RelE_{P307}$ proteins, in vitro translation reactions were carried out using high copy number pUC-plasmids carrying genes $relE_{P307}$ (pHA403), $relB_{P307}$ (pHA402) or both genes (pHA100) (for construction of these plasmids, see Materials and Methods and Table 0.1). Proteins produced in the in vitro translation reactions were labelled with $^{35}$S-Methionine and separated by SDS-page. FIG. 2 shows the direct visualization of $RelB_{P307}$ and $RelE_{P307}$, thus providing evidence that the corresponding genes are translated.

Example 4

Demonstrating that $relE_{K-12}$ is a Cytotoxin

Figure 3:
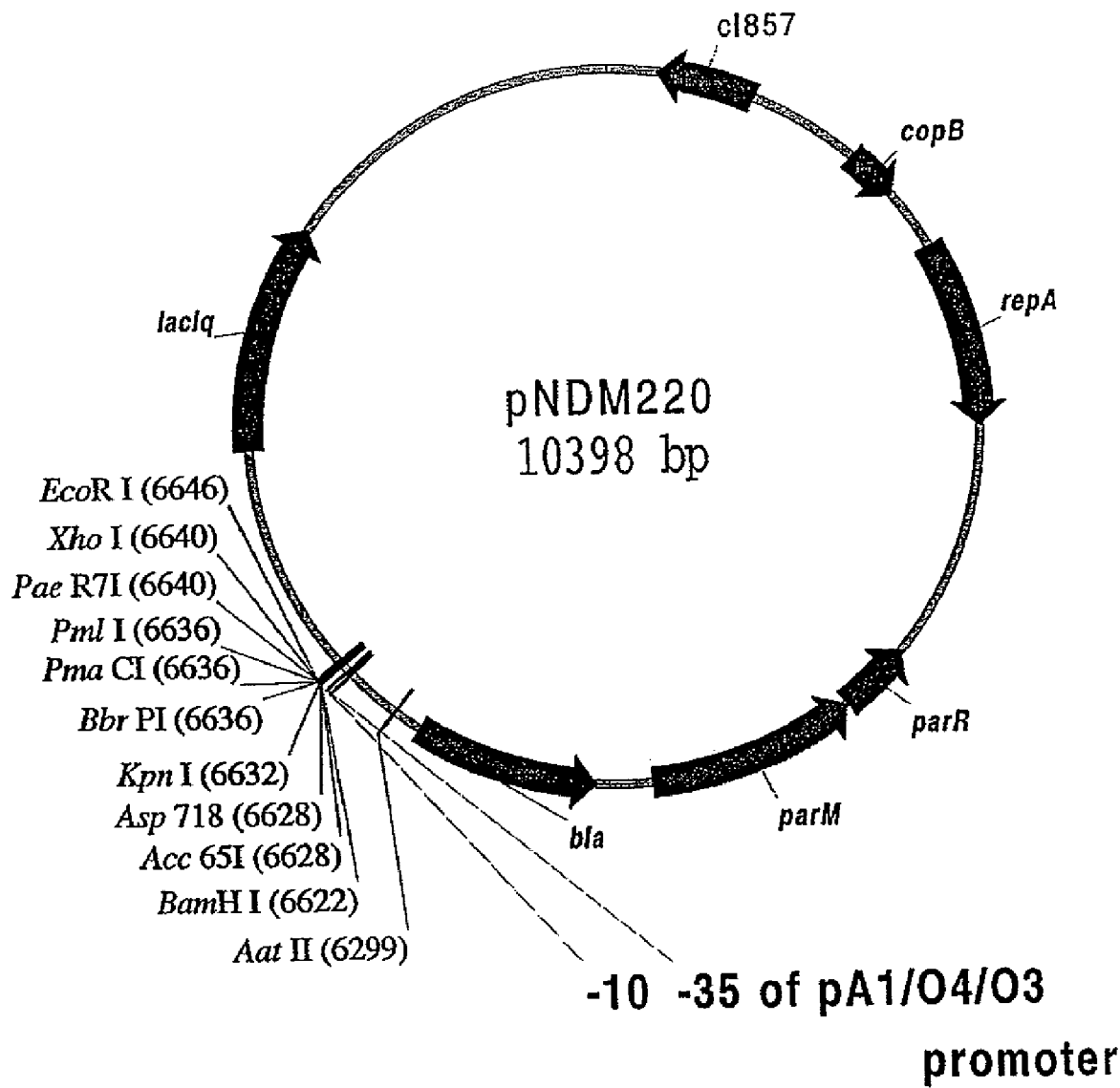

The low copy-number cloning vector pNDM220 contains laClq and the LaCl regulated pA1/O4/O3 promoter (Lanzer and Bujard, 1988) upstream of a multiple cloning site (mcs). The genetic structure of pNDM220 is shown in FIG. 3. Without IPTG added to the growth medium, the pA1/O4/O3 promoter is almost completely turned off. However, with IPTG, strong transcription is induced towards the cloning site. Therefore plasmid pNDM220 is suitable for the conditional expression of genes, in particular toxin-encoding genes.

Figure 4:
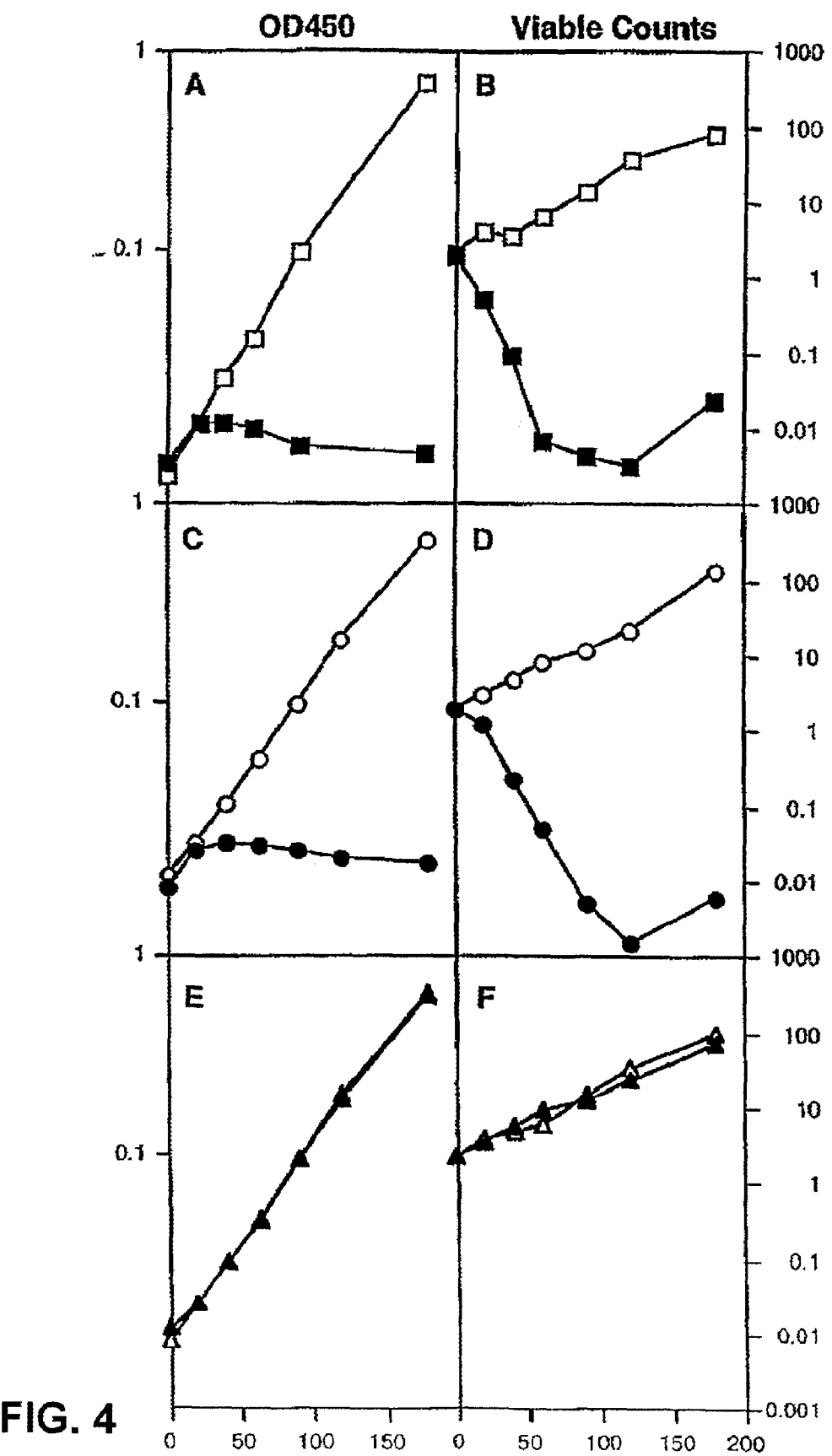

The $relE_{K-12}$ gene of E. coli K-12 (Bech et al., 1985) was PCR amplified and inserted into the mcs of pNDM220, resulting in pMG223 (for the construction of pMG223, see Materials and Methods). Plasmid pMG223 (+733 to +1020) was established in MC1000, which contains a chromosomal copy of the relBE operon. However, it was not possible to transform pMG223 into the JS115 strain, which carries a deletion of the relBE operon (ΔrelB). Therefore, the induction experiments shown in FIG. 4 were accomplished using strain MC1000, which contains the chromosomal copy of $relBE_{K-12}$.

Strain MC1000/pMG223 was grown in LB at 37° C. At time zero, IPTG was added to the growth-medium. After two hours of induction with IPTG, the viable counts decreased c. 600-fold (FIG. 4B). The decline started immediately and continued exponentially for about 2 hours. On plates containing IPTG, viable counts decreased even further (data not shown). The optical density ($OD_{450}$) increased during the first 20 minutes after addition of IPTG and then the culture became stationary (FIG. 4A). Addition of IPTG to growing cells containing the vector-plasmid had no effect (not shown). These results indicate that the relE gene encodes a cell toxin.

Example 5

Demonstrating that $RelB_{K-12}$ is an Antitoxin

Plasmid pMG2202 (+388 to +921) is a pBR322 derivative that contains the relB gene expressed from its own promoter (see Table 1.1). Plasmid pMG2201 (+388 to +597) is a pBR322 derivative that contains the relB promoter and the first part of $relB_{K-12}$. Thus, pMG2201 does not contain an intact relB gene and was included in the analyses as a control plasmid. The strains MC1000/pMG223 (pA1/O4/O3::relE+)-/pMG2202 (relB+) and MC1000/pMG223/pMG2201 (relB−) were subjected to a physiological growth experiment similar to the one described in Example 4. As seen from FIGS. 4E and 4F, the presence of the high copy-number relB-carrying plasmid suppressed relE-dependent cell killing. The antitoxin effect was dependent on an intact relB reading frame, since the control-plasmid (pMG2201) carrying the promoter region and the first part of the relB reading frame did not prevent the relE mediated cell killing (FIG. 4C, 4D).

Example 6

Demonstrating that $relE_{P307}$ Encodes a Very Efficient Cytotoxin

Figure 5:
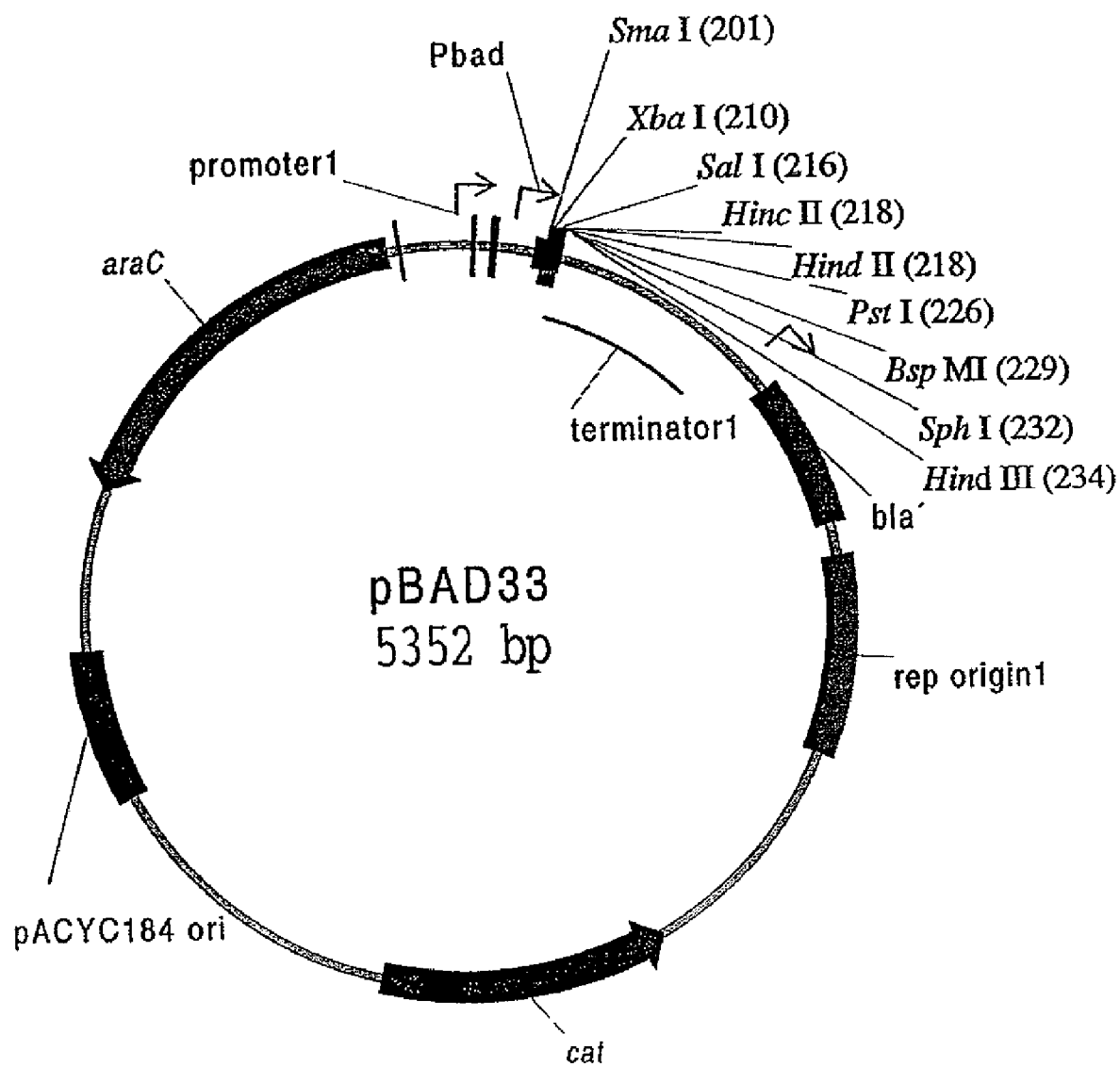

The medium copy number expression vector pBAD33 contains an arabinose inducible promoter (pBAD) with a multiple cloning site (mcs) and the araC gene (Guzman et al., 1995). The genetic structure of pBAD33 is shown in FIG. 5. Without arabinose added to the growth medium, the pBAD promoter is completely turned off. However, with arabinose, strong transcription is induced towards the cloning site. On top of this property, the pBAD promoter is repressible by the addition of glucose to the growth medium. Thus, by the addition of glucose, transcription from pBAD can be rapidly and efficiently turned off.

The glucose repression effect is epistatic to the inducer effect by arabinose. Hence, if cells with a pBAD-carrying plasmid are grown in a medium containing both arabinose and glucose then the promoter is not induced. However, if cell-growth depletes the medium for glucose, then the promoter will be induced. Therefore, plasmid pBAD33 is suitable for the conditional turning on and off of the expression of genes, in particular toxin-encoding genes as described herein.

The relE gene of the E. coli plasmid P307 (Saul et al., 1989) was PCR amplified and inserted into the mcs of pBAD33, resulting in pHA810 (for the construction of plasmid pHA810, see Materials and methods). Thus plasmid pHA810 contains the $relE_{P307}$ gene inserted downstream of the pBAD promoter. Strain MC1000/pHA810 was grown in LB-medium without glucose at 37° C. At time zero, the culture was diluted into medium containing either 0 or 0.2% arabinose. In the arabinose-containing culture, an immediate decline in viable counts was observed (FIG. 6B, closed symbols). The decline continued exponentially throughout the experiment.

After 240 min of induction with arabinose, viable counts had decreased more than five orders of magnitude. Without arabinose, cells containing pHA810 continued to grow exponentially (FIGS. 6A and 6B, open symbols). On plates containing arabinose, none or very few viable cells were detected. These results show that relE$_{P307}$ gene encodes an extremely efficient cell toxin.

Example 7

Demonstrating that RelB$_{P307}$ is an Antitoxin

Plasmid pHA110 (+1 to +1122) is a pBR322 derivative that contains the relB$_{P307}$ gene expressed from its own promoter. The strain MC1000/pHA810/pHA110 (relB$_{P307}$) was subjected to a physiological growth experiment as described in Example 6. It appeared that the presence of the relB$_{P307}$-carrying plasmid pHA110 prevented relE$_{P307}$ dependent inhibition of cell growth (FIG. 6C) and cell killing (FIG. 6D). This observation shows that relB$_{P307}$ codes for an antitoxin that counteracts the cell killing caused by RelE$_{P307}$.

Example 8

Determination of the Frequency of Spontaneous Mutants that are Resistant to the Killing Effect of RelE Strain MC1000/pHA810 was grown exponentially to an OD of 0.5 and serial dilutions of the cell suspension were plated on LA plates containing chloramphenicol (selecting for plasmid pHA810) and with or without 0.02% arabinose (which induces expression of relE present in pAH810). On such plates without arabinose the plating efficiency of strain MC1000/pAH810 was normal, i.e. more than 99% of the viable cells produced a colony. This indicated that the presence of pAH810 in itself had no effect on the viability of the cells. However, with arabinose the plating efficiency was reduced by about 109 fold, thus indicating that expression of RelE is extremely toxic to the cells. The few surviving colonies that appeared eventually were retransformed with the RelE expression plasmid pHA210 which can co-exist with pAH810. However, none of the surviving cells from the first round of selection (i.e. using pHA810) survived induction of RelE (by addition of IPTG) from the second plasmid pAH210.

These results show that resistance against RelE toxicity is a very rare event, as based on this experiment it is less than about $10^{-9}$.

Example 9

Figure 7:
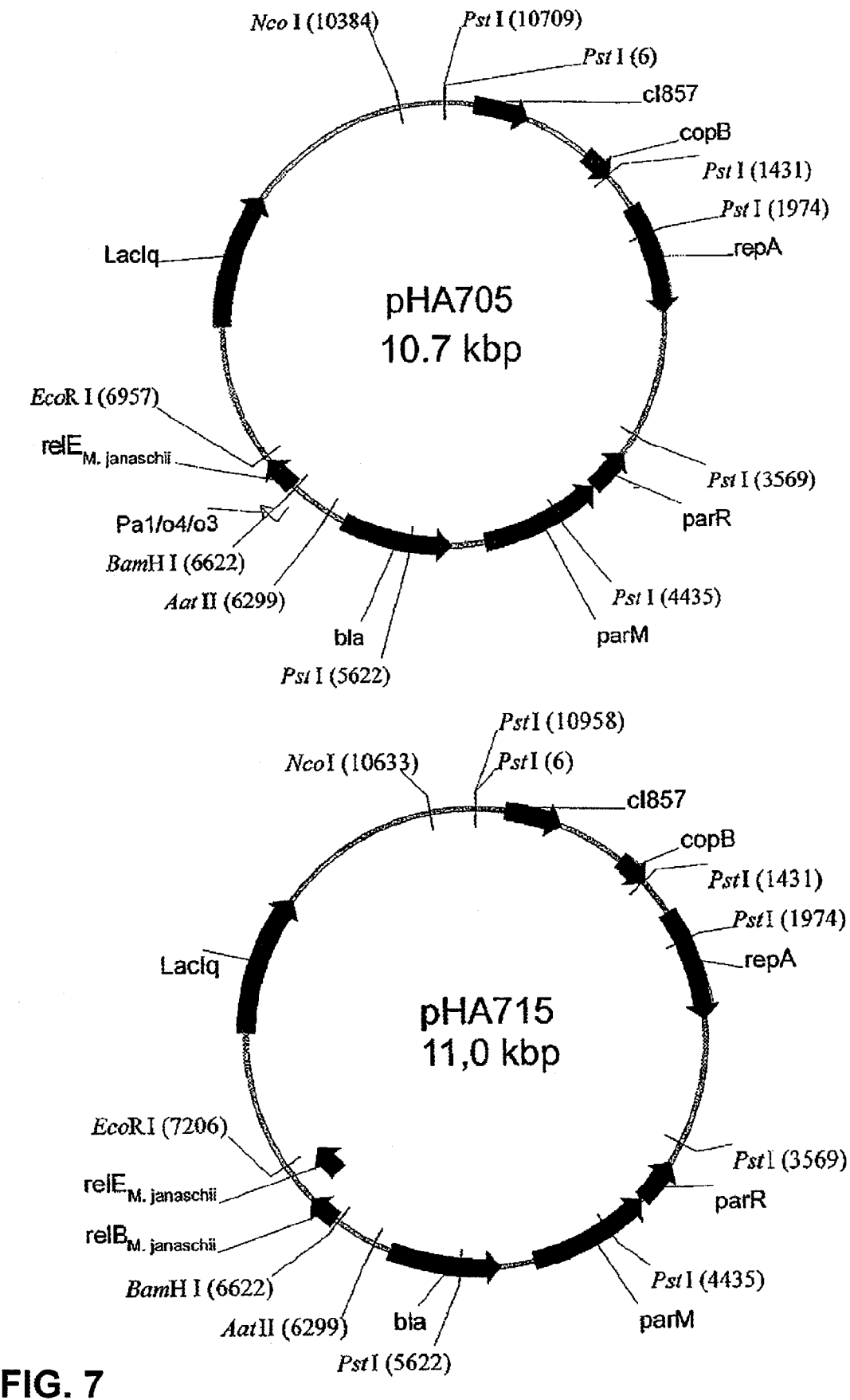
FIG. 7 shows maps of pHA705 and pHA715.

Demonstrating that RelE of the Archeon
Methanococcus jannaschii is Toxic to E. coli The relE gene of M. jannaschii was amplified from genomic DNA using primers MJ-relE/2CWW (5'-CCCCCGAATTCGCATGCGCCATTAGAAT, SEQ ID NO:47) and MJ-relE/1 CW (5'-CCCCCGGATCCGAGCTC-GAGGCTTTGAAAGAATTGGG, SEQ ID NO:48). The resulting DNA fragment was cleaved with BamHI and EcoRI and cloned into plasmid pNDM220 (FIG. 3) thus yielding pHA705 (FIG. 7). Similarly, relB and relE from M. jannaschii were PCR amplified using primers relB-M.jannCW (5'-CCCCGGATCCGTCGACGACAAATAAGGG-GATAACTATG, SEQ ID NO:49) and MJ-relE/2CWW. The resulting DNA fragment was cleaved with BamHI and EcoRI and cloned into pNDM220, thus yielding pHA715 (FIG. 7).

Figure 8:
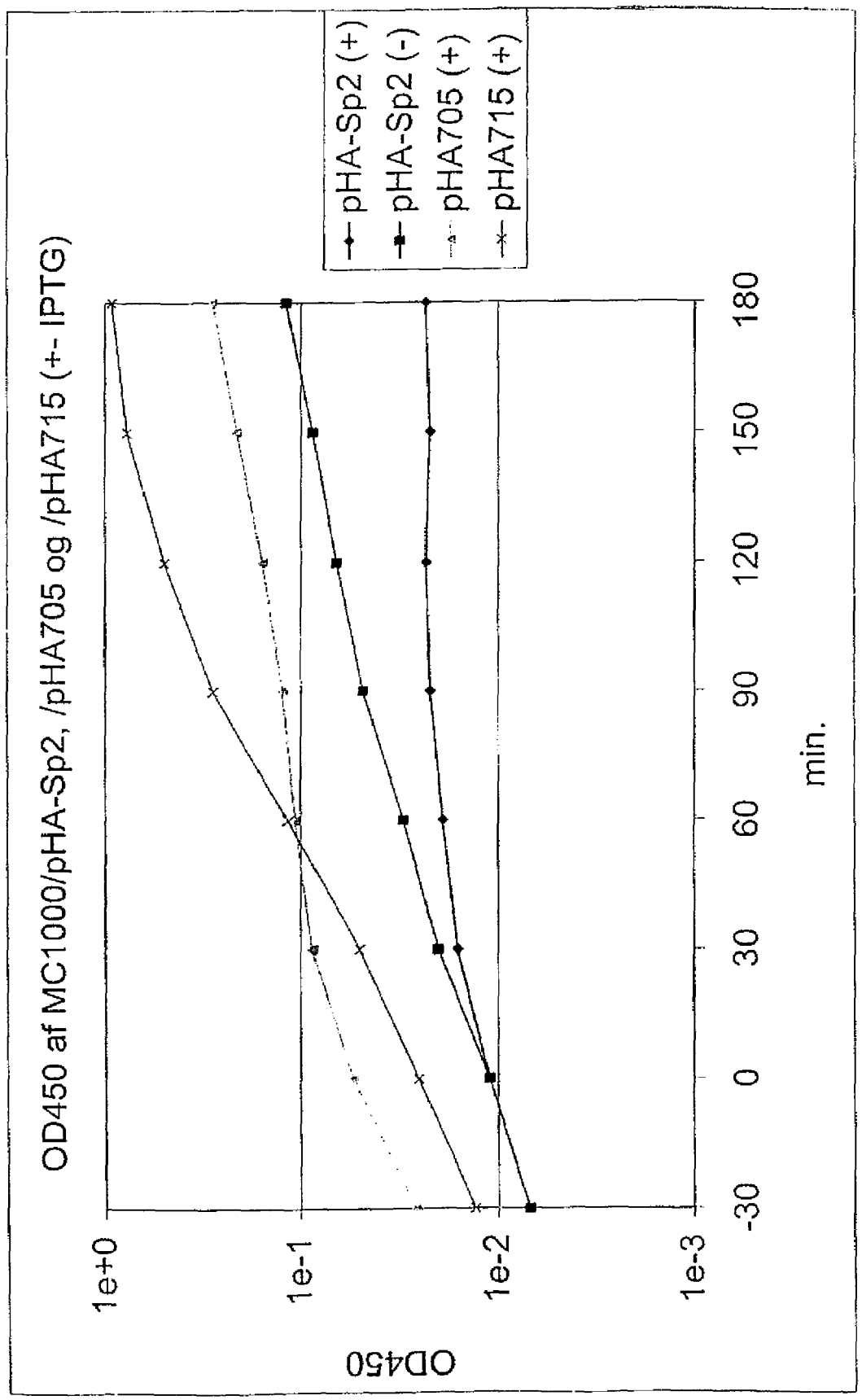
FIG. 8 illustrates $OD_{450}$ of MC1000/pHA-Sp2, MC1000/pHA705 and MC1000/pHA715 (+/–IPTG)
Figure 9:
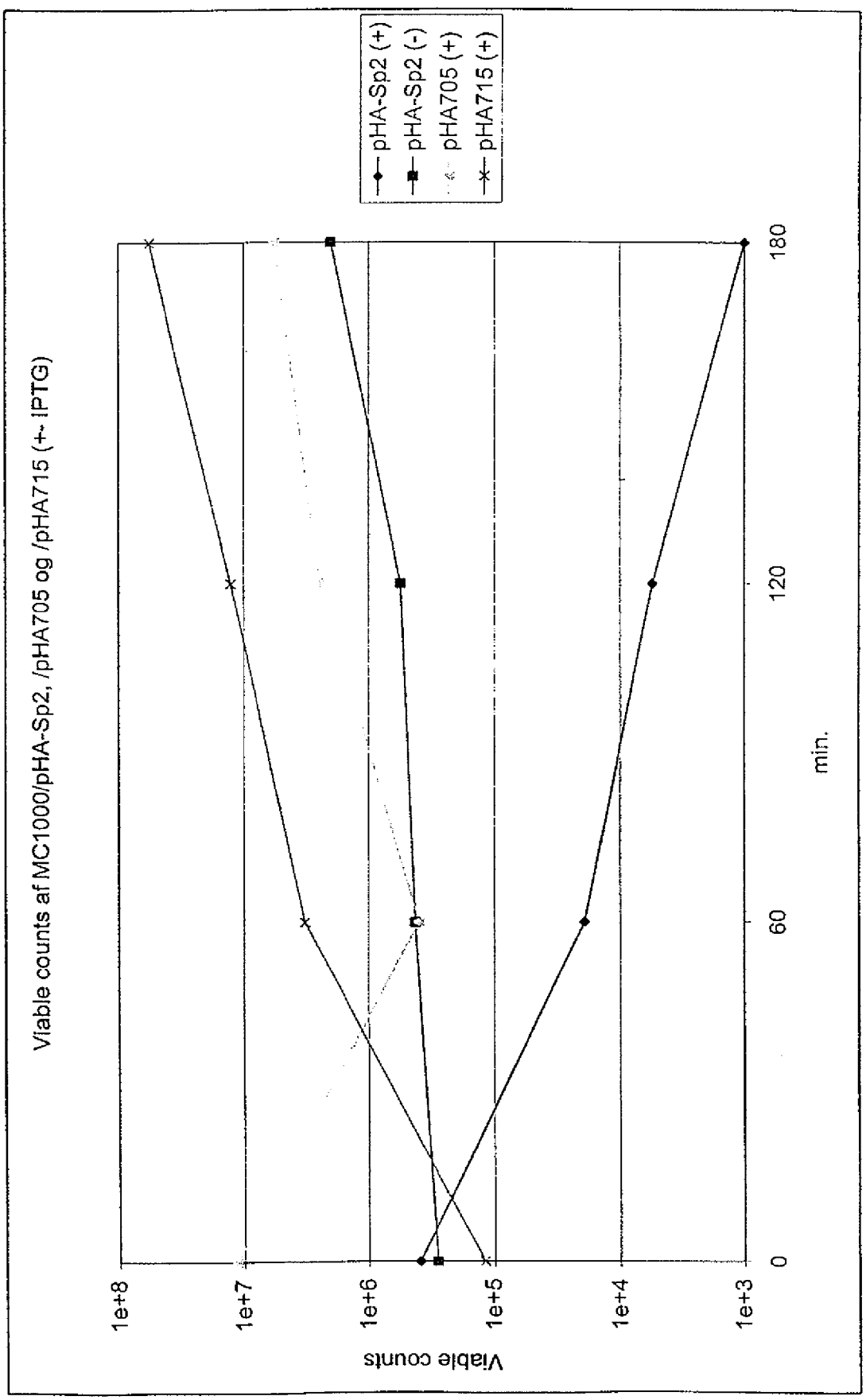
FIG. 9 shows viable counts of MC1000/pHA-Sp2, MC1000/pHA705 and MC1000/pHA715 (+/–IPTG)

Plasmids pHA705 (carrying relE) and pHA715 (carrying relBE) were transformed into E. coli K-12 strain MC1000. Cells were grown exponentially and followed after the addition of IPTG. FIG. 8 shows that the addition af IPTG inhibited the growth of MC1000/pHA705 but not that of MC1000/pHA715, and FIG. 9 shows that viable count was significantly reduced in the case of MC1000/pHA705 but not in that of MC1000/pHA715, thus demonstrating that RelE of M. jannaschii is toxic to E. coli.

Example 10

Figure 11:
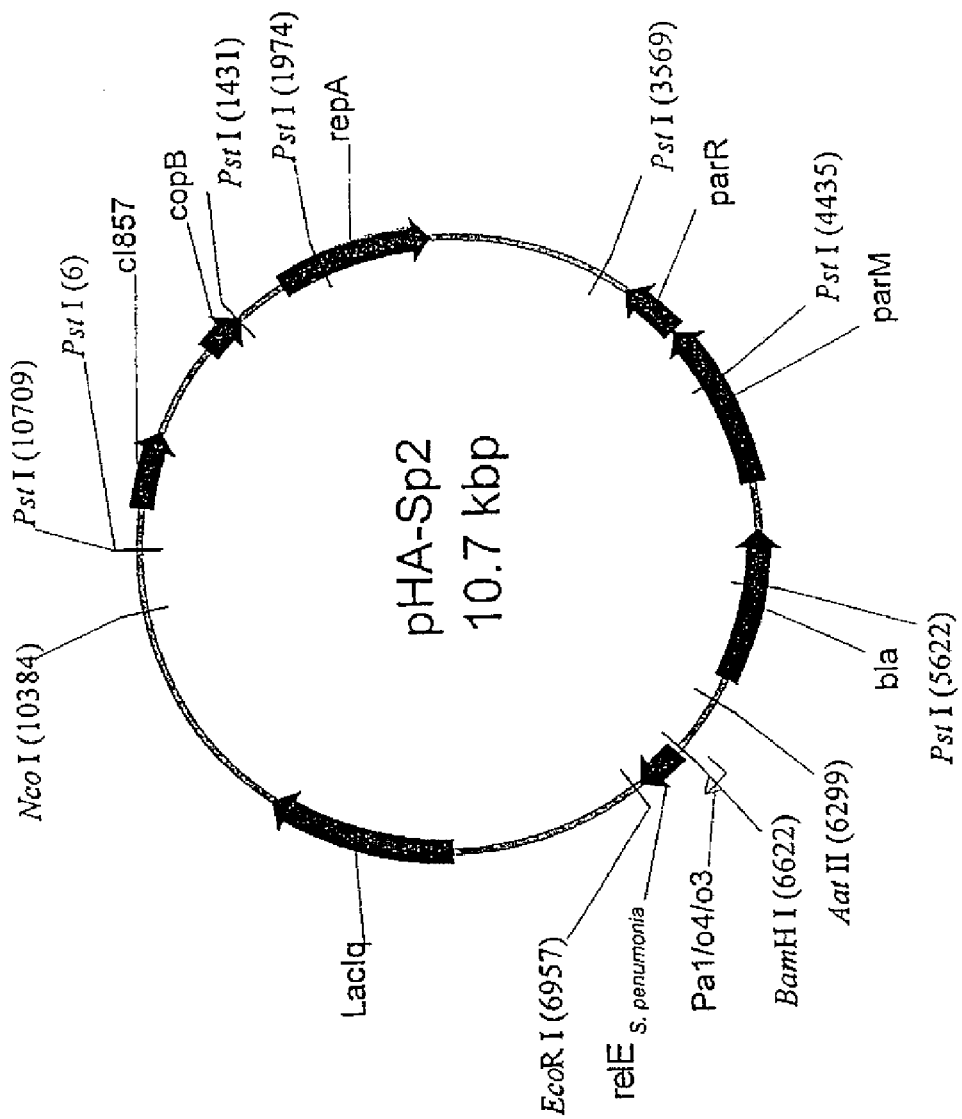
FIG. 11 is a map of pHA-Sp2.

Demonstrating that RelE of the Gram-positive
Bacterium Streptococcus pneumoniae is Toxic to
E. coli Using BLAST database searching, we identified two homologues of the relBE genes of S. pneumoniae. The DNA sequence of the homologue designated relE$_{Sp2}$ is shown in FIG. 10. Gene relE$_{Sp2}$ was PCR amplified from genomic DNA of S. pneumoniae strain RP46 using primers relE-Sp2/cw (5'-CCCCGGATCCGATGCATGATTTAGGCT-TGAAG, SEQ ID NO:50) and relE-Sp2/ccw (5'-CCCCGAATTCGAATGAAAATTTACTTGAAAAAAG, SEQ ID NO:51). The resulting DNA fragment was cleaved with BamHI and EcoRI and cloned into pNDM220 thus yielding plasmid pHA-Sp2 (FIG. 11).

Plasmid pHA-Sp2 (carrying relE$_{Sp2}$) was transformed into E. coli strain MC1000. Cells were grown exponentially and followed after the addition of IPTG. FIG. 8 shows that the addition af IPTG inhibited the growth of MC1000/pHA-Sp2, and FIG. 9 shows that viable counts were dramatically reduced, thus demonstrating that expression of relE$_{Sp2}$ is highly toxic to E. coli.

Example 11

Cloning of the relE Genes of Plasmid P307, M.
jannaschii and E. coli K-12 into the
Broad-host-range Vector pHAG33

Figure 12:
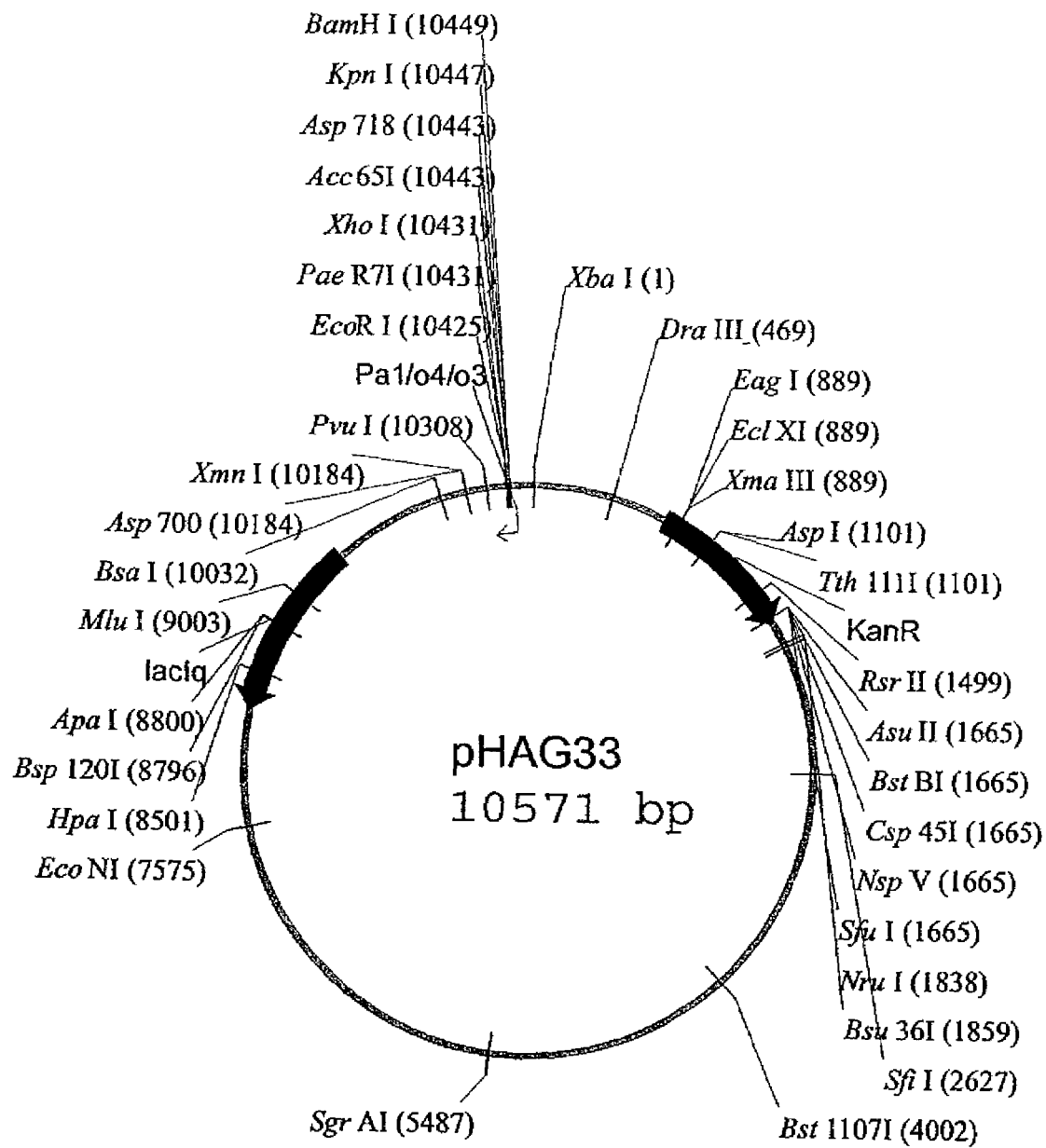
FIG. 12 is a map of pHAG33.
Figure 13:
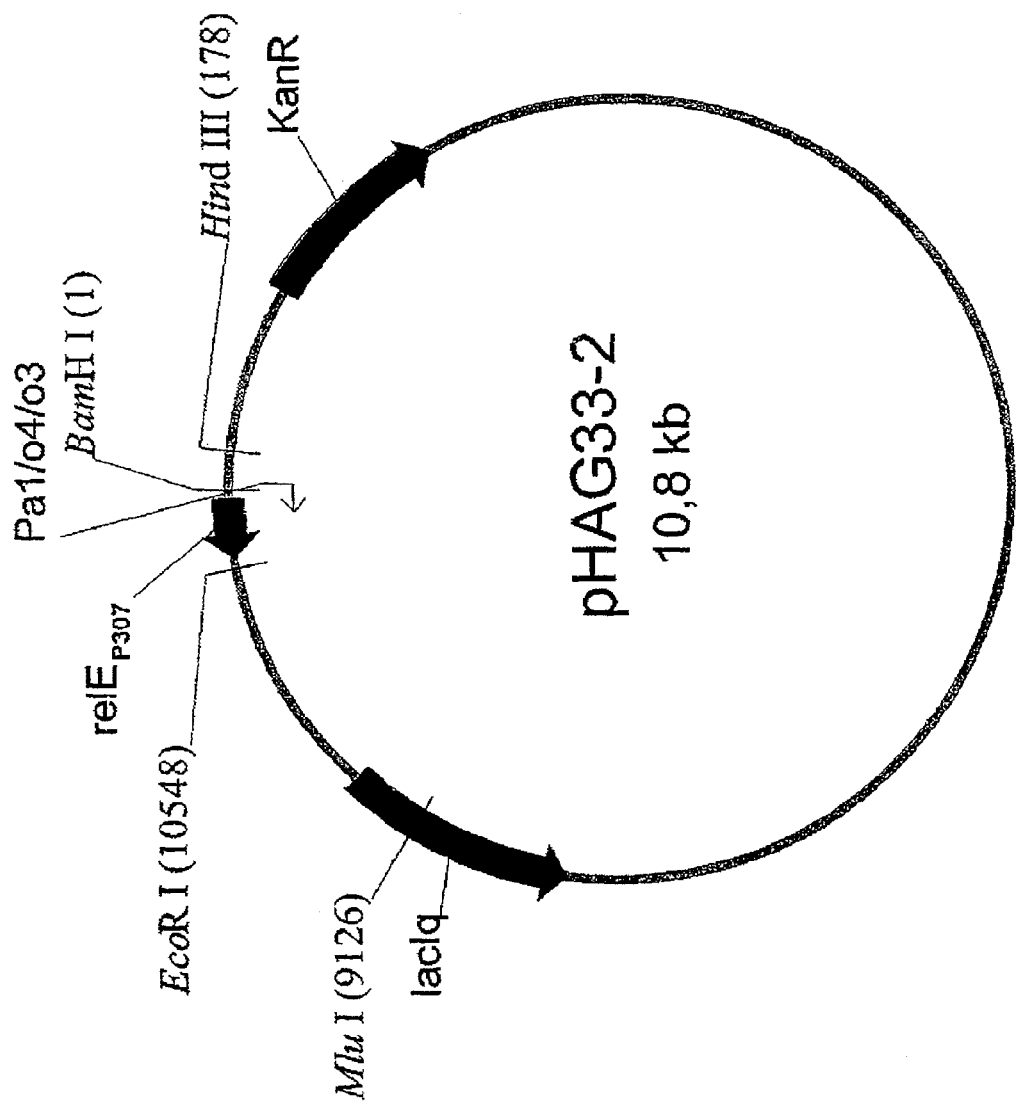
FIG. 13 is a map of pHAG33-2.
Figure 14:
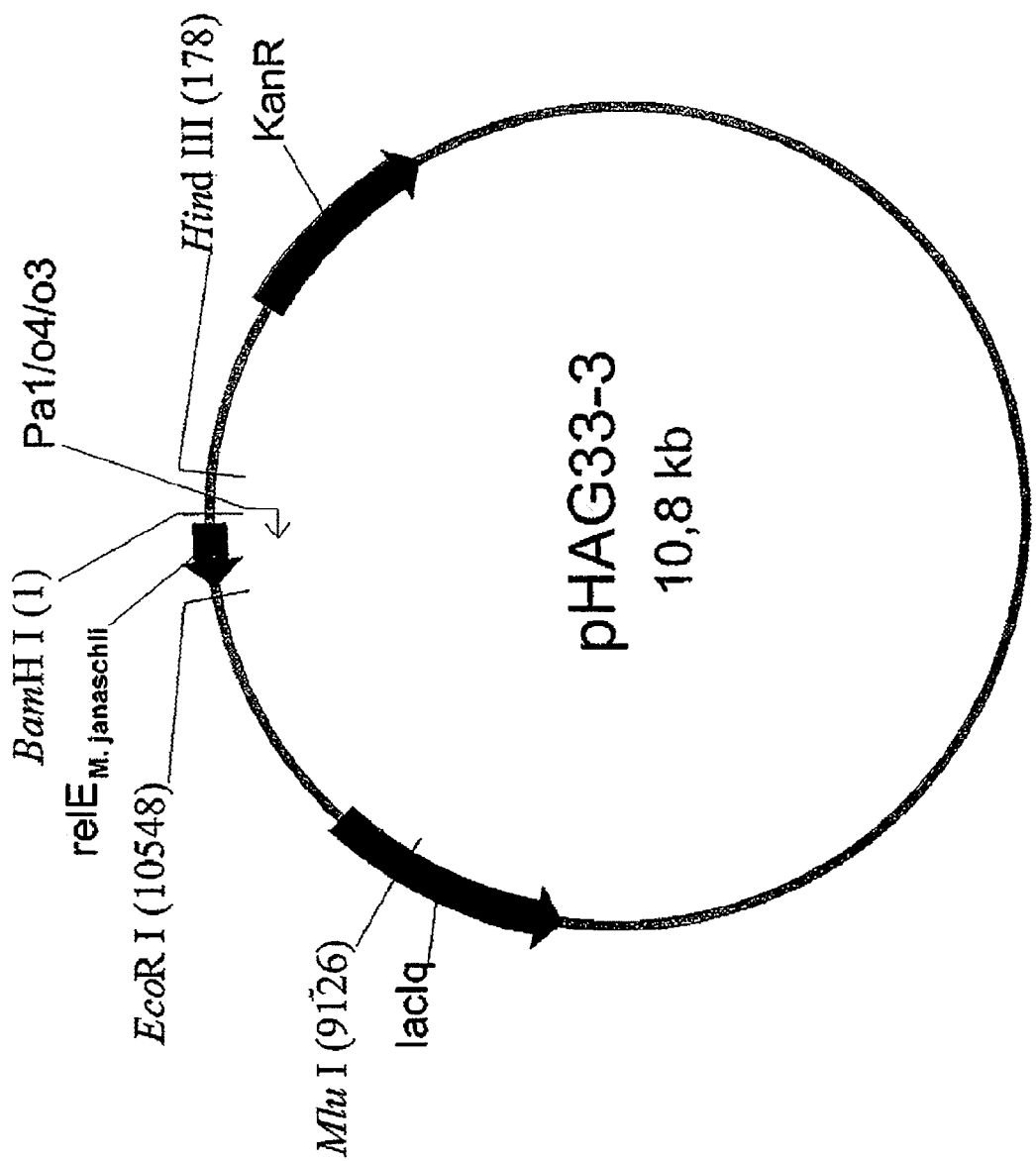
FIG. 14 is a map of pHAG33-3.
Figure 15:
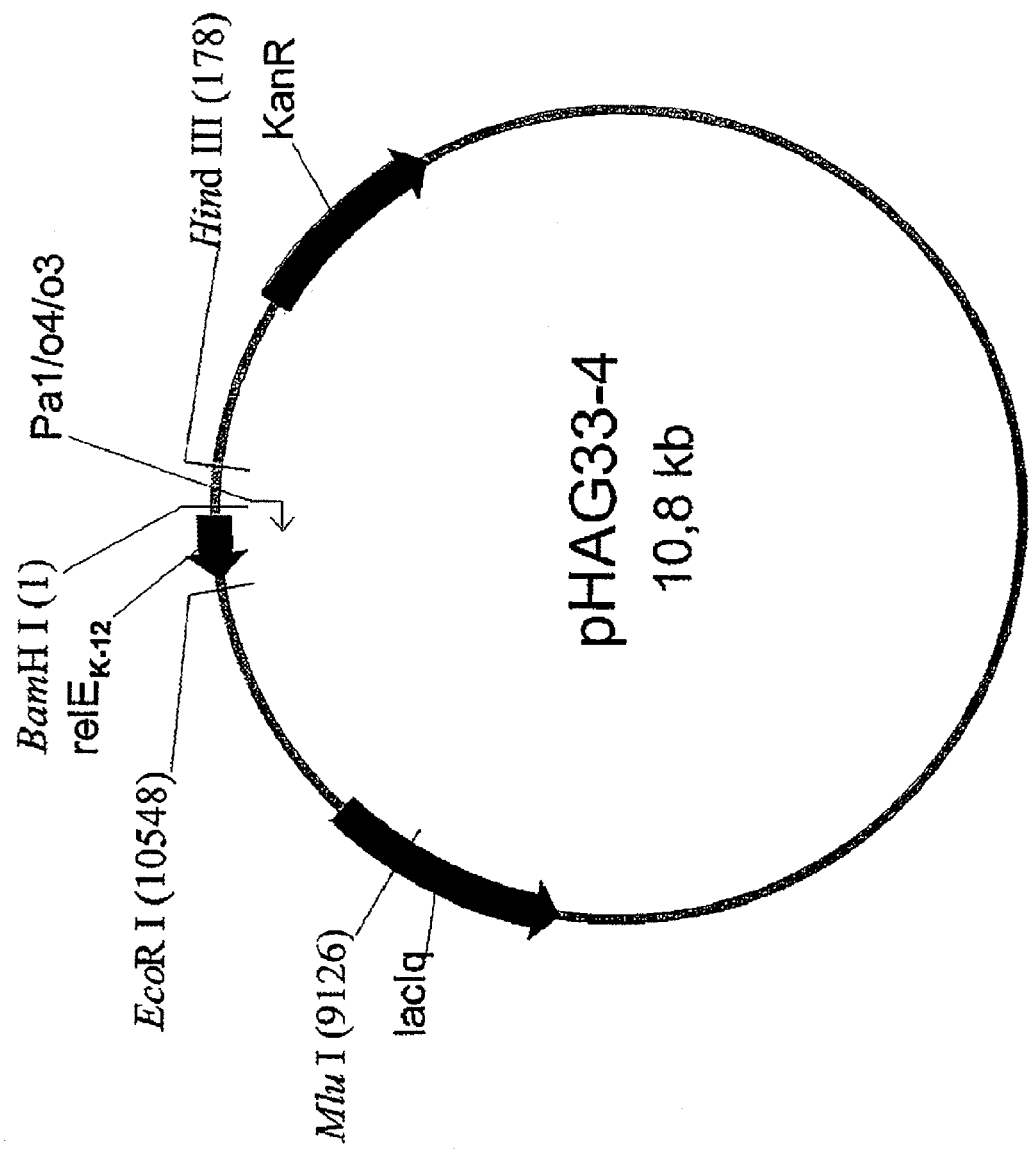
FIG. 15 is a map of pHAG33-4.

The broad-host-range vector pVLT33 is an RSF1010 derivative that can be mobilized by an appropriate conjugation system (de Lorenzo, Eltis, L., Kessler, B. and Timmis, K. N. 1993. Analysis of Pseudomonas gene products using laCl$^q$/Ptrp-lac plasmids and transposons that confer conditional phenotypes. Gene 123, 17-24). It also contains the tac-promoter (ptac) and laCl$^q$. Since ptac is leaky and therefore unsuitable for the regulated expression of toxins, the promoter was replaced by the pA1/O4-O3 promoter of pNDM220. The resulting plasmid, pHAG33, is shown in FIG. 12. The relE genes of pHA210 (relE$_{P307}$), pHA705 (relE$_{Mj}$) and pMG223 (relE$_{K12}$) were cloned into pHA33, resulting in plasmids pHA33-2 (FIG. 13), pHA33-3 (FIG. 14), and pHA33-4 (FIG. 15), respectively.

Example 12

Demonstrating that RelEs of E. coli K-12, P307 and
M. jannaschii are Toxic to Pseudomonas putida Plasmids pHA33-2 (relE$_{P307}$), pHA33-3 (relE$_{Mj}$) and pHA33-4 (relE$_{K12}$) were transformed into the E. coli K-12 strain S17-1. This strain contains the conjugation system of RP4 and is thus able to mobilize pHA33-derived plasmids as described above (Simon et al., 1986). After conjugation on solid medium to *P. putida* strain KT2440 according to standard procedure, strains KT2440/pHA33-2, KT2440/pHA33-3 and KT2440/pHA33-4 were established.

Figure 16:
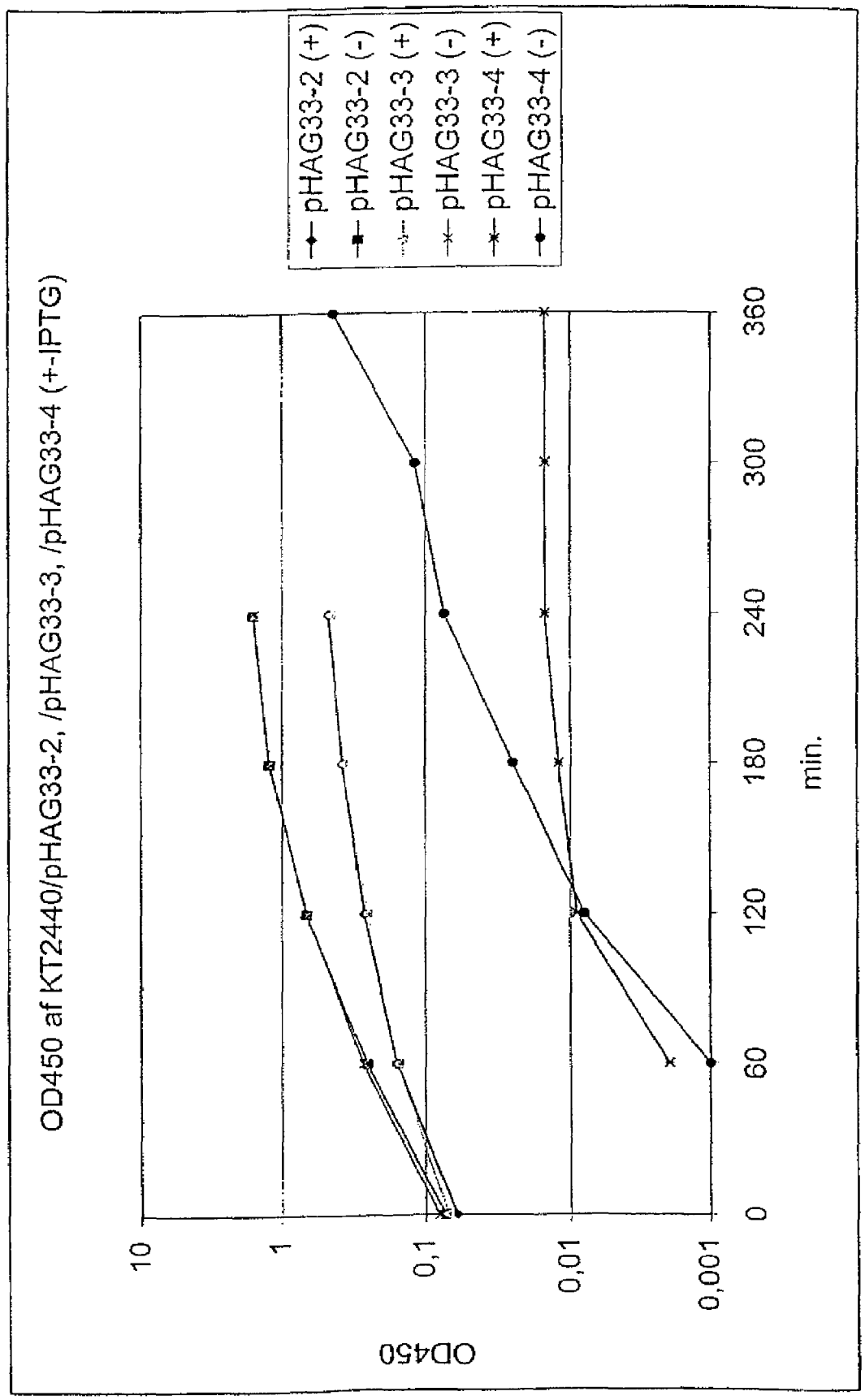
FIG. 16 illustrates $OD_{450}$ of KT2440/pHAG33-2, KT2440/pHAG33-3 and KT2440/pHAG33-4 (+/–IPTG)
Figure 17:
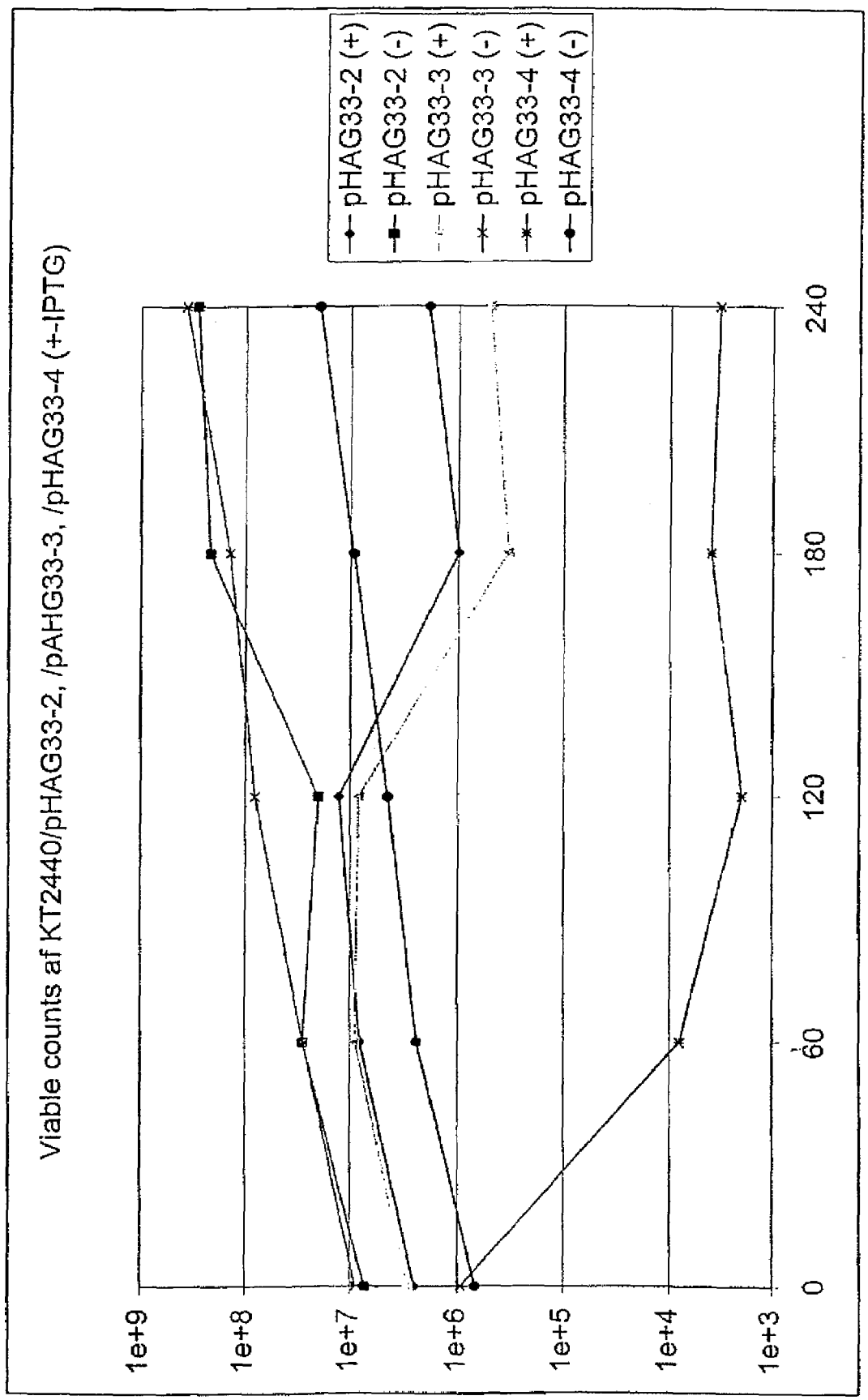
FIG. 17 shows viable counts of KT2440/pHAG33-2, KT2440/pHAG33-3 and KT2440/pHAG33-4 (+/–IPTG)

The strains were grown exponentially in LB containing 30 µg/ml ampicillin and 50 µg/ml kanamycin and followed after the addition of 2 mM IPTG. As seen from FIG. 16, the increment in cell-growth as measured by $OD_{450}$ was reduced by IPTG in all three cases. Furthermore, measurements of viable counts (FIG. 17) showed cell-killing in all three cases, most severe in the case of $relE_{K12}$ (pHA33-4(+) in FIG. 17). Thus, RelE proteins of P307 and *M. jannaschii* are toxic to *P. putida* and RelE of *E. coli* K-12 is extremely toxic to *P. putida*.

Example 13

Demonstrating Biological Containment by the Depletion of a Carbon Source

Figure 18:
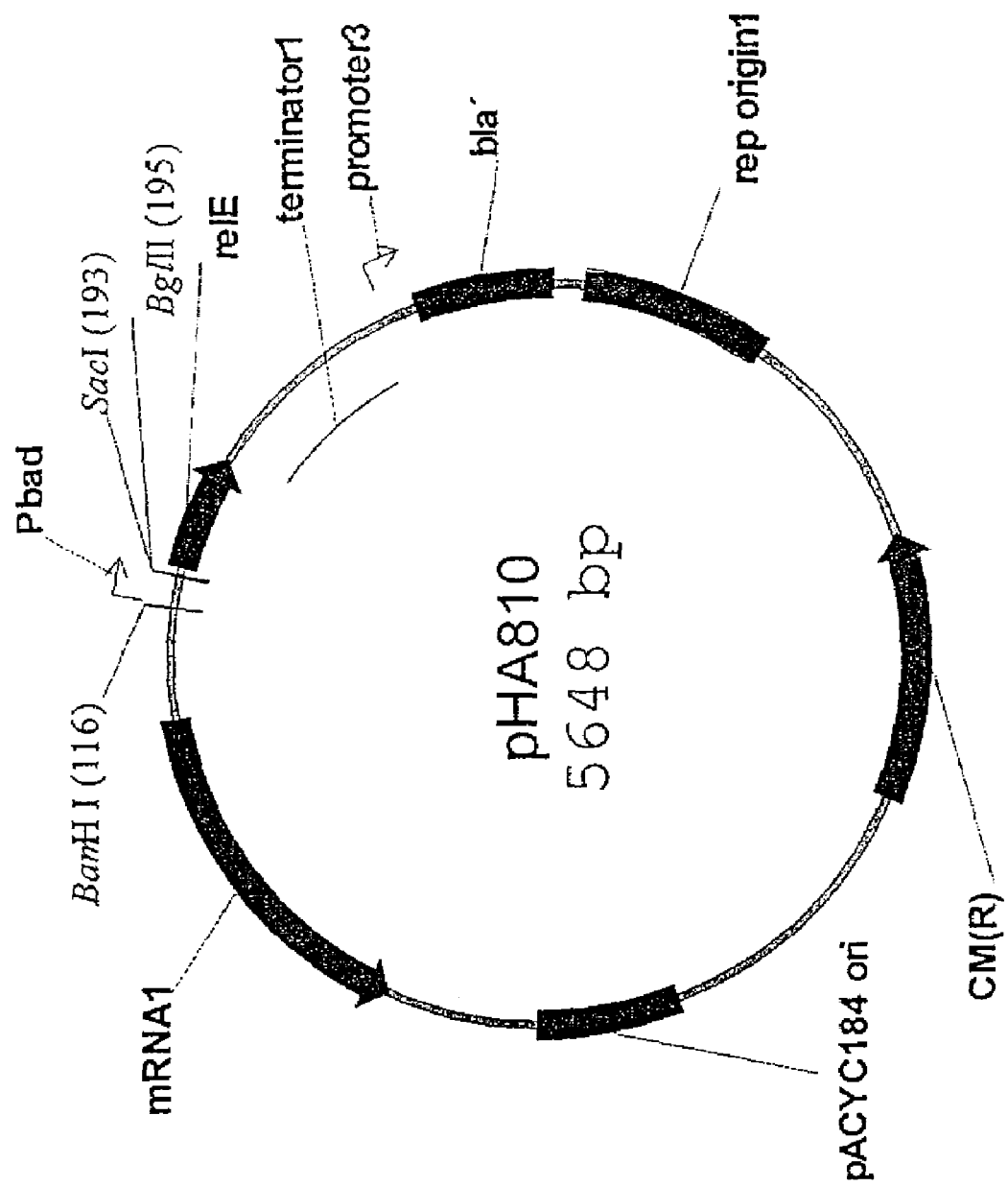
FIG. 18 is a map of pHA810.

Plasmid pHA810 (FIG. 18) was constructed by inserting the relE gene of P307 into the expression vector pBAD33 (FIG. 5). The promoter (designated $p_{BAD}$) upstream of $relE_{P307}$) in pHA810 is repressed by glucose and induced by arabinose. The repression by glucose overrides induction by arabinose such that the simultaneous presence of glucose and arabinose in the growth medium results in repression of the promoter.

Figure 19:
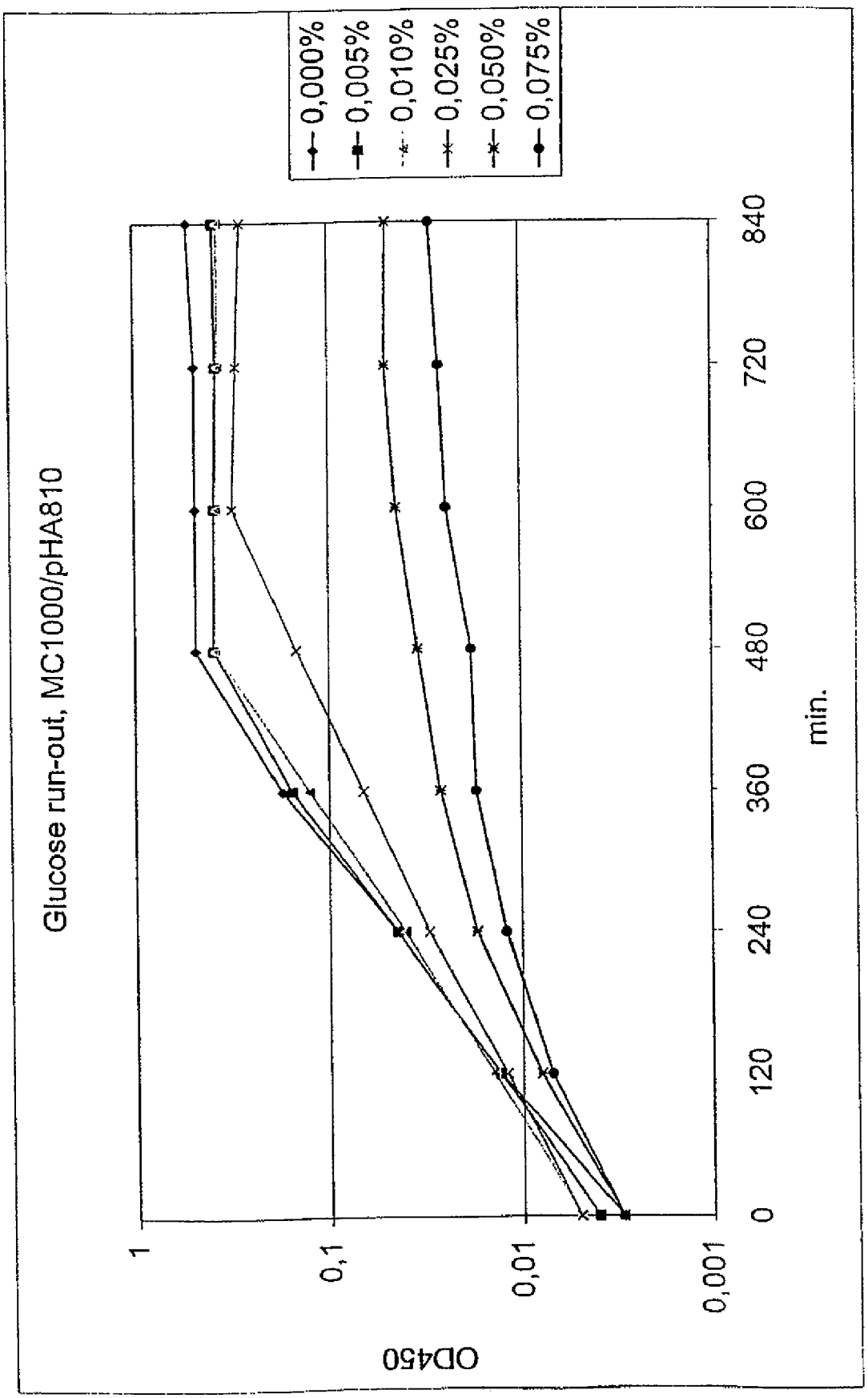
FIG. 19 illustrates Glucose run-out, $OD_{450}$ of MC1000/pHA810.
Figure 20:
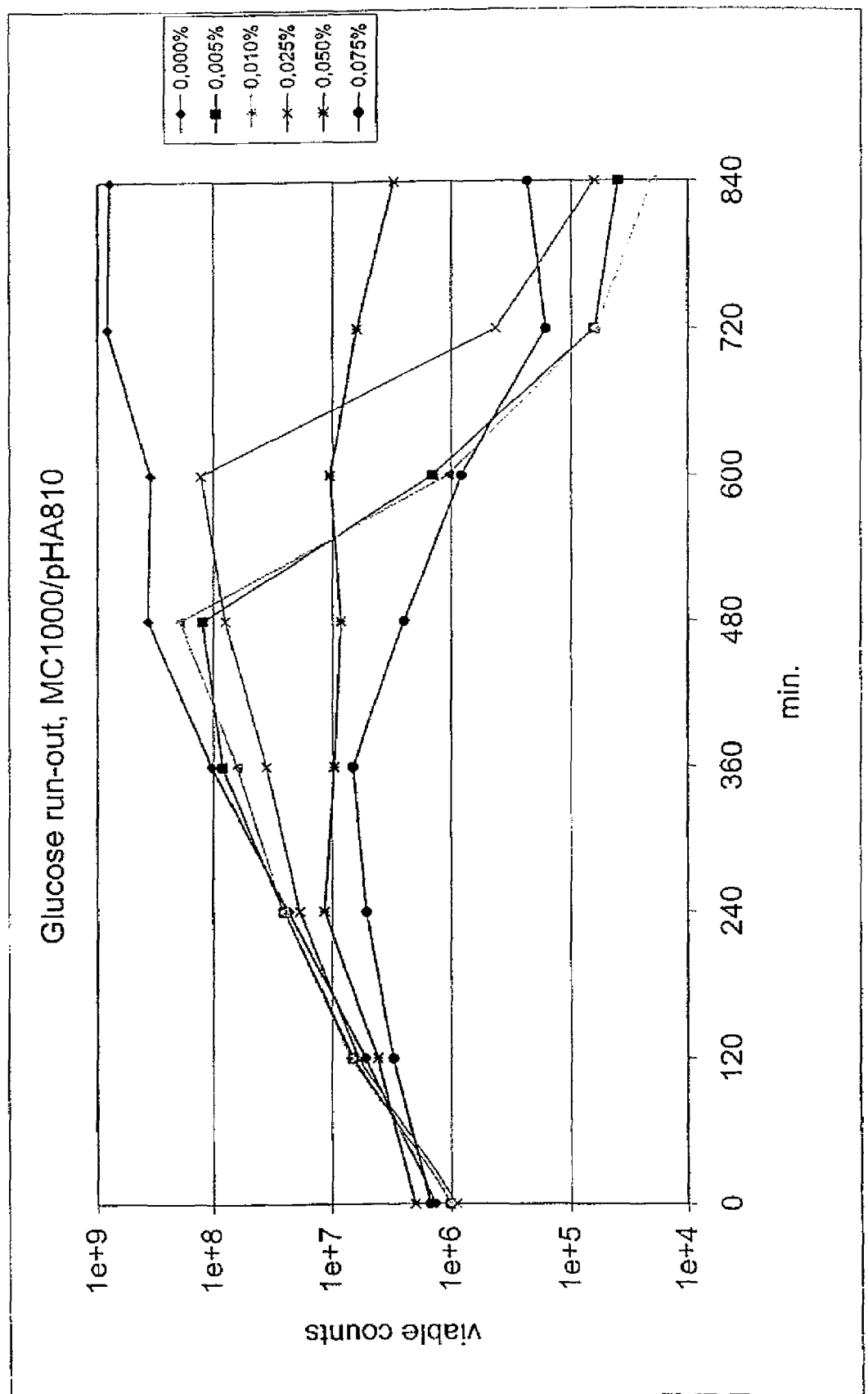
FIG. 20 illustrates Glucose run-out, viable counts of MC1000/pHA810.

To simulate a realistic scenario in which the carbon source was depleted, we grew MC1000/pHA810 in ABT minimal salts medium at 35° C. in the presence of a limiting amount of glucose (0.025% w/v) (represses $p_{BAD}$) and varying the concentration of arabinose (induces $p_{BAD}$). Optical density (FIG. 19) and viable counts (FIG. 20) typical for such an experiment were obtained. As seen in FIG. 19, the rate of increase in $OD_{450}$ is severely reduced by the highest amounts of arabinose (0.050% and 0.075%). This was expected, since arabinose induces pBAD and the limited amount of glucose (0.025%) cannot fully suppress pBAD at high concentrations of arabinose. The glucose added (0.025%) was depleted by cell growth at an $OD_{450}$=approx. 0.1. At this $OD_{450}$, a dramatic cell killing was seen in the case of 0.005%, 0.010%, and 0.025% of arabinose (FIG. 20). This result shows, that depletion of the carbon source (glucose) leads to massive cell killing, and thus to biological containment of the plasmid that carries $relE_{P307}$.

Example 14

Demonstrating that RelE of *E. coli* K-12 and *M. jannaschii* are Toxic to Human Cells The cell line 293 is a permanent line of primary human embryonal kidney cells transformed by human adenovirus type 5 (Ad 5) DNA (ATCC CRL-1573). The cells are particularly sensitive to human adenovirus, are highly permissive for adenovirus DNA, and contain and express the transforming genes af AD 5 (Graham, F. L., Smiley, J., Russell, W. C., and Nairn, R. 1977. Characteristics of a human cell line transformed by DNA from human adenovirus type 5. J. Gen. Virol. 36, 59-74).

Plasmid pcDNA3.1 (+) (Invitrogen) carries the constitutive promoter $P_{CMV}$ from cytomegalovirus upstream of a multiple cloning site (mcs). Genes relE of *E. coli* K-12 and *M. jannaschii* were inserted in the mcs, resulting in plasmids p5.4 and p5.3, respectively.

Plasmids pcDNA3.1(+)(control), p5.4 and p5.3 were transfected into cell line 293 by selection in medium containing G418 (geneticin), which selects for cells expressing the neomycin gene present on the plasmids. After 12 days, the cell density was measured by inspection. In the case of p5.4 ($relE_{K-12}$), between 0 and 5% of the cells had survived (as compared to the control). In the case of p5.3 ($relE_{Mj}$), between 5 and 10% of the cells had survived. These results indicate that the bacterial $relE_{K-12}$ and the archival $relE_{Mj}$ toxins both are lethal to human cells.

Example 15

Demonstrating that $RelE_{K-12}$, $RelE_{P307}$, and $RelE_{Mj}$ Inhibit Translation in vitro DNA fragments comprising genes $relE_{K-12}$, $relE_{P307}$ and $relE_{Mj}$ were PCR amplified such that a T7 RNA polymerase promoter was placed upstream of the corresponding genes (according to Thisted et al., 1994.

The following primers were used: $relE_{K-12}$ (P1: 5'-<u>TGTAATACGACTCACTATAG</u>ATAAGGAGTTTTAT AAATGGCGTATTTTCTGGATTTTG, SEQ ID NO:52) and P2 (CACCTTCGGTGCGAAACAG, SEQ ID NO:53); $relE_{P}307$ (P3; 5'-<u>TGTAATACGACTCACTATAG</u>ATAA GGAGTTTTATAAATGAGGTATCAGGTAAAATTCA (SEQ ID NO:54) and P4: 5'-CTTTCCATCGGCGAAT-TATC, SEQ ID NO:55); $relE_{Mj}$ (P5: 5'-<u>TGTAATACGACTCACTATAG</u>ATAAGGAGTTTTATAAA TGAAGTTTAACGTTGAGATAC SEQ ID NO:56) and P6: (5'-ATCATGGTATCAGCCGAATC, SEQ ID NO:57). T7 RNA polymerase sequences are underlined, and the strong Shine-Dalgarno (SD) sequence from the parA system of plasmid R1 is shown in italics.

Using in vitro transcription with T7 RNA polymerase according to standard procedures, mRNAs encoding $relE_{K-12}$, $relE_{P307}$, and $relE_{Mj}$ were produced and subsequently purified from a denaturing polyacrylamide gel. To facilitate the quantification of the mRNAs they were labelled with tritium (alfa-$^3$H-CTP) during their synthesis. The relE-encoding mRNAs (1.5 pmol) were used as templates in in vitro translation reactions employing an S30 extract (obtained from Promega) containing 150 µM of each amino acid except Methionine which was 1 µM.

Figure 21:
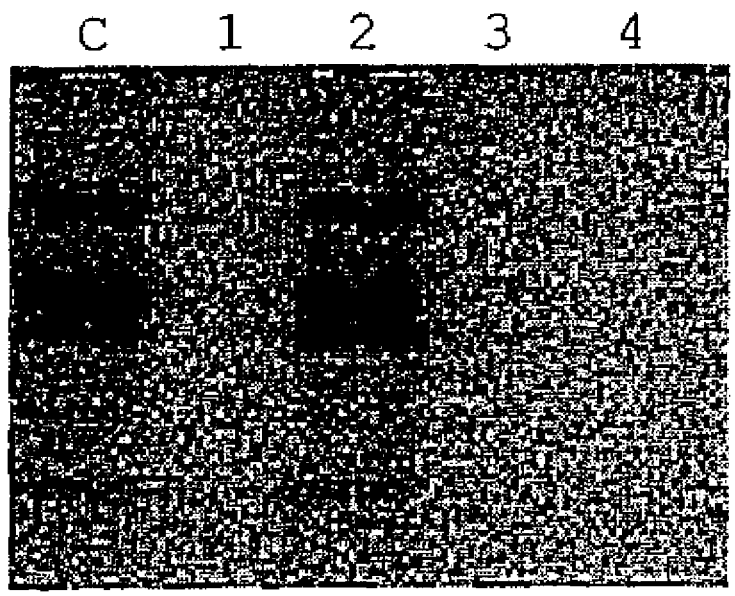
FIG. 21 illustrates that $RelE_{K12}$, $RelE_{P307}$ and $RelE_{Mj}$ inhibit translation in vitro

FIG. 21 shows SDS-PAGE (tricine-gel) analysis of such an experiment. The in vitro translation reactions were initiated with unlabelled Methionine in order to produce RelE toxin in the reaction. Ten minutes after the addition of the unlabelled Methionine, radioactive 35-S-Methionine (5 pmol in a 15 µl volume) was added and the reaction continued for an additional 20 minutes. C in FIG. 21 denotes a control lane without exogenous mRNA added. The protein bands seen in this lane originate from translation of mRNAs present in the S30 extract. In lane 1, the in vitro translation reaction contained an mRNA encoding the relE gene of *E. coli* K-12. As seen, the translation reaction was severely inhibited. In lane 2, a mRNA encoding a mutated relE (denoted relEmE and described in Gotfredsen et al, 1998) gene was added. As seen, the presence of this mRNA did not inhibit the reaction. This result shows that the RelE protein produced during the initial incubation-period without 35-S-Met added inhibits the in vitro translation reaction (i.e. compare lanes 1 & 2). Furthermore, this lack of inhibition is correlated with loss of cell killing activity in vivo (since the mutated relE gene, relEmE, used in lane 2 is not toxic to *E. coli* cells), thus indicating that inhibition of translation is the actual cause of cell death in vivo. In lanes 3 and 4, mRNAs encoding relE of plasmid P307 and the archaeon *M. jannaschii* were added. As seen, the presence of these mRNAs inhibited the in vitro translation reactions as well. These results indicate that the RelE toxins from *E. coli* K-12, *M. jannaschii* and plasmid P307 all act by inhibition of translation.

Example 16

Demonstrating that RelE$_{K-12}$ is Toxic to Yeast Cells

1. Yeast Strain

In these experiments the yeast strain *Saccharomyces cerevisiae* 281288DIV-36 (MATa his 4-5; LEU2 THR4 ura3-52 trp1 CYH2 KAR1) was used.

2. PCR Amplification of RelE Coding Region

The RelE coding region was PCR amplified from the plasmid pMG223 using two oligonucleotide primers. The primer S-RelE was 24 nucleotides long (5'-TAGGTACCATGGCGTATTTTCTGG-3', SEQ ID NO:58). It contains KpnI and NcoI endonuclease restriction sites at the 5' end with an 8 nucleotide overhang. Primer AS-RelE was 23 nucleotides long (5'-GAGACCCCACACTACCATCGGCG-3', SEQ ID NO:59) and hybridises 400 nucleotides downstream the RelE termination codon and 392 nucleotides downstream the EcoRI site in plasmid vector pMG223. PCR amplifications were performed using Vent© Polymerase (New England Biolabs), 200 µM of each dNTP. PCR reaction buffer (10 mM KCl; 10 mM (NH$_4$)$_2$SO$_4$; 20 mM Tris-HCl (pH 8.8); 2 mM MgSO$_4$; 0.1% Triton X-100) with 0.2 µM of each of the primers. After 5 min denaturation (95° C.) PCR was performed with 20 cycles, each cycle consisting of 1 min denaturation (92° C.), 1 min primer annealing (50° C.) and 1 min primer extension (72° C.). Successful PCR products of 706 bp DNA fragments were identified and purified from a 1% agarose gel after a run of 1 hour at 40 mA. The PCR product was digested with the two restriction enzymes KpnI and EcoRI and the fragment of 304 bp containing the RelE open reading frame was isolated after electrophoresis on a 1.2% agarose gel, and purified using a gel extraction kit (Pharmacia).

3. Cloning of the Amplified relE Gene

The isolated DNA fragment of the relE gene flanked with KpnI and EcoRI sites was ligated into the pYES2 expression vector (Invitrogen) previously digested with KpnI and EcoRI using standard procedures (Sambrook). After ligation, *E. coli* Top10 (Invitrogen) was transformed with the ligation mixture using electroporation using the *E. coli* gene pulser (BioRad). After phenotypic expression for 2 hours in SOC medium the culture was spread onto selective LB medium (Sambrook) containing 50 µg of ampicillin per ml. Transformed colonies were identified using PCR amplification and a positive clone designated pPK727 was further tested by restriction enzyme analysis. The functionality of the PCR amplified RelE gene was tested in *E. coli* by cloning the NcoI-EcoRI fragment from pPK727 into the *E. coli* expression vector pUHE24. Induction with IPTG led to cell killing in *E. coli*.

4. Yeast Transformation

*S. cerevisiae* was grown overnight (ON) in YDP medium (1% yeast extract; 2% Bacto peptone; 2% glucose). For a single transformation, cells from 1 ml ON culture were spun down (5,000 rpm for 30 sec using an Eppendorf minicentrifuge) and washed twice in sterile water. Cells were resuspended in 200 µl lithium acetate buffer (10 mM Tris-HCl pH 7.6 with 100 mM LiOAc, 1 mM EDTA). After incubation for 15 min. at 25° C. with agitation two transformations were made adding 20 µl carrier DNA (10 mg/ml salmon sperm DNA, sonicated and heat denatured) and 100 ng of the plasmids pPK727 and pYES2 (vector control), respectively. A volume of 1.2 ml 40% PEG 4,000 in 0.1 M lithium acetate buffer was added to each transformation mixture. The transformation mixtures were incubated in a 25° C. incubator for 30 min before transferring to a 42° C. water bath for 15 min. Cells were spun down (5,000 rpm for 30 sec.) and washed once with sterile water before plating on Uracil drop-out medium (1% Bernstein acid; 0.1% NaOH; 2% glucose; 0.67% Bacto yeast nitrogen base; 0.1% amino acids (without uracil); 2% agar).

After three days growth at 30° C. single colonies were picked and streaked onto plates with Uracil drop-out medium. After two days at 30° C. cells were transferred to induction medium (Uracil drop-out medium with 2% galactose as the sole carbon source) by replica-plating.

Single colonies of *S. cerevisiae* containing pPK727 and pYES2 were transferred to liquid Uracil drop-out medium (1% Bernstein acid; 0.1% NaOH; 2% glucose; 0.67% Bacto-yeast nitrogen base; 0.1% amino acids (without uracil)) and incubated ON. To compensate for difference in cell density, a volume of 50 µl upper OD$_{540}$ (optical density at 540 nm) was used to inoculate 50 ml of liquid Uracil drop-out medium with either glucose or galactose as sole carbon source, respectively. The four flasks with *S. cerevisiae* (pPK727) and *S. cerevisiae* (pYES2) in Uracil drop-out medium with or without galactose were incubated at 30° C. with moderate shaking (200 rpm). To monitor growth, samples were taken at different time point and OD540 was determined. Samples were taken in duplicates and the average OD$_{540}$ calculated and plotted against time of sampling 5. Results.

All colonies containing either the plasmid pPK727 or the pYES2 control plasmid were able to grow on plates with glucose as carbon source. When transferred to plates with galactose as the sole carbon source leading to gene expression from the P-gal1 promoter only cells with the pYES2 control plasmid showed normal growth, whereas cells containing the pPK727 were strongly inhibited in growth.

In liquid media, the yeast cells in which the relE gene was induced showed a remarked growth inhibition when compared to the uninduced control and to the controls with only the plasmid pYES2 without insert.

These results that are summarised in the below Table 16.1 clearly suggest that inhibition of cell growth in yeast cells is due to expression of the relE gene.

TABLE 16.1

Growth of *Saccharomyces cerevisiae* transformed with pYES2 +/− relE gene

| time (hours) | Plasmid + relE Galactose | no galactose | plasmid (control) galactose | no galactose |
|---|---|---|---|---|
| 0 | 0 | 0 | 0 | 0 |
| 5.5 | 0.018 | 0.024 | 0.023 | 0.028 |
| 15.5 | 0.013 | 0.186 | 0.055 | 0.176 |
| 23 | 0.190 | 1.195 | 0.286 | 0.963 |
| 28 | 0.010 | 1.480 | 0.816 | 1.649 |
| 29 | 0.035 | 3.930 | 1.660 | 2.650 |
| 65 | 0.990 | 3.950 | 6.180 | 3.820 |

REFERENCES

Altschul, S. F., Gish, W., Miller, W., Myers, E. W., and Lipman, D. J. (1990). Basic local alignment search tool. J Mol Biol 215:403-410.

Baum J. A. 1994. Tn5401, a new class II transposable element from *Bacillus thuringiensis*. J Bacteriol 176:2835-2845.

Bech F. W, Jorgensen S. T, Diderichsen B, Karlstrom O. H. 1985. Sequence of the relB transcription unit from *Escherichia coli* and identification of the relB gene. EMBO J 4:1059-1066.

Bertani, G. (1951). The mode of phage liberation by lysogenic *Escherichia coli*. J Bacteriol 62:293-300.

Bolivar, P. (1978). Construction and characterization of new cloning vehicles. III. Derivatives of plasmid pBR322 carrying unique EcoRI sites for selection of EcoRI generated recombinant DNA molecules. Gene 4:121-136.

Bult C. J, White O, Olsen G. J, Zhou L, Fleischmann R. D, Sutton G. G, Blake J. A, FitzGerald L. M, Clayton R. A, Gocayne J. D, Kerlavage A. R, Dougherty B. A, Tomb J. F, Adams M. D, Reich C. I, Overbeek R, Kirkness E. F, Weinstock K. G, Merrick J. M, Glodek A, Scott J. L, Geoghagen N. S. M, Weidman J. F, Fuhrmann J. L, Venter J. C et al. 1996. Complete genome sequence of the methanogenic archaeon, *Methanococcus jannaschii*. Science 273:1058-1073.

Casadaban M. J, Cohen S. N. 1980. Analysis of gene control signals by DNA fusion and cloning in *Escherichia coli*. J Mol Biol 138:179-207.

Clark, D. and Maaløe, 0.1967. DNA replication and the division cycle in *Escherichia coli*. J Mol Biol 23:99-112.

Dam, M. and Gerdes, K. 1994. Partitioning of plasmid R1: Ten direct repeats flanking the parA promoter constitute a centromere-like partition site parC, that expresses incompatibility. J. Mol. Biol. 236:1289-1298.

Fleischmann R. D, Adams M. D, White O, Clayton R. A, Kirkness E. F, Kerlavage A. R, Bull C. J, Tomb J. F, Dougherty B. A, Merrick J. M et al. 1995. Whole-genome random sequencing and assembly of *Haemophilus influenzae* Rd. Science 269:496-512.

Gerdes, K., Bech, F. W., Jørgensen, S. T., Løbner-Olesen, A., Atlung, T., Boe, L., Karlstrøm, O., Molin, S, and von Meyenburg, K. 1986. Mechanism of postsegregational killing by the hok gene product of the parB system of plasmid R1 and its homology with the relF gene product of the E. coli relB operon. EMBO J. 5:2023-2029.

Gotfredsen, M. and Gerdes, K. 1998. The *Escherichia coli* relBE genes belong to a new toxin-antitoxin gene family. Molec. Microbiol, 29:1065-1076.

Guzman L. M, Belin D, Carson M. J, Beckwith J. 1995. Tight regulation, modulation, and high-level expression by vectors containing the arabinose PBAD promoter. J Bacteriol 177:4121-4130.

Jensen, R. B. and Gerdes, K. 1995. Microreview. Programmed cell death in bacteria: proteic plasmid stabilization systems. Mol Microbiol 17:205-210.

Klenk H. P, Clayton R. A, Tomb J. F, White O, Nelson K. E, Ketchum K. A, Dodson R. J, Gwinn M, Hickey E. K, Peterson J. D, Richardson D. L, Kerlavage A. R, Graham D. E, Kyrpides N. C, Fleischmann R. D, Quackenbush J, Lee N. H, Sutton G. G, Gill S, Kirkness E. F, Dougherty B. A, McKenney K, Adams M. D, Loftus B, Venter J. C et al. 1997. The complete genome sequence of the hyperthermophilic, sulphate-reducing archaeon *Archaeoglobus fulgidus*. Nature 390:364-370.

Lanzer M, Bujard H. 1988. Promoters largely determine the efficiency of repressor action. Proc Natl Acad Sci U.S.A. 85:8973-8977.

Miller, J. F. (1972). Experiments in molecular genetics. Cold Spring Harbor Laboratory Press, New York.

Minton N. P. 1984. Improved plasmid vectors for the isolation of translational lac gene fusions. Gene 31:269-273.

Saul D, Spiers A. J, McAnulty J, Gibbs M. G, Bergquist P. L, Hill D. F. 1989. Nucleotide sequence and replication characteristics of RepFIB, a basic replicon of IncF plasmids. J Bacteriol 171:2697-2707.

Shägger, H. and von Jagow, G. (1987). Tricine-Sodium Dodecyl Sulfate-polyacrylamide gel electrophoresis for the separation of proteins in the range from 1 to 100 kD. Anal Biochem 166:368-379.

Simon, R., O'Connell, M., Labes, M. and Puhler, A. 1986. Plasmid vectors for the genetic manipulation of *rhizobia* and other gram-negative bacteria. Methods. Enzymol. 118: 640-659.

Thisted, T., Nielsen, A. and Gerdes, K. 1994. Mechanism of post-segregational killing: translation of Hok, SrnB, and PndA mRNAs of plasmids R1, F and R483 is activated by 3'-end processing. EMBO J. 13:1950-1959.

---

What is claimed is:

1. A method of conditionally controlling the survivability of a recombinant microbial cell population in a medium, said method comprising:

providing cells of a recombinant microbial cell population, which comprise a gene coding for a gene product of interest, with a gene coding for a cytotoxin polypeptide of a proteic killer gene system, wherein said gene coding for said cytotoxin polypeptide is operably linked to a regulatable, regulatory DNA sequence comprising a promoter that regulates the expression of said cytotoxin polypeptide at the transcriptional level in response to the presence or absence of a compound in the medium, such that said cytotoxin is expressed.

2. The method according to claim 1, wherein the cells of said cell population are further provided with a gene coding for an antidote polypeptide of said proteic killer gene system, wherein said antidote polypeptide binds to said cytotoxin polypeptide, thereby resulting in at least a partial counteraction of the toxic effect of said cytotoxin polypeptide.

3. The method according to claim 2, wherein the gene coding for said antidote polypeptide that binds to said cytotoxin polypeptide of said proteic killer gene system is operably linked to a regulatable, regulatory DNA sequence such that said gene coding for said antidote polypeptide is suppressed under conditions whereby said gene coding for said cytotoxin polypeptide is expressed.

4. The method according to claim 2, wherein the expression of said genes coding for said cytotoxin and/or antidote polypeptide of said proteic killer gene system is stochastically regulated.

5. The method according to claim 4, wherein said stochastical regulation is effected by operably linking said genes coding for said cytotoxin and/or antidote polypeptide of said proteic killer gene system to a regulatory sequence that comprises an invertible promoter.

6. The method according to claim 4, wherein said stochastical regulation is effected by flanking at least part of said regulatory sequence by repeat sequences such that at least part of said regulatory sequence is then recombinationally excised.

7. The method according to claim 1, wherein at least one of said genes of said proteic killer gene system is present on the chromosome of said cell.

8. The method according to claim 1, wherein at least one of said genes of said proteic killer gene system is present on an extrachromosomal replicon.

9. The method according to claim 1, wherein said cytotoxin polypeptide inhibits translation.

10. The method according to claim 1, wherein said genes of said proteic killer gene system are derived from Gram-negative bacteria, Gram-positive bacteria or from a species belonging to the Archae.

11. The method according to claim 1, wherein said Gram-negative bacteria are selected from the group consisting of *Enterobacteriaceae* spp., *Hemophilus* spp., *Vibrionaceae* spp., *Pseudomonadaceae* spp., *Helicobacter* spp. and *Synechosystis* spp.

12. The method according to claim 1, wherein said Gram-positive bacteria are selected from the group consisting of lactic acid bacterial spp., *Bacillaceae* spp. and *Mycobacterium* spp.

13. The method according to claim 12, wherein said Gram-positive bacterium is *Bacillus thuringiensis.*

14. The method according to claim 1, wherein said gene coding for said cytotoxin polypeptide of said proteic killer gene system, when expressed, results in the formation of a cytotoxin polypeptide selected from the group consisting of an *E. coli* K-12 relE polypeptide, an *E. coli* plasmid P307 relE polypeptide, a plasmid F CcdB polypeptide, a plasmid R1 PemK polypeptide, a plasmid RP4 ParE polypeptide, a prophage P1 Doc polypeptide, a *Streptococcus pneumoniae* cytotoxin polypeptide, an Archeon *Methanococcus janashii* cytotoxin polypeptide and a functionally equivalent polypeptide which is a derivative of any of the aforementioned polypeptides, the sequence of which has been modified by substitution, deletion or addition of one or more amino acids while the gene product of which has retained at least part of the function of the gene product of the non modified sequence.

15. The method according to claim 1, wherein said promoter is inducible by a chemical compound.

16. The method according to claim 1, wherein said promoter is suppressible by a first kind of chemical compound and inducible by a second kind of chemical compound such that when said first kind of compound is depleted from the medium, the promoter is induced by said second kind of compound.

17. The method according to claim 1, wherein said gene product of interest is an immunologically active gene product.

18. The method according to claim 1, wherein said gene product of interest is one that is effective in degradation of an environmental pollutant.

19. The method according to claim 1, wherein said gene product of interest is a pesticidally active product.

20. The method according to claim 19, wherein said gene coding for said pesticidally active gene product is derived from *Bacillus thuringiensis.*

21. The method according to claim 1 further comprising the steps of:
    providing in the cell of the recombinant microbial cell population at least a gene coding for a cytotoxin polypeptide of a proteic killer gene system, said gene expressible in said cells of said cell population, wherein said gene is operably linked to a regulatory DNA sequence; and
    cultivating said cell population under conditions whereby said gene coding for said cytotoxin polypeptide is expressed, said expression leading to at least a partial killing of said cell population.

22. The method of claim 1, wherein said promoter regulates the expression of said cytotoxin polypeptide in response to the presence of a compound in the medium.

23. The method of claim 1, wherein said promoter regulates the expression of said cytotoxin polypeptide in response to the absence of a compound in the medium.

* * * * *